US008404239B2

(12) United States Patent
Siebel et al.

(10) Patent No.: US 8,404,239 B2
(45) Date of Patent: Mar. 26, 2013

(54) ANTI-NOTCH2 NRR ANTIBODIES

(75) Inventors: Christian W. Siebel, Berkeley, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 471 days.

(21) Appl. No.: 12/570,267

(22) Filed: Sep. 30, 2009

(65) Prior Publication Data

US 2010/0080808 A1 Apr. 1, 2010

Related U.S. Application Data

(60) Provisional application No. 61/101,917, filed on Oct. 1, 2008.

(51) Int. Cl.

| | |
|---|---|
| ***A61K 39/395*** | (2006.01) |
| ***C07K 16/28*** | (2006.01) |
| *C07K 14/705* | (2006.01) |

(52) U.S. Cl. ............... 424/143.1; 424/133.1; 424/138.1; 424/141.1; 514/19.2; 530/350; 530/387.1; 530/388.1; 530/388.22; 530/387.7

(58) Field of Classification Search ........................ None
See application file for complete search history.

(56) References Cited

U.S. PATENT DOCUMENTS

| | | | | |
|---|---|---|---|---|
| 5,648,464 | A | 7/1997 | Artavanis-Tsakonas et al. | |
| 5,780,300 | A | 7/1998 | Artavanis-Tsakonas et al. | |
| 5,786,158 | A | 7/1998 | Artavanis-Tsakonas et al. | |
| 5,789,195 | A | 8/1998 | Artavanis-Tsakonas et al. | |
| 6,083,904 | A | 7/2000 | Artavanis-Tsakonas | |
| 6,090,922 | A | 7/2000 | Artavanis-Tsakonas et al. | |
| 6,149,902 | A | 11/2000 | Artavanis-Tsakonas et al. | |
| 6,436,650 | B1 | 8/2002 | Artavanis-Tsakonas et al. | |
| 6,692,919 | B1 | 2/2004 | Artavanis-Tsakonas et al. | |
| 7,083,789 | B2 | 8/2006 | Ramakrishna et al. | |
| 7,919,092 | B2 * | 4/2011 | Lewicki et al. | 424/141.1 |
| 8,206,713 | B2 | 6/2012 | Lewicki et al. | |
| 8,226,943 | B2 | 7/2012 | Gurney et al. | |
| 2004/0058443 | A1 | 3/2004 | Artavanis-Tsakonas et al. | |
| 2004/0242482 | A1 | 12/2004 | Gehring et al. | |
| 2005/0112121 | A1 | 5/2005 | Artavanis-Tsakonas et al. | |
| 2005/0158859 | A1 | 7/2005 | Artavanis-Tsakonas et al. | |
| 2007/0003983 | A1 | 1/2007 | Artavanis-Tsakonas et al. | |
| 2008/0107648 | A1 | 5/2008 | Noguera et al. | |
| 2008/0118520 | A1 | 5/2008 | Li et al. | |
| 2008/0131908 | A1 | 6/2008 | Li et al. | |
| 2008/0226621 | A1 | 9/2008 | Fung et al. | |
| 2008/0241150 | A1 * | 10/2008 | Blacklow et al. | 424/139.1 |
| 2008/0260734 | A1 | 10/2008 | Clarke et al. | |
| 2009/0258026 | A2 | 10/2009 | Siebel et al. | |

FOREIGN PATENT DOCUMENTS

| | | | |
|---|---|---|---|
| WO | WO 00/20576 | | 4/2000 |
| WO | WO 02/24221 | A2 | 3/2002 |
| WO | WO 2006/053063 | A2 | 5/2006 |
| WO | WO 2006/068822 | A1 | 6/2006 |
| WO | 2007/145840 | A2 | 12/2007 |
| WO | 2008/057144 | A2 | 5/2008 |
| WO | 2008/091641 | | 7/2008 |
| WO | WO 2008/150525 | A1 | 12/2008 |
| WO | WO 2006/015375 | A2 | 2/2009 |

OTHER PUBLICATIONS

Bost et al. Antibodies against a peptide sequence within the HIV envelope protein crossreacts with human interleukin-2. Immunol Invest 17 (6&7): 577-586, 1988.*
Bendayan et al. Possibilities of false immunocytochemical results generated by the use of monoclonal antibodies: the example of the anti-proinsulin antibody. J Histochem Cytochem 43: 881-886, 1995.*
Huppert et al. Embryonic lethality in mice homozygous for a processing-deficient allele of Notch1. Nature 405: 966-970, 2000.*
"Anti-Notch2 Monoclonal antibody" datasheet from Applied Biological Materials, Inc.; downloaded Jun. 6, 2012, 1 page.*
Notch2 (D76A6) XP Rabbit Monoclonal Antibody datasheet from Cell Signaling Technology; downloaded Jun. 6, 2012, 1 page.*
"Notch Antibodies" Table downloaded from Santa Cruz Biotechnology, Inc. on Jun. 5, 2012; www.scbt.com/table-notch.html; 2 pages.*
Notch1 (A-8) antibody technical datasheet; downloaded from Santa Cruz Biotechnology Inc. www.sbct.com/datasheet-376403-notch-1-a-8-antibody.html; Jun. 6, 2012, 1 page.*
Notch1 (C-10) antibody technical datasheet; downloaded from Santa Cruz Biotechnology Inc. www.sbct.com/datasheet-373891-notch-1-c-10-antibody.html; Jun. 6, 2012, 1 page.*
Notch1 (E-4) antibody technical datasheet; downloaded from Santa Cruz Biotechnology Inc. www.sbct.com/datasheet-373944-notch-1-e-4-antibody.html; Jun. 6, 2012, 1 page.*
Notch1 (mN1A) antibody technical datasheet; downloaded from Santa Cruz Biotechnology Inc. www.sbct.com/datasheet-37245-notch-1-mn1a-antibody.html; Jun. 6, 2012, 1 page.*
"Anti-Notch1 clone mN1A antibody" datasheet from Sigma-Aldrich, Inc. dated Dec. 2003; downloaded on Jun. 6, 2012, 2 pages.*
"Anti-Notch1 monoclonal antibody, clone 4G1" datasheet from Sigma-Aldrich, Inc.; downloaded Jun. 6, 2012; 2 pages.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*

(Continued)

*Primary Examiner* — Bridget E Bunner
(74) *Attorney, Agent, or Firm* — Julia vom Wege

(57) ABSTRACT

The invention provides anti-Notch antibodies, and in particular, antibodies that bind Notch2 NRR, and methods of using the same.

48 Claims, 33 Drawing Sheets

OTHER PUBLICATIONS

Ngo et al. Computational complexity, protein structure prediction, and the Levinthal paradox. The Protein Folding Problem and Tertiary Structure Prediction, pp. 492-495, 1994.*

Brummell et al. (Biochemistry 32:1180-1187 (1993)).*

Kobayashi et al. (Protein Engineering 12:879-844 (1999)).*

Burks et al. (PNAS 94:412-417 (1997)).*

Jang et al. (Molec. Immunol. 35:1207-1217 (1998)).*

Brorson et al. (J. Immunol. 163:6694-6701 (1999)).*

Coleman (Research in Immunol. 145:33-36 (1994)).*

Falk et al. Generation of anti-Notch antibodies and their application in blocking Notch signalling in neural stem cells. Methods 58: 69-78, 2012.*

Wu et al. Therapeutic antibody targeting of individual Notch receptors. Nature 464(7291): 1052-1057, 2010; 8 total pages.*

Massi et al. Evidence for differential expression of Notch receptors and their ligands in melanocytic nevi and cutaneous malignant melanoma. Modern Pathology 19: 246-254, 2006.*

Allenspach et al., "Notch signaling in cancer" *Cancer Biol Ther.* 1(5):466-76 (2002).

Aster et al., "The folding and structural integrity of the first LIN-12 module of human Notch1 are calcium-dependent" *Biochemistry* 38(15):4736-42 (Apr. 1999).

Bray, "Notch signalling: a simple pathway becomes complex" *Nat Rev Mol Cell Biol.* 7(9):678-89 (Sep. 2006).

Chiang et al., "Identification of a conserved negative regulatory sequence that influences the leukemogenic activity of NOTCH1" *Molecular & Cellular Biology* 26(16) :6261-6271 (Aug. 2006).

Chiba, "Notch signaling in stem cell systems" *Stem Cells* 24(11):2437-47 (Nov. 2006).

Feldman et al., "A carboxy-terminal deletion mutant of Notch1 accelerates lymphoid oncogenesis in E2A-PBX1 transgenic mice" *Blood* 96(5):1906-1913 (Sep. 1, 2000).

Hoek et al., "Expression profiling reveals novel pathways in the transformation of melanocytes to melanomas" *Cancer Research* 64:5270-5282 (Aug. 1, 2004).

Hubmann et al., "Notch2 is involved in the overexpression of CD23 in B-cell chronic lymphocytic leukemia" *Blood* 99(10):3742-3747 (May 15, 2002).

Jang et al., "Notch signaling as a target in multimodality cancer therapy" *Curr Opin Mol Ther.* 2(1):55-65 (Feb. 2000).

Jonsson et al., "Genomic profiling of malignant melanoma using tiling-resolution arrayCGH" *Oncogene* 26:4738-4748 (2007).

Joutel and Tournier-Lasserve, "Notch signalling pathway and human diseases" *Seminars in Cell & Dev Biol* 9:619-625 (1998).

Jundt et al., "Jagged1-induced Notch signaling drives proliferation of multiple myeloma cells" *Blood* 103(9):3511-5 (May 2004).

Leong and Karsan, "Recent insights into the role of Notch signaling in tumorigenesis" *Blood* 107:2223-2233 (2006).

Lopez-Nieva et al., "Defective expression of Notch1 and Notch2 in connection to alterations of c-Myc and Ikaros in γ-radiation-induced mouse thymic lymphomas" *Carcinogenesis* 25(7):1299-1304 (2004).

Malecki et al., "Leukemia-associated mutations within the NOTCH1 heterodimerization domain fall into at least two distinct mechanistic classes" *Mol Cell Biol.* 26(12) :4642-51 (Jun. 2006).

McDaniell et al., "NOTCH2 mutations cause Alagille syndrome, a heterogeneous disorder of the Notch signaling pathway" *Am. J. Hum. Gen.* 79:169-173 (Jul. 2006).

Nam et al., "Notch signaling as a therapeutic target" *Curr Opin Chem Biol.* 6(4):501-9 (Aug. 2002).

Parr et al., "The possible correlation of Notch-1 and Notch-2 with clinical outcome and tumour clinicopathological parameters in human breast cancer" *Int. J. Mol. Med.* 14:779-786 (2004).

Pillai et al., "Marginal zone B cells" *Annu. Rev. Immunol.* 23:161-196 (2005).

Sanchez-Irizarry et al., "Notch subunit heterodimerization and prevention of ligand-independent proteolytic activation depend, respectively, on a novel domain and the LNR repeats" *Mol Cell Biol.* 24(21):9265-73 (2004)

Seykora et al., "Gene expression profiling of melanocytic lesions" *Am. J. Dermatopathol.* 25(1) :6-11 (2003).

Sullivan and Bicknell, "New molecular pathways in angiogenesis" *British Journal of Cancer* 89 (2) :228-231 (Jul. 21, 2003).

Thelu et al., "Notch signalling is linked to epidermal cell differentiation level in basal cell carcinoma, psoriasis and wound healing" *BMC Dermatology* 2:7 (2002).

Vardar et al., "Nuclear magnetic resonance structure of a prototype Lin12-Notch repeat module from human Notch1" *Biochemistry* 42:7061-7067 (2003).

von Boehmer, H., "Notch in lymphopoiesis and T cell polarization" *Nature Immunol.* 6(7):641-642 (Jul. 2005).

Weng et al., "Activating mutations of NOTCH1 in human T cell acute lymphoblastic leukemia" *Science* 306(5694):269-271 (Oct. 8, 2004).

Zweidler-McKay, "Notch signaling is a potent inducer of growth arrest and apoptosis in a wide range of B-cell malignancies" *Blood* 106(12):3898-3906 (Dec. 1, 2005).

Bolos et al., "Notch signaling in development and cancer" *Endocr Rev.* 28(3):339-63 (May 2007).

Gordon et al., "Structural basis for autoinhibition of Notch" *Nat Struct Mol Biol.* 14(4):295-300 (Apr. 2007).

Li et al., "Modulation of Notch Signaling by Antibodies Specific for the Extracellular Negative Regulatory Region of NOTCH3" *Journal of Biological Chemistry* 283(12) :8046-8054 (Mar. 21, 2008).

PCT International Search Report, mailed Dec. 18, 2009, in counterpart PCT International Application No. PCT/US2009/059028, filed Sep. 30, 2009.

Rehman et al., "Notch Signaling in the Regulation of Tumor Angiogenesis" *Trends in Cell Biology* 16(6):293-300 (Jun. 2006).

Yin et al., "Monoclonal anitbody MX35 detects the membrane transporter NaPi2b (SLC34A2) in human carcinomas" Cancer Immunity 8:3 (Feb. 6, 2008).

* cited by examiner

HVR-H1 Sequences - Antibody D and Affinity Matured Antibodies Derived from Antibody D

| | | Kabat Number | | | | | | | | | |
|---|---|---|---|---|---|---|---|---|---|---|---|
| Antibody # | SEQ ID NO: | 26 | 27 | 28 | 29 | 30 | 31 | 32 | 33 | 34 | 35 |
| D | 1 | G | Y | S | F | T | S | Y | G | M | S |
| D-1, D-2, D-3 | 2 | G | Y | T | F | S | S | Y | G | M | S |
| Consensus | 3 | G | Y | S/T | F | S/T | S | Y | G | M | S |

HVR-H2 Sequence - Antibody D and Affinity Matured Antibodies Derived from Antibody D

| | | Kabat Number | | | | | | | | | | | | | | | | | |
|---|---|---|---|---|---|---|---|---|---|---|---|---|---|---|---|---|---|---|---|
| Antibody # | SEQ ID NO: | 49 | 50 | 51 | 52 | 52a | 53 | 54 | 55 | 56 | 57 | 58 | 59 | 60 | 61 | 62 | 63 | 64 | 65 |
| D, D-1, D-2, D-3 | 4 | S | Y | I | Y | P | Y | S | G | A | T | Y | Y | A | D | S | V | K | G |

HVR-H3 Sequence - Antibody D and Affinity Matured Antibodies Derived from Antibody D

| | | Kabat Number | | | | | | | | | | | | |
|---|---|---|---|---|---|---|---|---|---|---|---|---|---|---|
| Antibody # | SEQ ID NO: | 95 | 96 | 97 | 98 | 99 | 100 | 100A | 100B | 100C | 100D | 100K | 101 | 102 |
| D, D-1, D-2, D-3 | 5 | H | S | G | Y | Y | R | I | S | S | A | M | D | V |

FIG. 1

HVR-L1 Sequences - Antibody D and Affinity Matured Antibodies Derived from Antibody D

| | | Kabat Number | | | | | | | | | | |
|---|---|---|---|---|---|---|---|---|---|---|---|---|
| Antibody # | SEQ ID NO: | 24 | 25 | 26 | 27 | 28 | 29 | 30 | 31 | 32 | 33 | 34 |
| D | 6 | R | A | S | Q | S | I | S | S | Y | L | A |
| D-1 | 7 | R | A | S | Q | S | N | R | R | F | L | A |
| D-2 | 8 | R | A | S | Q | S | V | R | S | F | L | A |
| D-3 | 9 | R | A | S | Q | N | I | K | R | F | L | A |
| Consensus | 10 | R | A | S | Q | S/N | I/N/V | S/R/K | S/R | Y/F | L | A |

HVR-L2 Sequences - Antibody D and Affinity Matured Antibodies Derived from Antibody D

| | | Kabat Number | | | | | | |
|---|---|---|---|---|---|---|---|---|
| Antibody # | SEQ ID NO: | 50 | 51 | 52 | 53 | 54 | 55 | 56 |
| D, D-1 | 11 | G | A | S | S | R | A | S |
| D-2 | 12 | R | A | S | I | R | A | S |
| D-3 | 13 | G | A | S | T | R | E | S |
| Consensus | 14 | G/R | A | S | S/I/T | R | A/E | S |

HVR-L3 Sequences - Antibody D and Affinity Matured Antibodies Derived from Antibody D

| | | Kabat Number | | | | | | | | |
|---|---|---|---|---|---|---|---|---|---|---|
| Clone # | SEQ ID NO: | 89 | 90 | 91 | 92 | 93 | 94 | 95 | 96 | 97 |
| D | 15 | Q | Q | Y | Y | S | S | P | L | T |
| D-1 | 16 | Q | Q | Y | Y | I | S | P | L | T |
| D-2 | 17 | Q | Q | Y | Y | I | S | P | W | T |
| D-3 | 18 | Q | Q | Y | Y | R | S | P | H | T |
| Consensus | 19 | Q | Q | Y | Y | S/I/R | S | P | L/W/H | T |

FIG. 2

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 35B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | E | V | Q | L | V | E | S | G | G | G | L | V | Q | P | G | G | S | L | R | L | S | C | A | A | S | G | Y | S | F | T | S | Y | G | M | S | | | W | V | R | Q | A | P | G | K |
| Antibody D-1 | E | V | Q | L | V | E | S | G | G | G | L | V | Q | P | G | G | S | L | R | L | S | C | A | A | S | G | Y | T | F | S | S | Y | G | M | S | | | W | V | R | Q | A | P | G | K |
| Antibody D-2 | E | V | Q | L | V | E | S | G | G | G | L | V | Q | P | G | G | S | L | R | L | S | C | A | A | S | G | Y | T | F | S | S | Y | G | M | S | | | W | V | R | Q | A | P | G | K |
| Antibody D-3 | E | V | Q | L | V | E | S | G | G | G | L | V | Q | P | G | G | S | L | R | L | S | C | A | A | S | G | Y | T | F | S | S | Y | G | M | S | | | W | V | R | Q | A | P | G | K |

| Kabat# | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |
| Antibody D-1 | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |
| Antibody D-2 | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |
| Antibody D-3 | G | L | E | W | V | S | Y | I | Y | P | | | Y | S | G | A | T | Y | Y | A | D | S | V | K | G | R | F | T | I | S | A | D | T | S | K | N | T | A | Y | L | Q | M | N |

| Kabat# | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | S | L | R | A | E | D | T | A | V | Y | Y | C | A | R | H | S | G | Y | Y | R | I | S | S | A | | | | | | | M | D | V | W | G | Q | G | T | L | V | T | V | S | A | SEQ ID NO: 20 |
| Antibody D-1 | S | L | R | A | E | D | T | A | V | Y | Y | C | A | R | H | S | G | Y | Y | R | I | S | S | A | | | | | | | M | D | V | W | G | Q | G | T | L | V | T | V | S | A | SEQ ID NO: 21 |
| Antibody D-2 | S | L | R | A | E | D | T | A | V | Y | Y | C | A | R | H | S | G | Y | Y | R | I | S | S | A | | | | | | | M | D | V | W | G | Q | G | T | L | V | T | V | S | A | SEQ ID NO: 21 |
| Antibody D-3 | S | L | R | A | E | D | T | A | V | Y | Y | C | A | R | H | S | G | Y | Y | R | I | S | S | A | | | | | | | M | D | V | W | G | Q | G | T | L | V | T | V | S | A | SEQ ID NO: 21 |

FIG. 3

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | D | I | Q | M | T | Q | S | P | S | S | L | S | A | S | V | G | D | R | V | T | I | T | C | R | A | S | Q | | | | | | | S | I | S | S | Y | L | A | W | Y | Q |
| Antibody D-1 | D | I | Q | M | T | Q | S | P | S | S | L | S | A | S | V | G | D | R | V | T | I | T | C | R | A | S | Q | | | | | | | S | N | R | R | F | L | A | W | Y | Q |
| Antibody D-2 | D | I | Q | M | T | Q | S | P | S | S | L | S | A | S | V | G | D | R | V | T | I | T | C | R | A | S | Q | | | | | | | S | V | R | S | F | L | A | W | Y | Q |
| Antibody D-3 | D | I | Q | M | T | Q | S | P | S | S | L | S | A | S | V | G | D | R | V | T | I | T | C | R | A | S | Q | | | | | | | N | I | K | R | F | L | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Antibody D | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| Antibody D-1 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| Antibody D-2 | Q | K | P | G | K | A | P | K | L | L | I | Y | R | A | S | I | R | A | S | G | V | P | S | R | F | S | G | S | G | S | G | T | D | F | T | L | T | I | S | S | L | Q | P |
| Antibody D-3 | Q | K | P | G | K | A | P | K | L | L | I | Y | G | A | S | T | R | E | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|---|---|---|---|---|---|
| Antibody D | E | D | F | A | T | Y | Y | C | Q | Q | Y | Y | S | S | P | | | | | | | L | T | F | G | Q | G | T | K | V | E | I | K | R | SEQ ID NO: 22 |
| Antibody D-1 | E | D | F | A | T | Y | Y | C | Q | Q | Y | Y | I | S | P | | | | | | | L | T | F | G | Q | G | T | K | V | E | I | K | R | SEQ ID NO: 23 |
| Antibody D-2 | E | D | F | A | T | Y | Y | C | Q | Q | Y | Y | I | S | P | | | | | | | W | T | F | G | Q | G | T | K | V | E | I | K | R | SEQ ID NO: 24 |
| Antibody D-3 | E | D | F | A | T | Y | Y | C | Q | Q | Y | Y | R | S | P | | | | | | | H | T | F | G | Q | G | T | K | V | E | I | K | R | SEQ ID NO: 25 |

FIG. 4

```
              FR1                                                       FR2
I
A   QVQLVQSGAEVKKPGASVKVSCKASGYTFT         -H1-   WVRQAPGQGLEWMG        -H2-     RVTIT
B   QVQLVQSGAEVKKPGASVKVSCKAS      -H1-           WVRQAPGQGLEWM       -H2-       RVTIT
C   QVQLVQSGAEVKKPGASVKVSCKAS      -H1-           WVRQAPGQGLEWM       -H2-       RVTIT
D   QVQLVQSGAEVKKPGASVKVSCKAS      -H1-           WVRQAPGQGLEWM       -H2-       RVTIT
II
A   QVQLQESGPGLVKPSQTLSLTCTVSGGSVS         -H1-   WIRQPPGKGLEWIG        -H2-     RVTIS
B   QVQLQESGPGLVKPSQTLSLTCTVS      -H1-           WIRQPPGKGLEWI       -H2-       RVTIS
C   QVQLQESGPGLVKPSQTLSLTCTVS      -H1-           WIRQPPGKGLEWI       -H2-       RVTIS
D   QVQLQESGPGLVKPSQTLSLTCTVS      -H1-           WIRQPPGKGLEWI       -H2-       RVTIS
III
A   EVQLVESGGGLVQPGGSLRLSCAASGFTFS         -H1-   WVRQAPGKGLEWVS        -H2-     RFTIS
B   EVQLVESGGGLVQPGGSLRLSCAAS      -H1-           WVRQAPGKGLEWV       -H2-       RFTIS
C   EVQLVESGGGLVQPGGSLRLSCAAS      -H1-           WVRQAPGKGLEWV       -H2-       RFTIS
D   EVQLVESGGGLVQPGGSLRLSCAAS      -H1-           WVRQAPGKGLEWV       -H2-       RFTIS
Acceptor - 1
A   EVQLVESGGGLVQPGGSLRLSCAASGFNIK         -H1-   WVRQAPGKGLEWVS        -H2-     RFTIS
B   EVQLVESGGGLVQPGGSLRLSCAAS      -H1-           WVRQAPGKGLEWV       -H2-       RFTIS
C   EVQLVESGGGLVQPGGSLRLSCAAS      -H1-           WVRQAPGKGLEWV       -H2-       RFTIS
Acceptor - 2
A   EVQLVESGGGLVQPGGSLRLSCAASGFNIK         -H1-   WVRQAPGKGLEWVS        -H2-     RFTIS
B   EVQLVESGGGLVQPGGSLRLSCAAS      -H1-           WVRQAPGKGLEWV       -H2-       RFTIS
C   EVQLVESGGGLVQPGGSLRLSCAAS      -H1-           WVRQAPGKGLEWV       -H2-       RFTIS
D   EVQLVESGGGLVQPGGSLRLSCAAS      -H1-           WVRQAPGKGLEWV       -H2-       RFTIS
```

FIG. 5A

| | FR3 | | FR4 | SEQ ID NOs of FR1, FR2, FR3, FR4 |
|---|---|---|---|---|
| I | | | | |
| A | ADTSTSTAYMELSSLRSEDTAVYYCAR | -H3- | WGQGTLVTVSS | SEQ ID NO.: 32, 33, 34, 35 |
| B | ADTSTSTAYMELSSLRSEDTAVYYCAR | -H3- | WGQGTLVTVSS | SEQ ID NO.: 36, 37, 34, 35 |
| C | ADTSTSTAYMELSSLRSEDTAVYYCA | -H3- | WGQGTLVTVSS | SEQ ID NO.: 36, 37, 38, 35 |
| D | ADTSTSTAYMELSSLRSEDTAVYYC | -H3- | WGQGTLVTVSS | SEQ ID NO.: 36, 37, 39, 35 |
| II | | | | |
| A | VDTSKNQFSLKLSSVTAADTAVYYCAR | -H3- | WGQGTLVTVSS | SEQ ID NO.: 40, 41, 42, 35 |
| B | VDTSKNQFSLKLSSVTAADTAVYYCAR | -H3- | WGQGTLVTVSS | SEQ ID NO.: 43, 44, 42, 35 |
| C | VDTSKNQFSLKLSSVTAADTAVYYCA | -H3- | WGQGTLVTVSS | SEQ ID NO.: 43, 44, 45, 35 |
| D | VDTSKNQFSLKLSSVTAADTAVYYC | -H3- | WGQGTLVTVSS | SEQ ID NO.: 43, 44, 46, 35 |
| III | | | | |
| A | RDNSKNTLYLQMNSLRAEDTAVYYCAR | -H3- | WGQGTLVTVSS | SEQ ID NO.: 47, 48, 49, 35 |
| B | RDNSKNTLYLQMNSLRAEDTAVYYCAR | -H3- | WGQGTLVTVSS | SEQ ID NO.: 50, 51, 49, 35 |
| C | RDNSKNTLYLQMNSLRAEDTAVYYCA | -H3- | WGQGTLVTVSS | SEQ ID NO.: 50, 51, 52, 35 |
| D | RDNSKNTLYLQMNSLRAEDTAVYYC | -H3- | WGQGTLVTVSS | SEQ ID NO.: 50, 51, 53, 35 |
| Acceptor - 1 | | | | |
| A | ADTSKNTAYLQMNSLRAEDTAVYYCSR | -H3- | WGQGTLVTVSS | SEQ ID NO.: 54, 48, 55, 35 |
| B | ADTSKNTAYLQMNSLRAEDTAVYYCSR | -H3- | WGQGTLVTVSS | SEQ ID NO.: 50, 51, 55, 35 |
| C | ADTSKNTAYLQMNSLRAEDTAVYYCS | -H3- | WGQGTLVTVSS | SEQ ID NO.: 50, 51, 56, 35 |
| Acceptor - 2 | | | | |
| A | ADTSKNTAYLQMNSLRAEDTAVYYCAR | -H3- | WGQGTLVTVSS | SEQ ID NO.: 54, 48, 57, 35 |
| B | ADTSKNTAYLQMNSLRAEDTAVYYCAR | -H3- | WGQGTLVTVSS | SEQ ID NO.: 50, 51, 57, 35 |
| C | ADTSKNTAYLQMNSLRAEDTAVYYCA | -H3- | WGQGTLVTVSS | SEQ ID NO.: 50, 51, 58, 35 |
| D | ADTSKNTAYLQMNSLRAEDTAVYYC | -H3- | WGQGTLVTVSS | SEQ ID NO.: 50, 51, 59, 35 |

FIG. 5B

| | FR1 | | FR2 | | FR3 |
|---|---|---|---|---|---|
| kv1 | DIQMTQSPSSLSASVGDRVTITC | -L1- | WYQQKPGKAPKLLIY | -L2- | GVPSRFSGSGSGTDFTLTISSLQP |
| kv2 | DIVMTQSPLSLPVTPGEPASISC | -L1- | WYLQKPGQSPQLLIY | -L2- | GVPDRFSGSGSGTDFTLKISRVEA |
| kv3 | EIVLTQSPGTLSLSPGERATLSC | -L1- | WYQQKPGQAPRLLIY | -L2- | GIPDRFSGSGSGTDFTLTISRLEP |
| kv4 | DIVMTQSPDSLAVSLGERATINC | -L1- | WYQQKPGQPPKLLIY | -L2- | GVPDRFSGSGSGTDFTLTISSLQA |

| | | FR4 | SEQ ID NOs of FR1, FR2, FR3, FR4 |
|---|---|---|---|
| EDFATYYC | -L3- | FGQGTKVEIK | SEQ ID NO.: 60, 61, 62, 63 |
| EDVGVYYC | -L3- | FGQGTKVEIK | SEQ ID NO.: 64, 65, 66, 63 |
| EDFAVYYC | -L3- | FGQGTKVEIK | SEQ ID NO.: 67, 68, 69, 63 |
| EDVAVYYC | -L3- | FGQGTKVEIK | SEQ ID NO.: 70, 71, 72, 63 |

FIG. 6

Framework Sequences of huMAb4D5-8 Light Chain Variable Domain

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 60)

LC-FR2 $^{35}$Trp Tyr Gln Gln Lys Pro Gly Lys Ala Pro Lys Leu Leu Ile Tyr$^{49}$ (SEQ ID NO: 61)

LC-FR3 $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 30)

LC-FR4 $^{98}$Phe Gly Gln Gly Thr Lys Val Glu Ile Lys$^{107}$ (SEQ ID NO: 63)

Framework Sequences of huMAb4D5-8 Heavy Chain Variable Domain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 50)

HC-FR2 $^{36}$Trp Val Arg Gln Ala Pro Gly Lys Gly Leu Glu Trp Val$^{48}$ (SEQ ID NO: 51)

HC-FR3 $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 59)

HC-FR4 $^{103}$Trp Gly Gln Gly Thr Leu Val Thr Val Ser Ser$^{113}$ (SEQ ID NO: 35)

*FIG. 7*

Framework Sequences of huMAb4D5-8 Light Chain Variable Domain Modified at Positions 66 and 99 (Underlined)

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 60)

LC-FR2 $^{35}$Trp Tyr Gln Gln Lys Pro Gly Lys Ala Pro Lys Leu Leu Ile Tyr$^{49}$ (SEQ ID NO: 61)

LC-FR3 $^{57}$Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys$^{88}$ (SEQ ID NO: 62)

LC-FR4 $^{98}$Phe Arg Gln Gly Thr Lys Val Glu Ile Lys$^{107}$ (SEQ ID NO: 31)

Framework Sequences of huMAb4D5-8 Heavy Chain Variable Domain Modified at Postions 71, 73 and 78 (Underlined)

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 50)

HC-FR2 $^{36}$Trp Val Arg Gln Ala Pro Gly Lys Gly Leu Glu Trp Val$^{48}$ (SEQ ID NO: 51)

HC-FR3 $^{66}$Arg Phe Thr Ile Ser Arg Asp Asn Ser Lys Asn Thr Leu Tyr Leu Gln Met Asn83 Ser83a Leu83b Arg83c Ala Glu Asp Thr Ala Val Tyr Tyr Cys$^{92}$ (SEQ ID NO: 53)

HC-FR4 $^{103}$Trp Gly Gln Gly Thr Leu Val Thr Val Ser Ser$^{113}$ (SEQ ID NO: 35)

*FIG. 8*

| Chimeric AP Protein | Binds α-NRR1 | Binds α-NRR2 | Chimeric AP Protein | Binds α-NRR1 | Binds α-NRR2 |
|---|---|---|---|---|---|
| Notch1 | Y | N | Notch2 | N | Y |
| BC.Hd | N | N | A | N | N |
| AB.Hd | Y | N | B | N | Y |
| ABC.Hc | Y | N | C | N | Y |
| AB.Hc | Y | N | HDc | N | N |
| AB | W | N | C.Hn | N | Y |
| Hd | N | N | BC.Hn | N | W |
| B.Hc | N | N | BC | N | Y |
| B.Hd | N | N | | | |
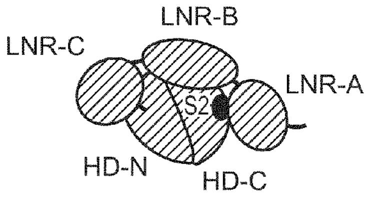
Notch1-NRR
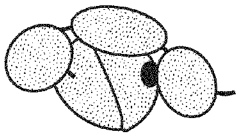
Notch2-NRR
FIG. 12A

| Chimeric AP Protein | | AP Expression | Binds α-NRR1 | Binds α-NRR2 |
|---|---|---|---|---|
| 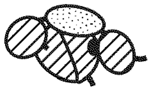 | AC.Hd | N | --- | --- |
| 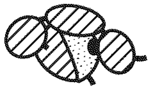 | ABC.Hn | W | N | N |
| 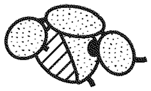 | Hn | N | --- | --- |
| 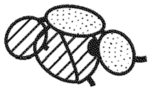 | C.Hd | W | N | N |
| 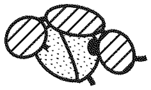 | ABC | W | W | N |
| 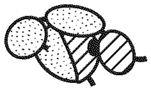 | A.Hc | W | W | N |
| 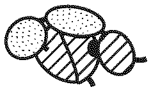 | A.Hd | W | W | N |
| 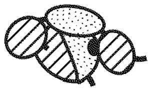 | AC.Hn | W | N | N |
| 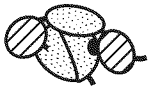 | AC | W | N | N |
*FIG. 17*

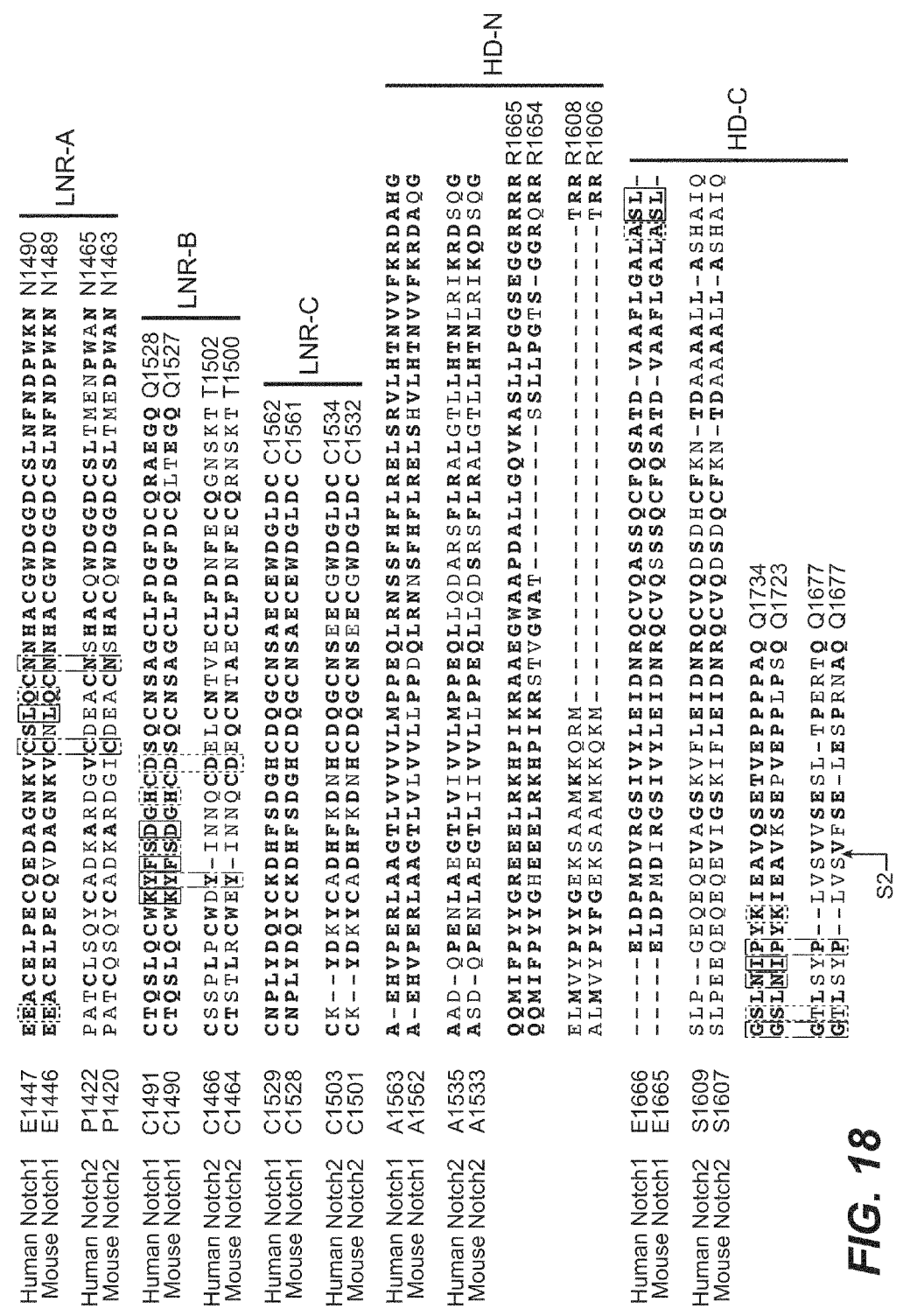

```
Human Notch1  E1447  EEACELPECQEDAGNKVCSLQCNNHACGWDGGDCSLNFNDPWKN N1490
Mouse Notch1  E1446  EEACELPECQVDAGNKVCNLQCNNHACGWDGGDCSLNFNDPWKN N1489   LNR-A
Human Notch2  P1422  PATCLSQYCADKARDGVCDEACNSHACQWDGGDCSLTMENPWAN N1465
Mouse Notch2  P1420  PATCQSQYCADKARDGICDEACNSHACQWDGGDCSLTMEDPWAN N1463

Human Notch1  C1491  CTQSLQCWKYFSDGHCDSQCNSAGCLFDGFDCQRAEGQ Q1528
Mouse Notch1  C1490  CTQSLQCWKYFSDGHCDSQCNSAGCLFDGFDCQLTEGQ Q1527   LNR-B
Human Notch2  C1466  CSSPLPCWDY-INNQCDELCNTVECLFDNFECQGNSKT T1502
Mouse Notch2  C1464  CTSTLRCWEY-INNQCDEQCNTAECLFDNFECQRNSKT T1500

Human Notch1  C1529  CNPLYDQYCKDHFSDGHCDQGCNSAECEWDGLDC C1562
Mouse Notch1  C1528  CNPLYDQYCKDHFSDGHCDQGCNSAECEWDGLDC C1561   LNR-C
Human Notch2  C1503  CK--YDKYCADHFKDNHCDQGCNSEECGWDGLDC C1534
Mouse Notch2  C1501  CK--YDKYCADHFKDNHCDQGCNSEECGWDGLDC C1532

Human Notch1  A1563  A-EHVPERLAAGTLVVVVLMPPEQLRNSSFHFLRELSRVLHTNVVFKRDAHG
Mouse Notch1  A1562  A-EHVPERLAAGTLVLVVLLPPDQLRNNSFHFLRELSHVLHTNVVFKRDAQG
Human Notch2  A1535  AAD-QPENLAEGTLVIVVLMPPEQLLQDARSFLRALGTLLHTNLRIKRDSQG
Mouse Notch2  A1533  ASD-QPENLAEGTLIIVVLLPPEQLLQDSRSFLRALGTLLHTNLRIKQDSQG   HD-N
                     QQMIFPYYGREEELRKHPIKRAAEGWAAPDALLGQVKASLLPGGSEGGRRRR R1665
                     QQMIFPYYGHEEELRKHPIKRSTVGWAT---------SSLLPGTS-GGRQRR R1654
                     ELMVYPYYGEKSAAMKKQRM-----------------------------TRR R1608
                     ALMVYPYFGEKSAAMKKQKM-----------------------------TRR R1606

Human Notch1  E1666  -----ELDPMDVRGSIVYLEIDNRQCVQASSQCFQSATD-VAAFLGALASL-
Mouse Notch1  E1665  -----ELDPMDIRGSIVYLEIDNRQCVQSSSQCFQSATD-VAAFLGALASL-
Human Notch2  S1609  SLP--GEQEQEVAGSKVFLEIDNRQCVQDSDHCFKN-TDAAAALL-ASHAIQ
Mouse Notch2  S1607  SLPEEQEQEQEVIGSKIFLEIDNRQCVQDSDQCFKN-TDAAAALL-ASHAIQ   HD-C
                     GSLNIPYKIEAVQSETVEPPPPAQ Q1734
                     GSLNIPYKIEAVKSEPVEPPLPSQ Q1723
                     GTLSYP--LVSVVSESL-TPERTQ Q1677
                     GTLSYP--LVSVFSE-LESPRNAQ Q1677
                                ↑
                             S2─┘
```

FIG. 18

α-NRR1
α-NRR2
α-NRR1 + α-NRR2

Small Intestine
Large Intestine

ANTI-NOTCH2 NRR ANTIBODIES

CROSS REFERENCE TO RELATED APPLICATION

This application claims the benefit of U.S. Provisional Application No. 61/101,917, filed Oct. 1, 2008, the disclosure of which is incorporated herein by reference in its entirety.

FIELD OF THE INVENTION

The present invention relates generally to the field of molecular biology. More specifically, the invention concerns anti-Notch antibodies, including anti-Notch2 negative regulatory region (NRR) antibodies, and uses of the same. Anti-Notch1 NRR antibodies and methods of use are also provided.

BACKGROUND

The Notch receptor family is a class of evolutionarily conserved transmembrane receptors that transmit signals affecting development in organisms as diverse as sea urchins and humans. Notch receptors and their ligands, Delta and Serrate (known as Jagged in mammals), are transmembrane proteins with large extracellular domains that contain epidermal growth factor (EGF)-like repeats. The number of Notch paralogues differs between species. For example, there are four Notch receptors in mammals (Notch1-Notch4), two in *Caenorhabditis elegans* (LIN-12 and GLP-1) and one in *Drosophila melanogaster* (Notch). Notch receptors are proteolytically processed during transport to the cell surface by a furin-like protease at a site S1 on the N-terminal side of the transmembrane domain, producing an extracellular Notch (ECN) subunit and a Notch transmembrane subunit (NTM). These two subunits remain non-covalently associated and constitute the mature heterodimeric cell-surface receptor. Notch receptors and the Notch signaling pathway are reviewed, e.g., in Aster et al., *Annu. Rev. Pathol. Mech. Dis.* 3:587-613, 2008, and Bolos et al., *Endocrine Reviews* 28:339-363, 2007.

Notch2 ECN subunits contain 36 N-terminal EGF-like repeats followed by three tandemly repeated Lin 12/Notch Repeat (LNR) modules that precede the S1 site. Each LNR module contains three disulfide bonds and a group of conserved acidic and polar residues predicted to coordinate a calcium ion. Within the EGF repeat region lie binding sites for the activating ligands.

The Notch2 NTM comprises an extracellular region (which harbors the S2 cleavage site), a transmembrane segment (which harbors the S3 cleavage site), and a large intracellular portion that includes a RAM23 domain, six ankyrin repeats, a transactivation domain and a carboxy-terminal PEST sequence. Stable association of the ECN and NTM subunits is dependent on a heterodimerization domain (HD) comprising the carboxy-terminal end of the ECN (termed HD-N) and the extracellular amino-terminal end of NTM (termed HD-C). Before ligand-induced activation, Notch is maintained in a resting conformation by a negative regulatory region (NRR), which comprises the three LNRs and the HD domain. The crystal structure of the Notch2 NRR is reported in Gordon et al., (2007) *Nature Structural & Molecular Biology* 14:295-300, 2007.

Binding of a Notch ligand to the ECN subunit initiates two successive proteolytic cleavages that occur through regulated intramembrane proteolysis. The first cleavage by a metalloprotease (ADAM17) at site S2 renders the Notch transmembrane subunit susceptible to a second cleavage at site S3 close to the inner leaflet of the plasma membrane. Site S3 cleavage, which is catalyzed by a multiprotein complex containing presenilin and nicastrin and promoting γ-secretase activity, liberates the intracellular portion of the Notch transmembrane subunit, allowing it to translocate to the nucleus and activate transcription of target genes. (For review of the proteolytic cleavage of Notch, see, e.g., Sisodia et al., *Nat. Rev. Neurosci.* 3:281-290, 2002.)

Five Notch ligands of the Jagged and Delta-like classes have been identified in humans (Jagged1 (also termed Serrate1), Jagged2 (also termed Serrate2), Delta-like1 (also termed DLL1), Delta-like3 (also termed DLL3), and Delta-like4 (also termed DLL4)). Each of the ligands is a single-pass transmembrane protein with a conserved N-terminal Delta, Serrate, LAG-2 (DSL) motif essential for binding Notch. A series of EGF-like modules C-terminal to the DSL motif precede the membrane-spanning segment. Unlike the Notch receptors, the ligands have short cytoplasmic tails of 70-215 amino acids at the C-terminus. In addition, other types of ligands have been reported (e.g., DNER, NB3, and F3/Contactin). (For review of Notch ligands and ligand-mediated Notch activation, see, e.g., D'Souza et al., *Oncogene* 27:5148-5167, 2008.)

The Notch pathway functions during diverse developmental and physiological processes including those affecting neurogenesis in flies and vertebrates. In general, Notch signaling is involved in lateral inhibition, lineage decisions, and the establishment of boundaries between groups of cells (see, e.g., Bray, *Molecular Cell Biology* 7:678-679, 2006). A variety of human diseases, including cancers and neurodegenerative disorders, have been shown to result from mutations in genes encoding Notch receptors or their ligands (see, e.g., Nam et al., *Curr. Opin. Chem. Biol.* 6:501-509, 2002). The connection between unrestrained Notch signaling and malignancy was first recognized when a recurrent t(7;9)(q34;q34.3) chromosomal translocation which creates a truncated, constitutively active variant of human Notch1 was identified in a subset of human acute lymphoblastic leukemias (T-ALL) (see, e.g., Aster et al., *Annu. Rev. Pathol. Mech. Dis.* 3:587-613, 2008). In mouse models, Notch1 signaling has been shown to be essential for T cell development and that Notch1-mediated signals promote T cell development at the expense of B cell development (see, e.g., Wilson et al., *J. Exp. Med.* 194:1003-1012, 2001).

Notch2 is also involved in certain cancers. Particularly, Notch2 is overexpressed in B-cell chronic lymphocytic leukemia (B-CLL), which in turn leads to overexpression of CD23, a hallmark of B-CLL cells. (See Hubmann et al., *Blood* 99:3742-3747, 2002.) Both Notch1 and Notch2 are highly expressed in multiple myeloma cells (cancerous plasma B cells), and stimulation with ligand strongly increases tumor cell growth. (See Jundt et al., *Blood* 103:3511-3515, 2004.) Notch2 and downstream effectors are overexpressed in melanoma (see Hoek et al., *Cancer Res.* 64:5270-5282, 2004; Seykora et al., *Am J Dermatopathol* 25:6-11, 2003), and the Notch2 locus is recurrently amplified in melanoma cell lines (Jonsson et al., *Oncogene,* 26:4738-4748, 2007). In addition, numerous studies have linked aberrant Notch2 signaling to breast cancer and other solid tumors (reviewed by Leong and Karsay, *Blood* 107:2223-2233, 2006). Notch2 is also required for marginal zone B cell development. (See Pillai et al., *Annu. Rev. Immunol.* 23:161-196, 2005.)

Given the involvement of Notch signaling in a wide variety of human diseases it is clear that there continues to be a need for agents that regulate Notch signaling and that have clinical attributes that are favorable for development as therapeutic agents. The invention described herein meets this need and provides other benefits.

All references cited herein, including patent applications and publications, are incorporated by reference in their entirety.

SUMMARY

The invention provides anti-Notch antibodies and methods of using the same.

In one aspect, a monoclonal antibody that binds to Notch2 NRR is provided. In one embodiment, the antibody inhibits Notch2 activity. In another embodiment, the antibody does not significantly bind to a Notch family member other than Notch2. In another embodiment, the antibody binds to mouse Notch2 NRR and human Notch2 NRR. In another embodiment, the antibody binds to a Notch2 NRR with a Kd of ≦10 nM.

In a further embodiment, a monoclonal antibody that binds to Notch2 NRR is provided, wherein the antibody comprises:

(a) an HVR-H1 comprising an amino acid sequence that conforms to the consensus sequence of SEQ ID NO:3;

(b) an HVR-H2 comprising the amino acid sequence of SEQ ID NO:4;

(c) an HVR-H3 comprising the amino acid sequence of SEQ ID NO:5;

(d) an HVR-L1 comprising an amino acid sequence that conforms to the consensus sequence of SEQ ID NO:10;

(e) an HVR-L2 comprising an amino acid sequence that conforms to the consensus sequence of SEQ ID NO:14; and (f) an HVR-L3 comprising an amino acid sequence that conforms to the consensus sequence of SEQ ID NO:19.

In one such embodiment, the antibody comprises an HVR-H1 comprising an amino acid sequence selected from SEQ ID NOs:1-; an HVR-L1 comprising an amino acid sequence selected from SEQ ID NOs:6-9; an HVR-L2 comprising an amino acid sequence selected from SEQ ID NOs:11-13; and an HVR-L3 comprising an amino acid sequence selected from SEQ ID NOs:15-18. In one such embodiment, the HVR-H1 comprises the amino acid sequence of SEQ ID NO:1, the HVR-L1 comprises the amino acid sequence of SEQ ID NO:6, the HVR-L2 comprises the amino acid sequence of SEQ ID NO:11, and the HVR-L3 comprises the amino acid sequence of SEQ ID NO:15. In another such embodiment, the HVR-H1 comprises the amino acid sequence of SEQ ID NO:2, the HVR-L1 comprises the amino acid sequence of SEQ ID NO:7, the HVR-L2 comprises the amino acid sequence of SEQ ID NO:11, and the HVR-L3 comprises the amino acid sequence of SEQ ID NO:16. In another such embodiment, the HVR-H1 comprises the amino acid sequence of SEQ ID NO:2, the HVR-L1 comprises the amino acid sequence of SEQ ID NO:8, the HVR-L2 comprises the amino acid sequence of SEQ ID NO:12, and the HVR-L3 comprises the amino acid sequence of SEQ ID NO:17. In another such embodiment, the HVR-H1 comprises the amino acid sequence of SEQ ID NO:2, the HVR-L1 comprises the amino acid sequence of SEQ ID NO:9, the HVR-Lcomprises the amino acid sequence of SEQ ID NO:13, and the HVR-L3 comprises the amino acid sequence of SEQ ID NO:18. In any of the above embodiments, the antibody further comprises at least one framework selected from a human VH Acceptor 2 framework and a human VL kappa subgroup I consensus framework.

In another aspect, a monoclonal antibody that binds to Notch2 NRR is provided, wherein the antibody comprises a heavy chain variable domain having at least 90% sequence identity to an amino acid sequence selected from SEQ ID NO:20-21 and a light chain variable domain having at least 90% sequence identity to an amino acid sequence selected from SEQ ID NO:22-25. In one embodiment, the antibody comprises a heavy chain variable domain having at least 90% sequence identity to the amino acid sequence of SEQ ID NO:20 and a light chain variable domain having at least 90% sequence identity to the amino acid sequence of SEQ ID NO:22. In one such embodiment, the heavy chain variable domain comprises the amino acid sequence of SEQ ID NO:20, and the light chain variable domain comprises the amino acid sequence of SEQ ID NO:22. In another embodiment, the antibody comprises a heavy chain variable domain having at least 90% sequence identity to the amino acid sequence of SEQ ID NO:21 and a light chain variable domain having at least 90% sequence identity to an amino acid sequence selected from SEQ ID NOs:23-25. In one such embodiment, the heavy chain variable domain comprises the amino acid sequence of SEQ ID NO:21, and the light chain variable domain comprises an amino acid sequence selected from SEQ ID NOs:23-25.

In another aspect, an isolated antibody is provided that binds to the same epitope as an antibody selected from Antibody D, Antibody D-1, Antibody D-2, or Antibody D-3. In another aspect, an isolated antibody is provided that binds to the LNR-A domain and the HD-C domain of Notch2.

In another aspect, an anti-Notch2 NRR antibody is an antibody fragment selected from a Fab, Fab'-SH, Fv, scFv, or $(Fab')_2$ fragment. In another aspect, an anti-Notch2 NRR antibody is a humanized, chimeric, or human antibody.'

Any of the above embodiments may be present singly or in combination.

In another aspect, a method of inhibiting Notch2 activity is provided, the method comprising exposing a cell that expresses Notch2 to an antibody as in any of the above embodiments. In another aspect, a method of treating a disorder associated with increased expression or activity of Notch2 is provided, the method comprising administering to a subject in need thereof an effective amount of an antibody as in any of the above embodiments. In another aspect, a method of treating a B-cell malignancy is provided, the method comprising administering to a subject in need thereof an effective amount of an antibody as in any of the above embodiments. In another aspect, a method of treating melanoma is provided, the method comprising administering to a subject in need thereof an effective amount of an antibody as in any of the above embodiments.

In another aspect, a method of treating a disorder associated with increased expression or activity of Notch1 is provided, the method comprising coadministering to a subject in need thereof an effective amount of an anti-Notch1 NRR antibody and a therapeutic agent selected from dexamethasone and tamoxifen, wherein the therapeutic agent reduces altered intestinal cell differentiation caused by the antibody. In one such embodiment, the disorder is a T-cell malignancy.

BRIEF DESCRIPTION OF THE FIGURES

FIG. 1 shows the H1, H2, and H3 heavy chain hypervariable region (HVR) sequences of anti-Notch2 NRR monoclonal antibodies designated Antibody D, Antibody D-1, Antibody D-2, and Antibody D-3, as described in Example B(1). Amino acid positions are numbered according to the Kabat numbering system as described below.

FIG. 2 shows the L1, L2, and L3 light chain HVR sequences of anti-Notch2 NRR monoclonal antibodies designated Antibody D, Antibody D-1, Antibody D-2, and Antibody D-3, as described in Example B(1). Amino acid positions are numbered according to the Kabat numbering system as described below.

FIG. 3 shows an alignment of the heavy chain variable region sequences of Antibody D, Antibody D-1, Antibody D-2, and Antibody D-3. HVRs are enclosed in boxes, as described in Example B(1).

FIG. 4 shows an alignment of the light chain variable region sequences of Antibody D, Antibody D-1, Antibody D-2, and Antibody D-3. HVRs are enclosed in boxes.

FIGS. 5A and 5B show exemplary acceptor human variable heavy (VH) consensus framework sequences for use in practicing the instant invention. Sequence identifiers are as follows:

- human VH subgroup I consensus framework "A" minus Kabat CDRs (SEQ ID NOs:32, 33, 34, 35).
- human VH subgroup I consensus frameworks "B," "C," and "D" minus extended hypervariable regions (SEQ ID NOs:36, 37, 34, 35; SEQ ID NOs:36, 37, 38, 35; and SEQ ID NOs:36, 37, 39, 35).
- human VH subgroup II consensus framework "A" minus Kabat CDRs (SEQ ID NOs:40, 41, 42, 35).
- human VH subgroup II consensus frameworks "B," "C," and "D" minus extended hypervariable regions (SEQ ID NOs:43, 44, 42, 35; SEQ ID NOs:43, 44, 45, 35; and SEQ ID NOs:43, 44, 46, and 35).
- human VH subgroup III consensus framework "A" minus Kabat CDRs (SEQ ID NOs:47, 48, 49, 35).
- human VH subgroup III consensus frameworks "B," "C," and "D" minus extended hypervariable regions (SEQ ID NOs:50, 51, 49, 35; SEQ ID NOs:50, 51, 52, 35; and SEQ ID NOs:50, 51, 53, 35).
- human VH acceptor framework "A" minus Kabat CDRs (SEQ ID NOs:54, 48, 55, 35).
- human VH acceptor frameworks "B" and "C" minus extended hypervariable regions (SEQ ID NOs:50, 51, 55, 35; and SEQ ID NOs:50, 51, 56, 35).
- human VH acceptor 2 framework "A" minus Kabat CDRs (SEQ ID NOs:54, 48, 57, 35).
- human VH acceptor 2 framework "B," "C," and "D" minus extended hypervariable regions (SEQ ID NOs:50, 51, 57, 35; SEQ ID NOs:50, 51, 58, 35; and SEQ ID NOs: 50, 51, 59, 35).

FIG. 6 shows exemplary acceptor human variable light (VL) consensus framework sequences for use in practicing the instant invention. Sequence identifiers are as follows:

- human VL kappa subgroup I consensus framework (κv1): SEQ ID NOs:60, 61, 62, 63
- human VL kappa subgroup II consensus framework (κv2): SEQ ID NOs:64, 65, 66, 63
- human VL kappa subgroup III consensus framework (κv3): SEQ ID NOs:67, 68, 69, 63
- human VL kappa subgroup IV consensus framework (κv4): SEQ ID NOs:70, 71, 72, 63

FIG. 7 shows framework sequences of huMAb4D5-8 light and heavy chains. Numbers in superscript/bold indicate amino acid positions according to Kabat.

FIG. 8 shows framework sequences of huMAb4D5-8 light and heavy chains with the indicated modifications. Numbers in superscript/bold indicate amino acid positions according to Kabat.

Figure 9A:
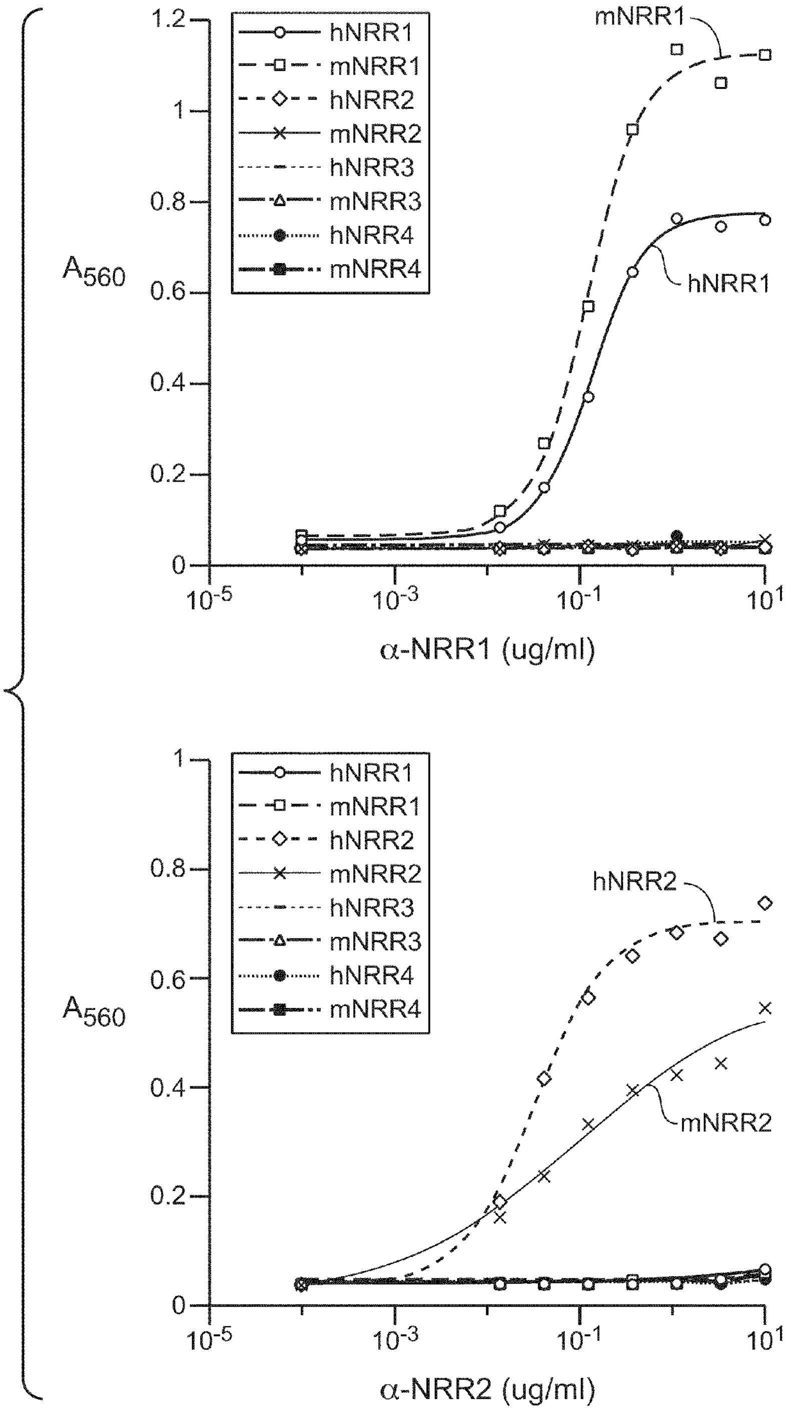
Figure 9B:
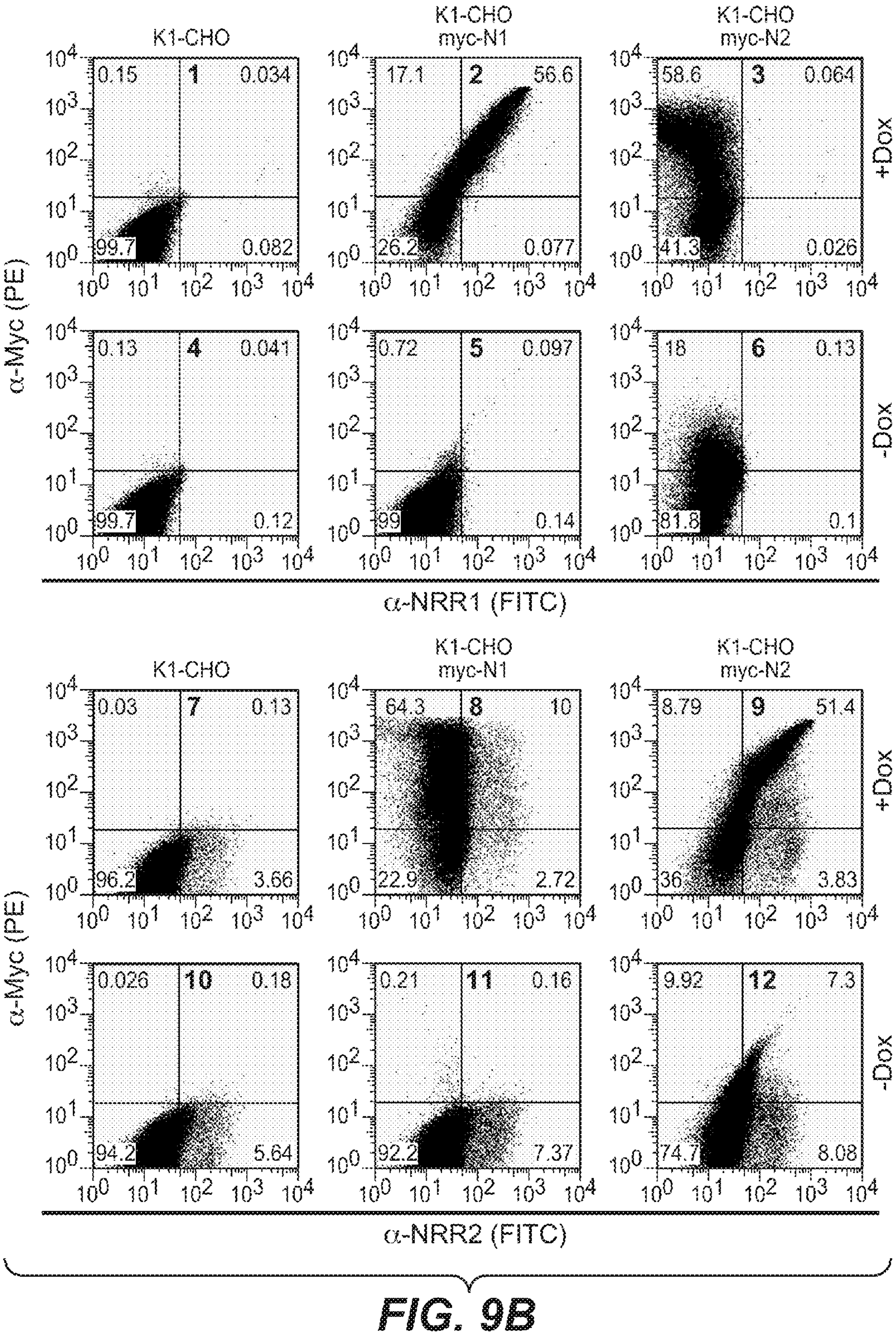

FIGS. 9A and 9B show that anti-NRR1 and anti-NRR2 antibodies bind specifically to their cognate receptors, as described in Example B(1). (A) ELISA assay measuring binding of anti-NRR1 (left panel) and anti-NRR2 (right panel) to purified NRR protein fragments from each of the four human (h) and murine (m) Notch receptors. Binding, depicted as $A_{560}$ on the y-axis is graphed vs. a titration of anti-NRR1 or anti-NRR2. (B) FACS assay measuring binding of anti-NRR1 (panels 1-6) or anti-NRR2 (panels 7-12) to untransfected K1-CHO cells (panels 1, 4, 7 and 10), K1-CHO cells stably transfected with N-myc-Notch1 (panels 2, 5, 8 ad 11) or K1-CHO cells stably transfected with N-myc-Notch2 (panels 3, 6, 9 and 12). The N-myc-Notch transgenes were expressed under control of the inducible tet promoter; bottom row, control expression in the absence of induction with doxycycline (−Dox); top row, induced expression following addition of doxycycline (+Dox); note that the K1-CHO line endogenously expresses Notch2, which is detected by anti-NRR2 in the presence and absence of doxycycline (for example, compare panels 7 and 10).

Figure 10A:
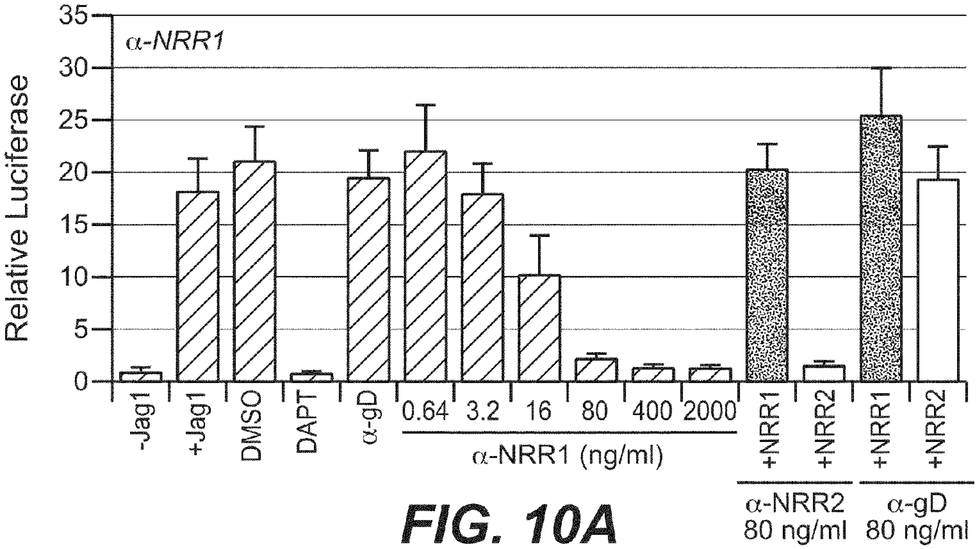
Figure 10B:
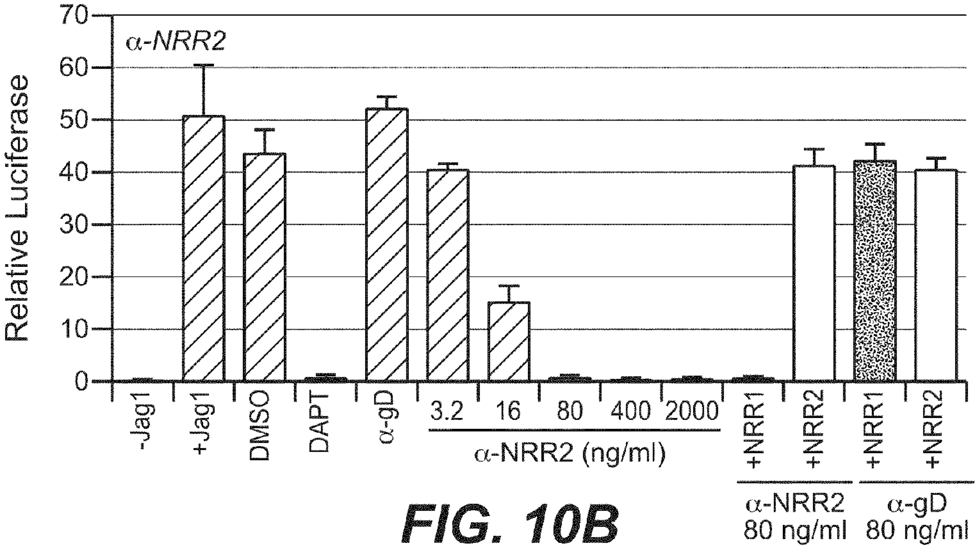
Figure 10C:
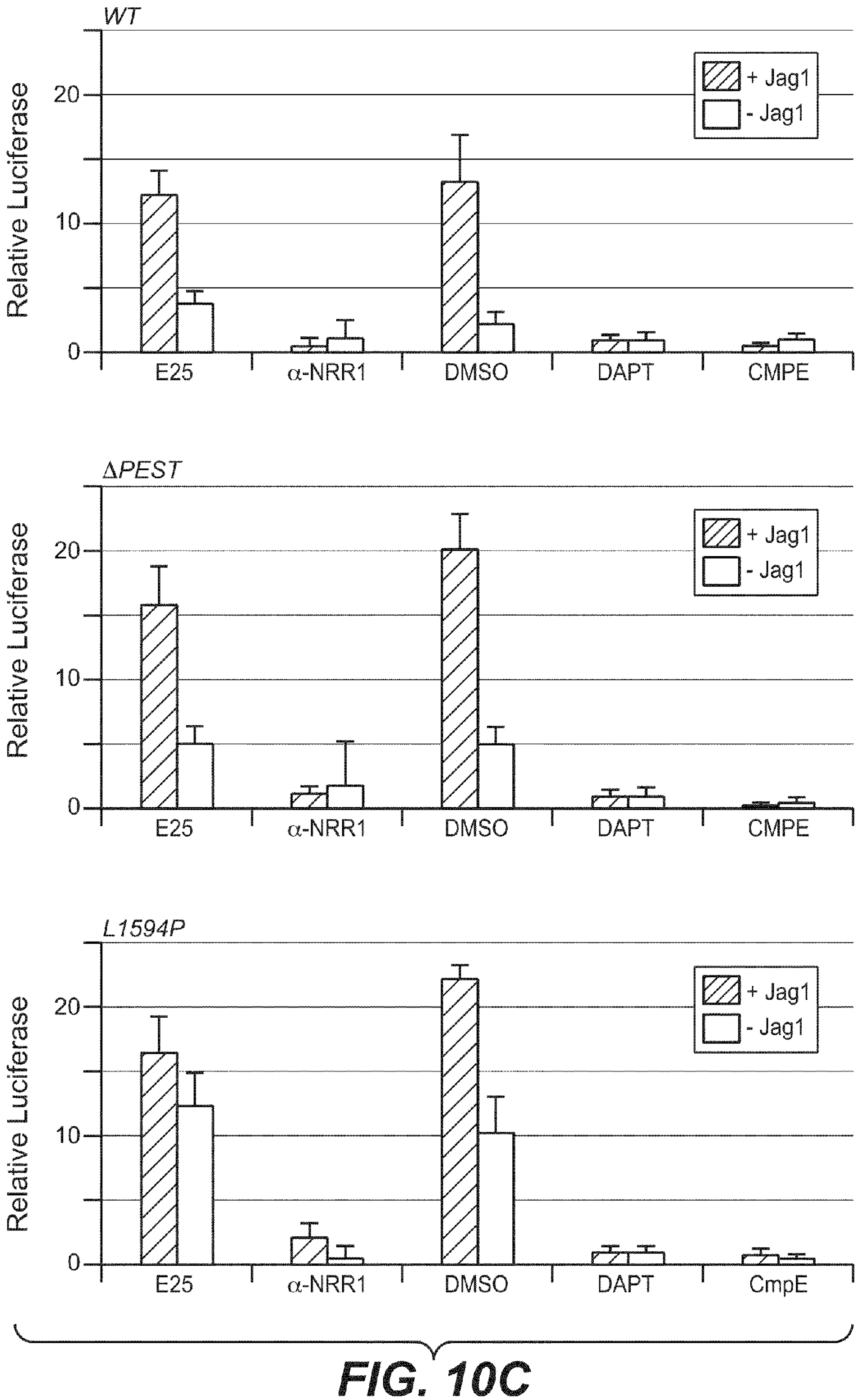

FIGS. 10A-C show that anti-NRR1 and anti-NRR2 specifically inhibit signaling from their targeted receptors, including receptors carrying activating mutations, as described in Examples B(2) and B(3). (A) Co-culture assay measuring anti-NRR1 inhibition of Notch1 signaling. NIH-3T3 cells stably transfected with Jag1 were used to induce Notch signaling in NIH-3T3 cells stably transfected with Notch1 (except for "−Jag1", which used untransfected NIH-3T3 cells in place of the Jag1-expressing cells). Notch signaling was measured using a Notch reporter gene (CSL-dependent promoter driving expression of firefly luciferase) and is expressed relative to control gene expression (constitutive promoter driving expression of *Renilla luciferase*) normalized to the DAPT conditions (defined as a value of 1). +Jag1, standard co-culture assay; DMSO, DAPT vehicle alone; DAPT, 5 μM in DMSO; α-gD, isotype control antibody at 2000 ng/ml; α-NRR1, anti-NRR1 antibody at the indicated concentrations; the last four assays included 80 ng/ml of either α-NRR1 or α-gD plus either purified Notch1 or Notch2 NRR protein fragments, as indicated (+NRR1 or +NRR2). (B) Co-culture assay measuring anti-NRR2 inhibition of Notch2 signaling. NIH-3T3 cells stably transfected with Jag1 were used to induce Notch signaling in U87MG cells, which express high levels of Notch2. The assay was performed as described in (A). (C) Co-culture assay measuring anti-NRR1 inhibition of Notch1 signaling from wild-type or mutant Notch1 receptors. The assay was performed as in (A) except that the receptor-expressing cells were generated by transient transfection of plasmids expressing the indicated Notch1 receptors. WT, wild-type Notch1; ΔPEST, Notch1 lacking the PEST domain; L1594P, Notch1 carrying the indicated constitutively-activating point mutation; E25, 625 ng/ml isotype control antibody; α-NRR1, 625 ng/ml anti-NRR1 antibody; DMSO, GSI vehicle alone; DAPT, 5 μM in DMSO; CmpE, 1 μM compound E in DMSO.

FIGS. 11A-D show that anti-NRR1 and anti-NRR2 function as receptor-specific inhibitors in vivo, as described in Example B(4). Balb/c mice were injected four times every four days with 5 mg/kg of α-gD isotype control, α-NRR1 or α-NRR2, and cells were harvested from the thymus or spleen on day 13, one day after the fourth dose. (A) Thymus weight measurements. Thymus weights (in mg) are expressed relative to total body weight (in g). Values represent the mean plus standard deviation for three mice per group. (B) Thymus cell count. (C) CD4 and CD8 FACS to identify $CD4^+/CD8^+$ double-positive T cells. Numbers represent the percentage of thymic cells in the double-negative, single-positive and double-positive populations. Relative to the anti-gD control (77.5%), anti-NRR1 dramatically reduced the percentage of cells in the $CD4^+/CD8^+$ population (5.89%) whereas anti-NRR2 (80%) had no significant effect. (D) CD21 and CD23 FACS to identify marginal zone B cells. Numbers represent the mean percentages ±standard deviation (from three animals) of cells within the MZB gate, which is boxed; p values are also noted; representative dot plots from one of the three animals in each group are graphed. Relative to the anti-gD control (6.61%), anti-NRR2 nearly eliminated MZB cells (0.97%) whereas anti-NRR1 (6%) had no significant effect.

In FIGS. 12A-D, a 2.2 Å structure of anti-NRR1 Fab/NRR1 co-crystal indicates that anti-NRR1 simultaneously contacts the LNR-A, LNR-B and HD-C domains, as described in Example B(5). (A) Table summarizing the binding of α-NRR1 or α-NRR2 to Notch1-NRR or Notch2 NRR chimeric protein fragments. The indicated NRR protein fragments (dark blue, Notch1 sequences; light blue, Notch2 sequences) were expressed as secreted proteins fused to alkaline phosphatase to enable rapid measurements of antibody binding in a plate-based assay. After using alkaline phosphatase activity to normalize for NRR expression and secretion, culture medium containing the indicated NRR chimeric proteins was added to a 96-well plate that had been coated with α-NRR1, α-NRR2 or an isotype control antibody (used to assess background binding, not shown). Antibody binding was assessed by measuring alkaline phosphatase activity that remained bound to the plate. Y, strong binding; N, no binding observed; W, weak binding observed. (B) Structure of human Notch NRR1. NRR1 is shown as a C-alpha cartoon. The three calcium ions in the LNR motifs are shown as spheres. The position of the S2 cleavage site is marked with an arrow. (C) Superposition of NRR1 on NRR2 (chain A from pdb code 2OO4) based on structurally conserved atoms. NRR1 (shaded) and NRR2 (white) are shown as C-alpha traces. (D) Open-book view of the interface between NRR1 (left) and α-NRR1 Fab (right, border between heavy and light chains shown as a black dashed line). The extent to which the solvent accessible surface area is buried by complex formation is indicated. Residues that are buried by at least 50% are labeled, with identical NRR residues in Notch1 and Notch2 labeled in black font (see also FIG. 18).

Figure 13A:
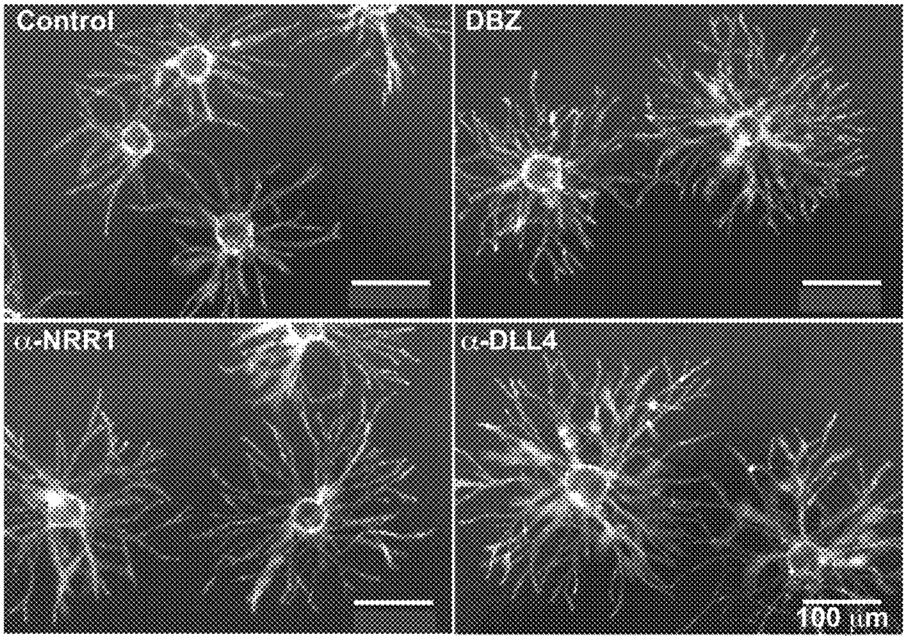
Figure 13B:
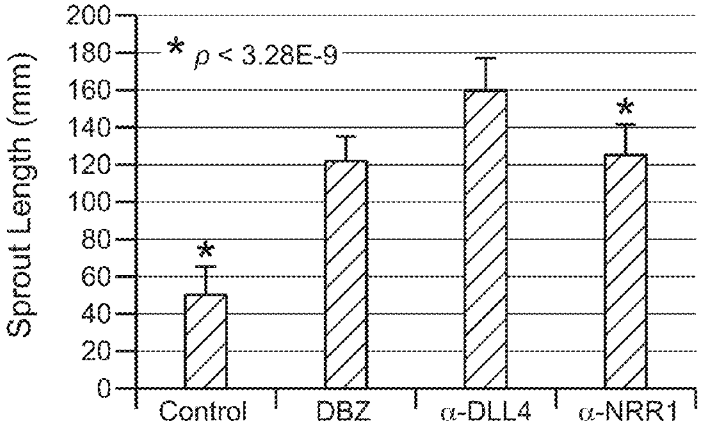
Figure 13C:
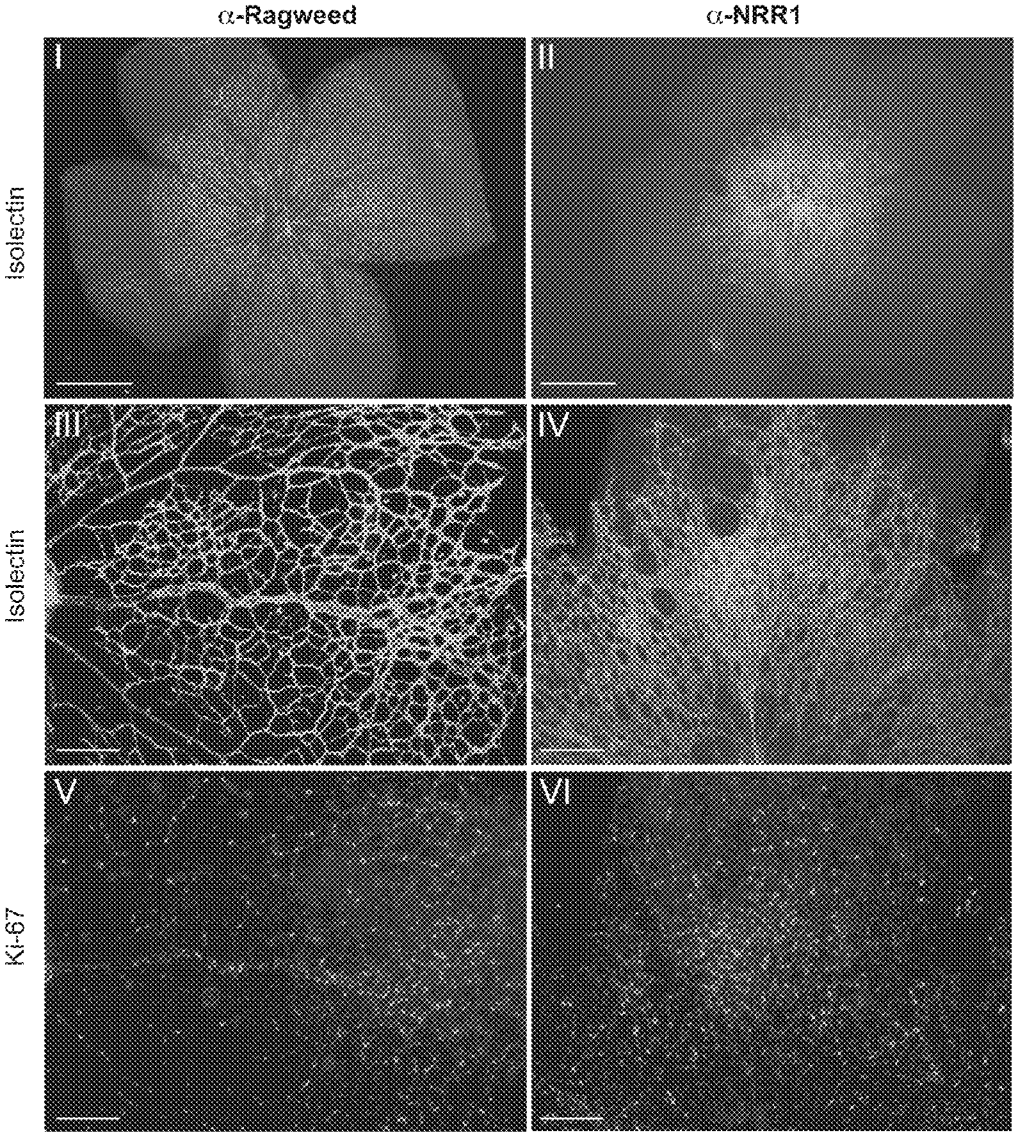

FIGS. 13A-C show that anti-NRR1 causes endothelial cell hypersprouting, as described in Example B(6). (A) In vitro endothelial cell sprouting assay. HUVECs were coated on Cytodex beads and co-cultured with skin fibroblasts. Cultures were either mock treated (control) or treated with 1 μM of DBZ, 5 μg/ml of α-NRR1 or 5 μg/ml of α-D114. Bar=100 μm. (B) Sprout length measurements from the cultures in (A). (C) Mouse neonate retinal assay for endothelial cell sprouting and angiogenesis. Mouse neonates were injected at P1 and P3 with the indicated antibodies, and retinas were prepared at P5 to visualize perfusion of isolectin or the Ki67 marker for proliferation. Panels I and II, Bar=1 mm. Panels III-VI represent enlargements of part of panels I and II, bar=0.2 mm.

FIGS. 14A-E show that selective antibody blocking of Notch1 signaling disrupts tumor angiogenesis and inhibits tumor growth, as described in Example B(7). Graphs for three tumor xenograft models showing tumor volume (mean+/−SEM) versus time following treatment with the indicated antibodies: α-Ragweed (negative control), α-VEGF or α-NRR1. P values are shown for the α-Ragweed vs. α-NRR1 comparison. (A) Calu6 model. (B) HM7 model. (C) HM7 model with dose titration of α-NRR1. (D) Endothelial cell staining in representative tumor sections from the Calu6 model shown in (A). The antibodies used in the xenograft model are shown at the top. DAPI and α-CD31 were used to stain DNA and endothelial cells, respectively. The bottom row of panels shows the merged images. Bar=50 μm. (E) Quantification of the CD31 staining shown in (D). Using ImageJ to quantify the CD31 and DAPI staining in images similar to those shown in (D), relative CD31 staining (CD31 staining normalized to DAPI staining) was graphed for each of the three antibody treatments relative to the α-Ragweed control, which was set to a value of 1; data represent the mean+/−standard deviation over 8 image fields.

Figure 15A:
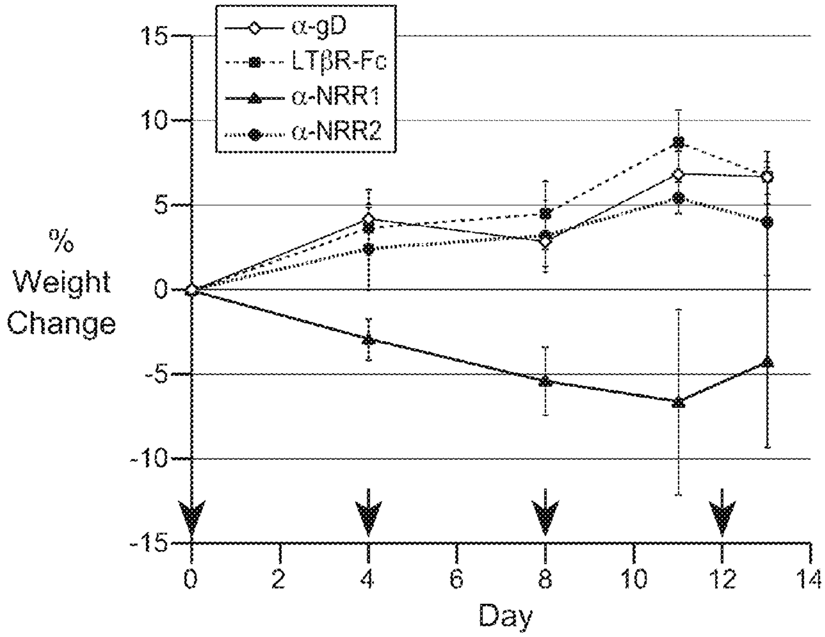
Figure 15C:
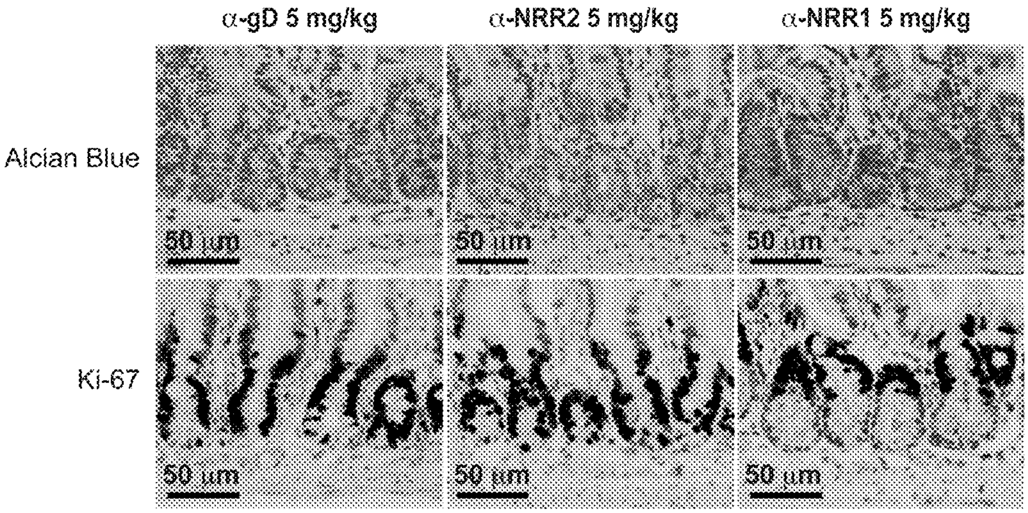
Figure 15B:
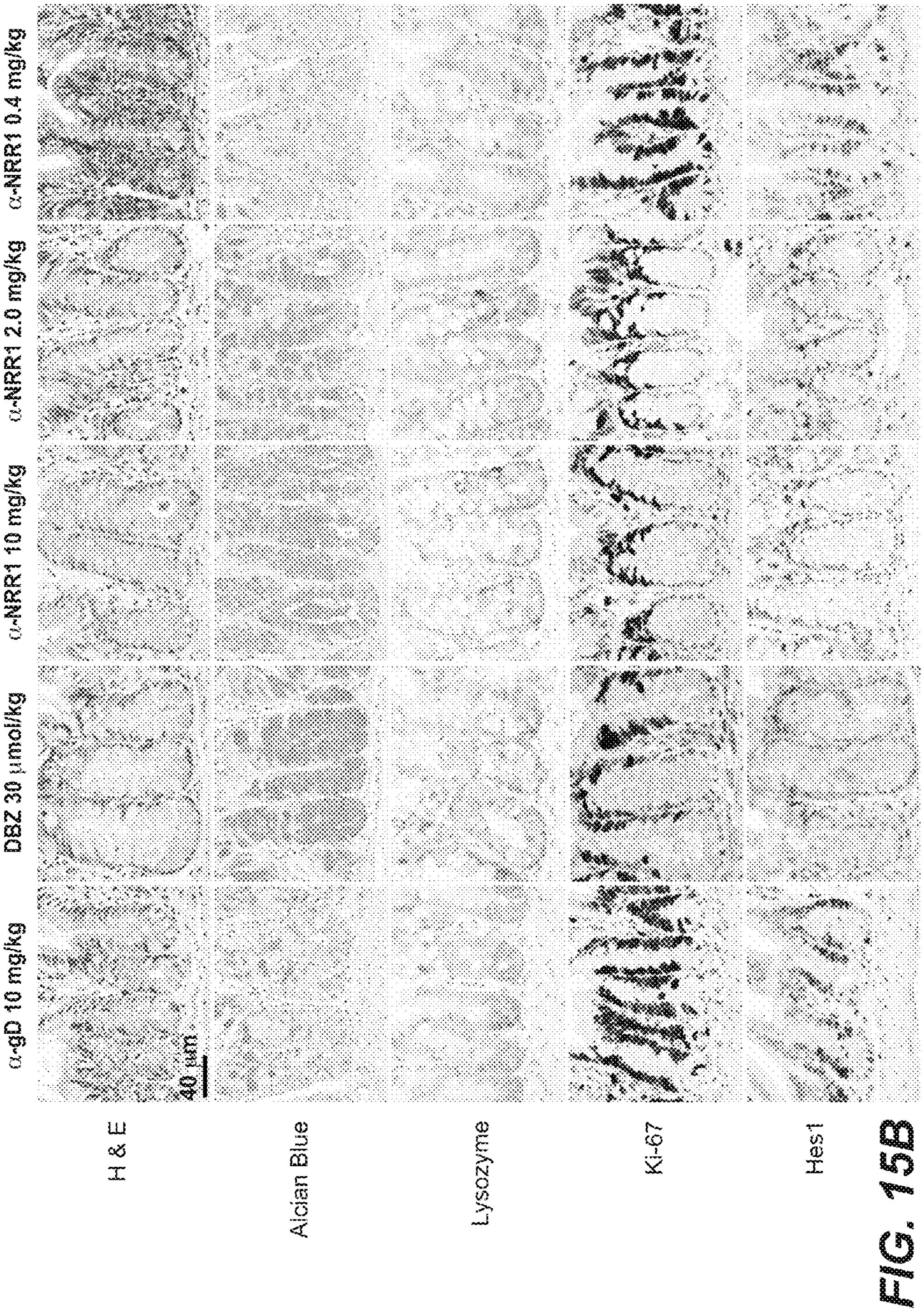

FIGS. 15A-C show that selective antibody blocking of Notch1 is sufficient to alter cell fate in the small intestine, as described in Example B(8). (A) Total body weight change (mean+/−standard deviation) vs. time. Mice were treated as described for FIG. 11 with anti-gD isotype control, LTβR-Fc, anti-NRR1 or anti-NRR2. Arrows mark the days of dosing. (B) Immunohistochemical analyses of small intestines. Mice were treated with the indicated concentrations of anti-gD isotype control, DBZ or anti-NRR1 on days 0, 2 and 6, and small intestines were prepared for immunohistochemical analyses on day 7. In each row as indicated, staining is shown for haemotoxylin and eosin (H & E), Alcian Blue for mucin and to mark secretory goblet cells, lysozyme to mark Paneth cells, Ki-67 for proliferation and Hes1 as a Notch downstream target. See FIGS. 19 and 20 for analyses of the large intestine at day 7 and of the small intestine at day 2, respectively. Bar=40 μm. (C) Comparison of Notch1- versus Notch2-specific inhibition on small intestinal cell differentiation. Small intestines from the study described in (A) were prepared for Alcian Blue and Ki-67 one day after the final dosing with α-gD, α-NRR1 or α-NRR2, as indicated. Bar=50 μm.

Figure 16:
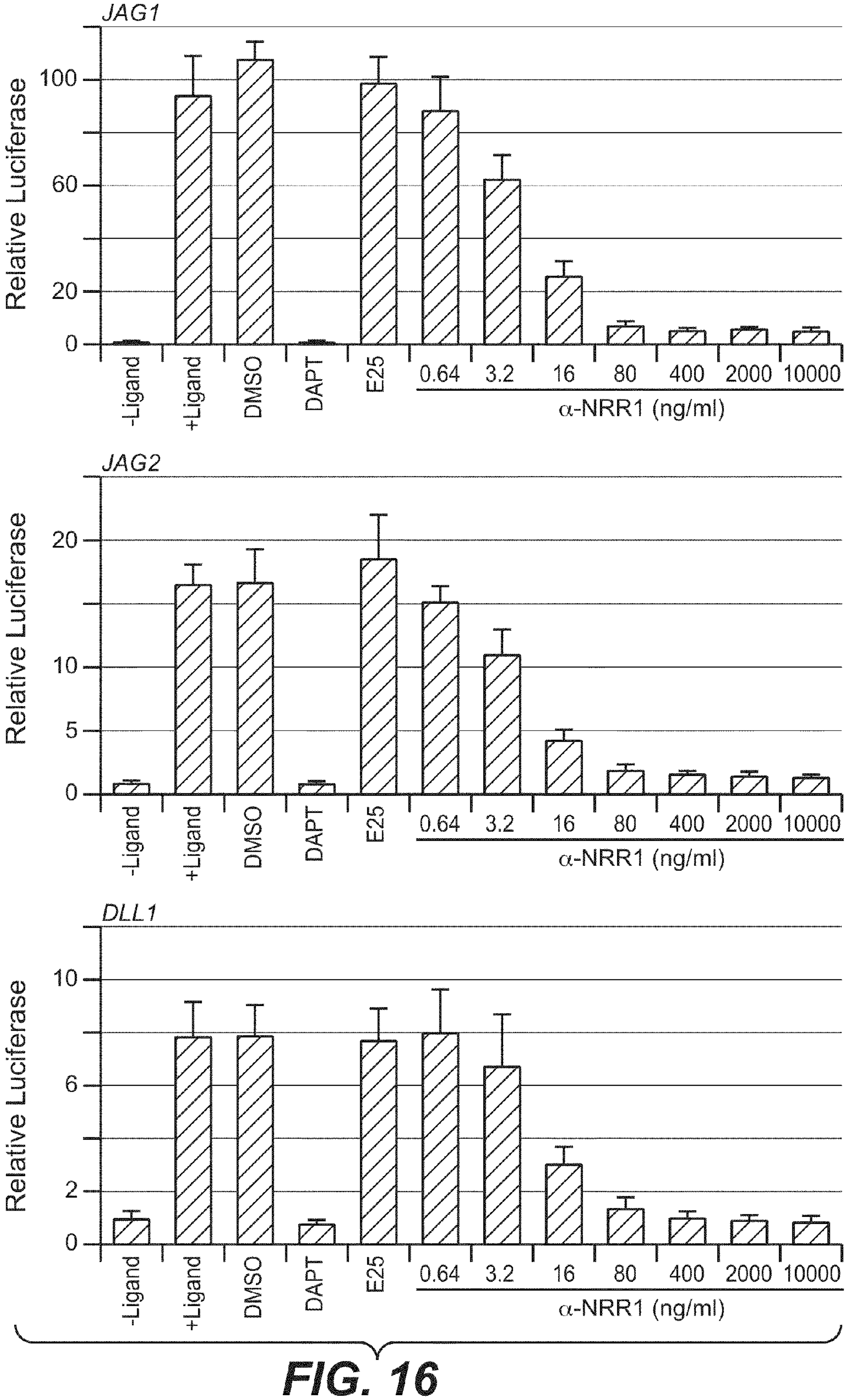

FIG. 16 shows that anti-NRR1 is a potent inhibitor of Notch1 signaling induced by multiple ligands, as described in Example B(2). Co-culture assays of Notch1 signaling were performed as described in FIG. 10A except that the ligand-expressing cells expressed Jag1, Jag2 or D111, as indicated.

FIG. 17 shows low-yield Notch1 NRR/Notch2 NRR chimeric protein constructs, as described in Example B(5). The table supplements FIG. 12A, listing the NRR chimeric proteins that yielded little or no secreted alkaline phosphatase activity, suggesting that the chimeras were misfolded or otherwise unstable. For those fragments that yielded weak but detectable alkaline phosphatase activity, the binding of α-NRR1 or α-NRR2 is summarized. —no expression and binding not testable; N, no expression or binding; W, weak expression or binding.

FIG. 18 shows conservation of NRR1 residues contacted by anti-NRR1, as described in Example B(1) and B(5). Amino acid sequence alignment of the human Notch1 NRR domain (SEQ ID NO:26), mouse Notch1 NRR domain (SEQ ID NO:27), human Notch2 NRR domain (SEQ ID NO:28) and mouse Notch2 NRR domain (SEQ ID NO:29), with the sub-domain boundaries shown at the right. Human Notch1 NRR is listed as the reference sequence, and residues in the other NRR sequences that are identical to those in human Notch1 are shown in bold font. Residues that are at least 25% buried in the anti-NRR1-Fab/Notch1-NRR structure (FIG. 12) are outlined, with solid lines versus dashed lines reflecting an increased degree to which the residues are buried. Of the 21 amino acids that are at least 25% buried in the human Notch1 sequence, all 21 are identical in the mouse Notch1 sequence but only six are identical in the human and mouse Notch2 sequences (plus a seventh conservative difference of T in place of S at human Notch1 S1712); of these identical and "buried" residues in the Notch2 sequences, none are in the class of >75% buried. This sequence comparison is consistent with (a) strong anti-NRR1 binding (approximately equal affinities) to both human and mouse Notch1 and (b) a lack of anti-NRR1 binding to human and mouse Notch2. Moreover, the buried residues all lay within the LNR-A, LNR-B and HD-C, consistent with the domain swap experiment shown in FIGS. 11A and 17.

Figure 19:
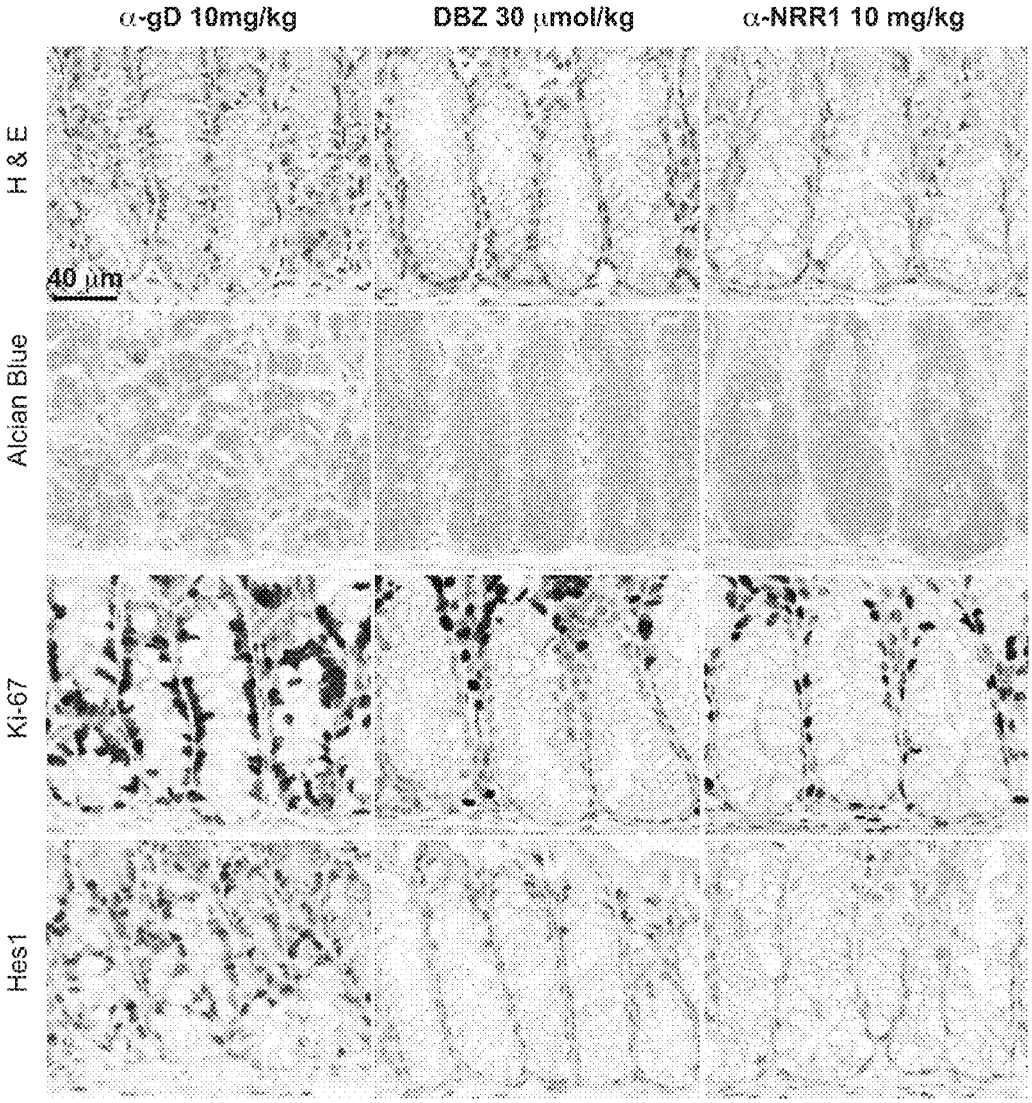

FIG. 19 shows that selective antibody blocking of Notch1 is sufficient to alter cell fate in the large intestine, as described in Example B(8). Histopathological analyses of large intestine samples taken at day 7 from the experiment described in FIG. 15B.

Figure 20:
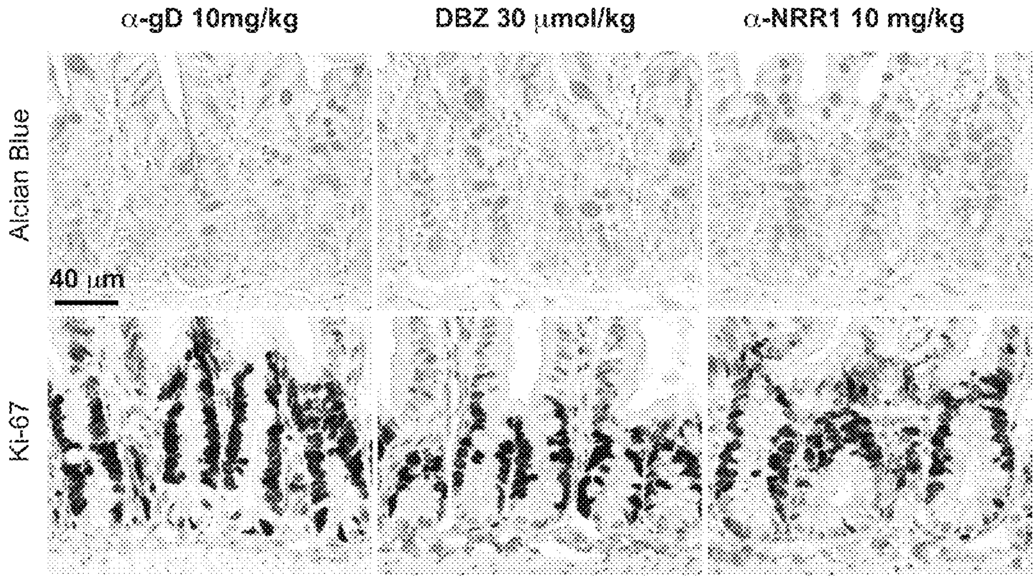

FIG. 20 shows that intestinal cell fate changes develop 2 days after blocking Notch1, as described in Example B(8). Histopathological analyses of small intestine samples taken at day 2 from the experiment described in FIG. 15B, which shows samples taken at day 7.

Figure 11A:
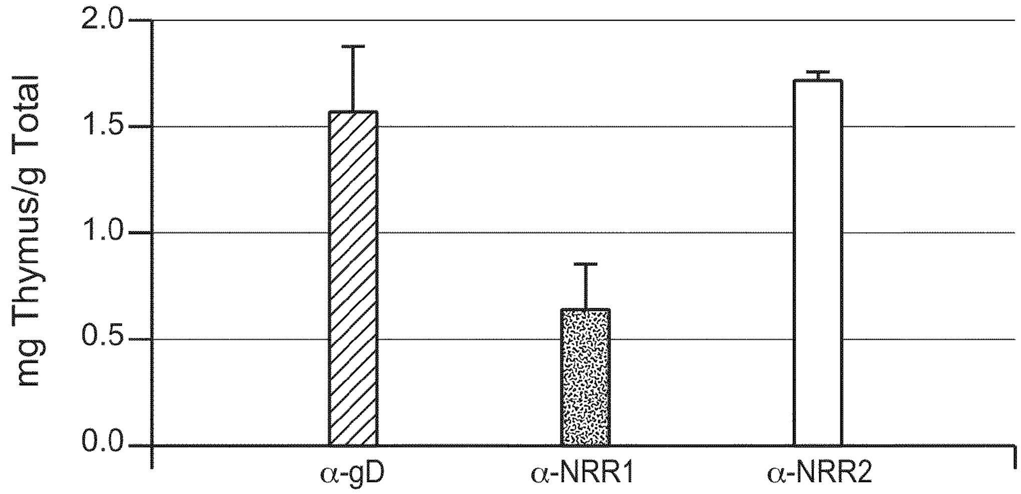
Figure 11B:
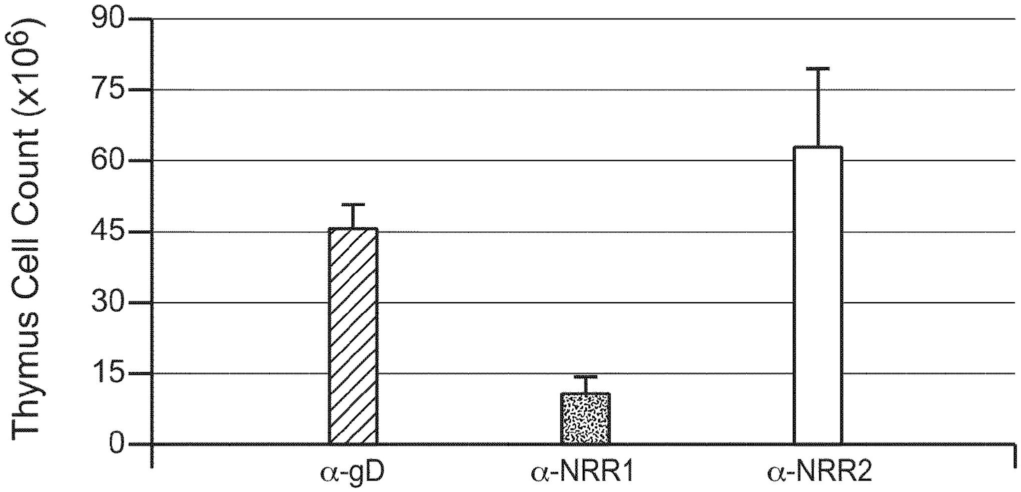
Figures 11C, 11D:
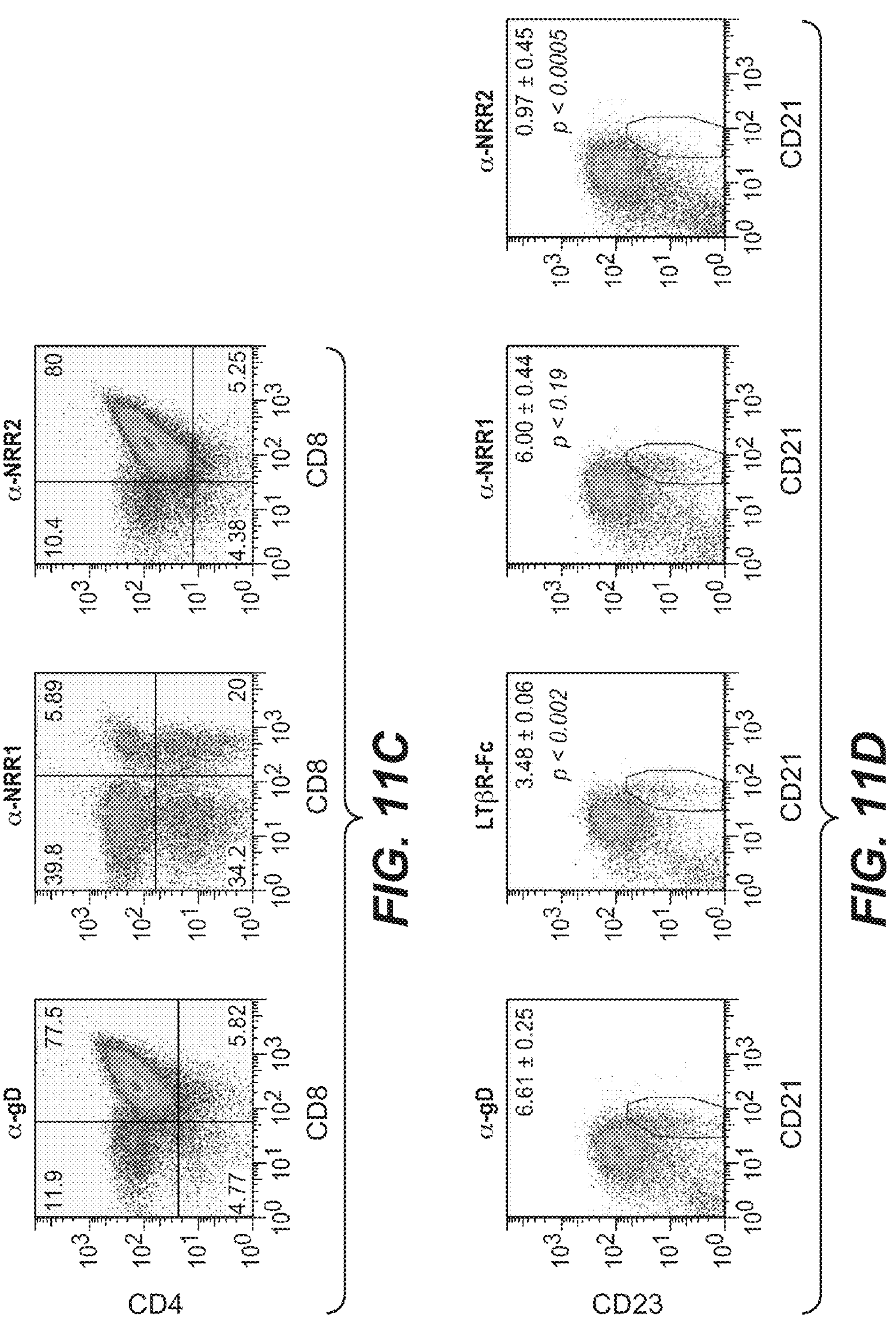
Figure 21:
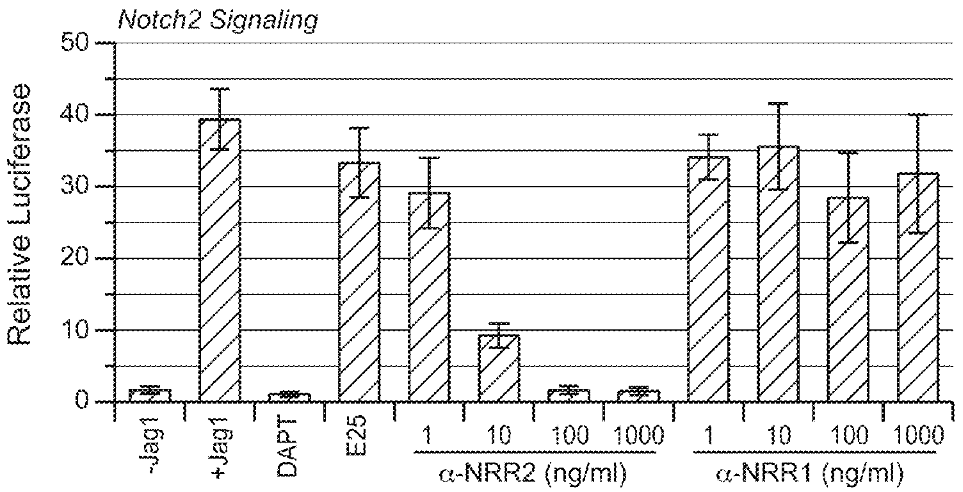

FIG. 21 shows that anti-NRR1 does not block Notch2-induced signaling in vitro, as described in Example B(2). Co-culture assay in U87MG cells, as described in FIG. 10B. Although anti-NRR1 potently inhibits Notch1 signaling in vitro (FIG. 10A) and in vivo (FIGS. 11A-C), it does not affect Notch2 signaling, even when used at a concentration (1000 ng/ml) that is over 100-fold above the $IC_{50}$. This result is consistent with the specific binding of anti-NRR1 to Notch1 (FIGS. 9 and 12) as well as the lack of anti-NRR1 inhibition of Notch2 in vivo (FIG. 11D).

Figure 22:
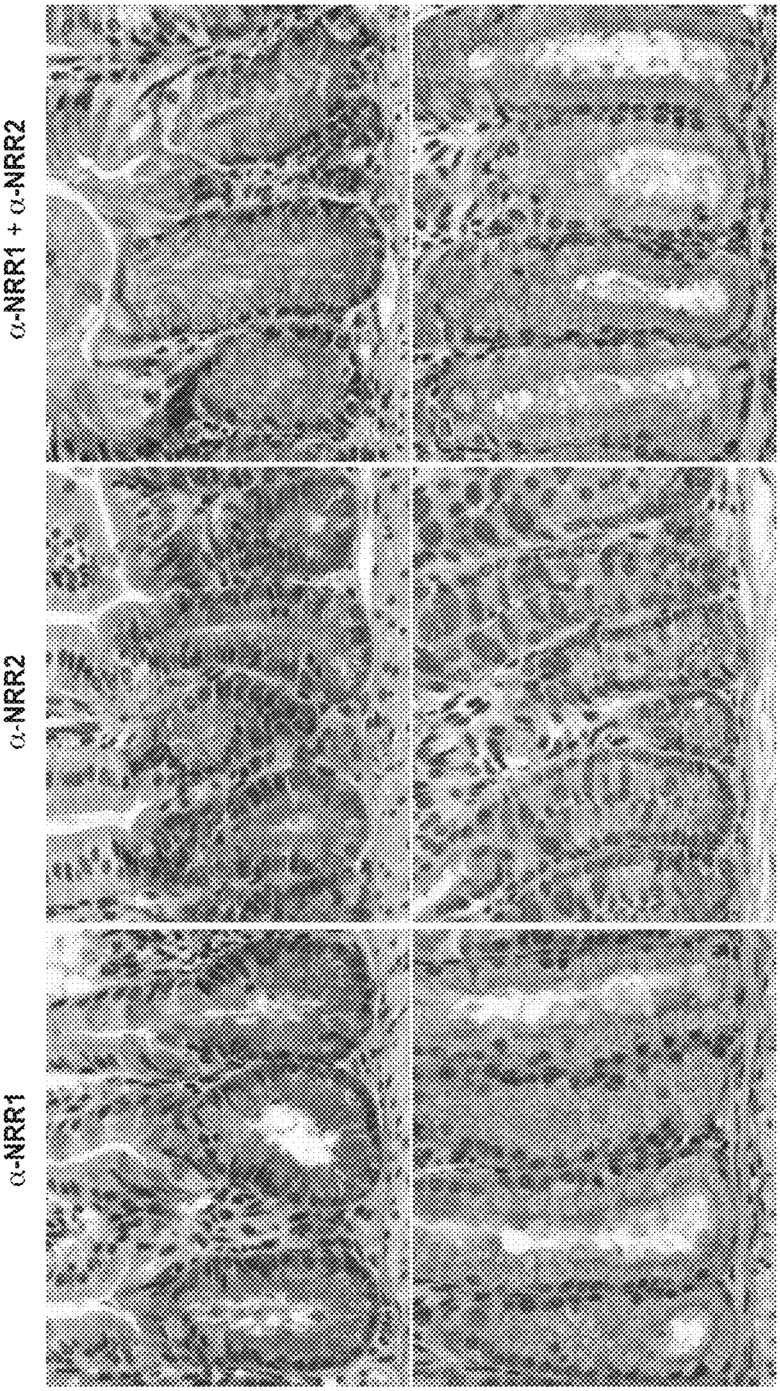

FIG. 22 shows possible synergistic effects of anti-NRR1 and anti-NRR2 on intestinal cell differentiation, as described in Example B8.

Figure 23:
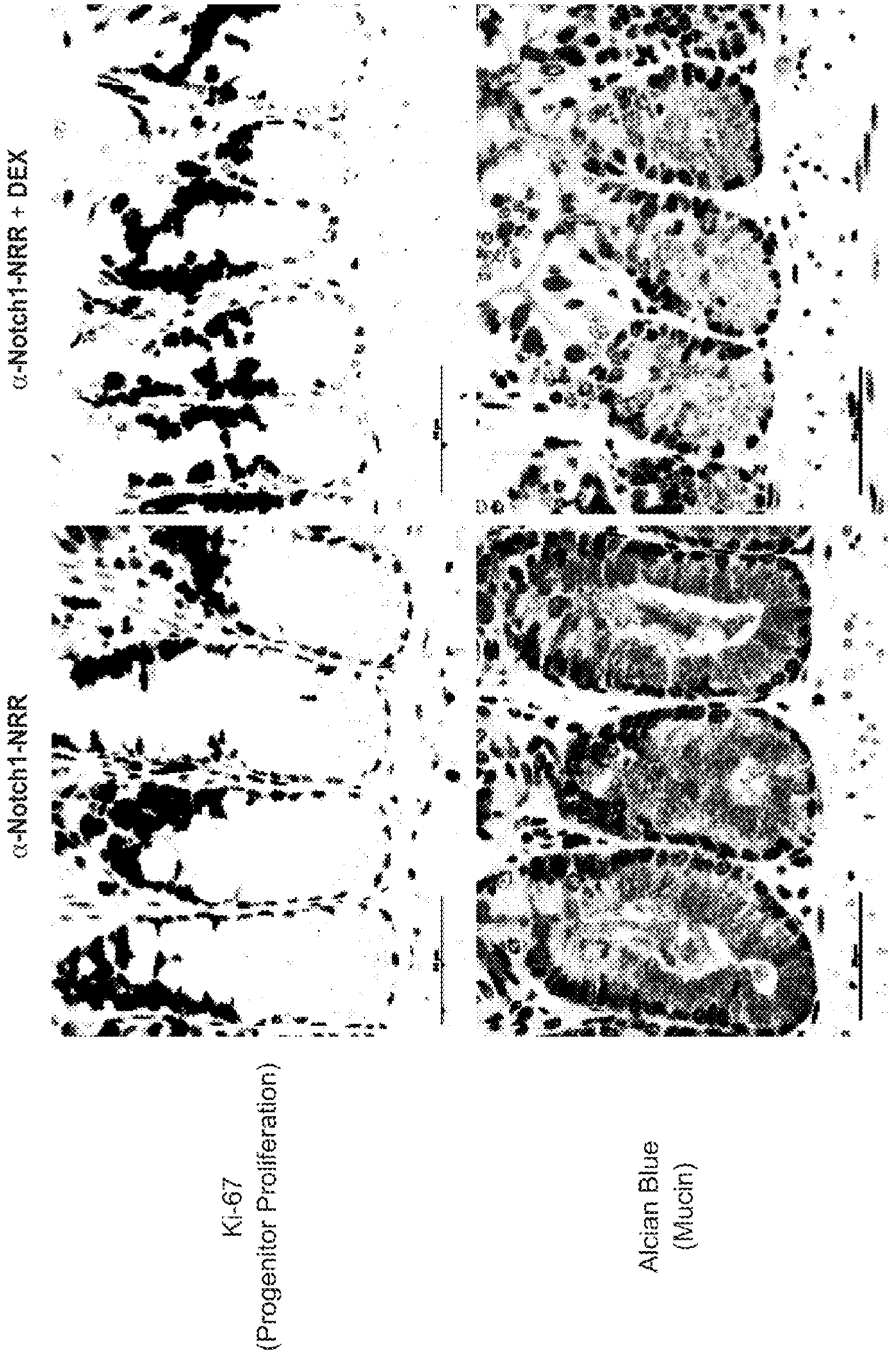

FIG. 23 shows that dexamethasone at least partially rescues the intestinal phenotype caused by anti-NRR1, as described in Example B(9).

Figure 24A:
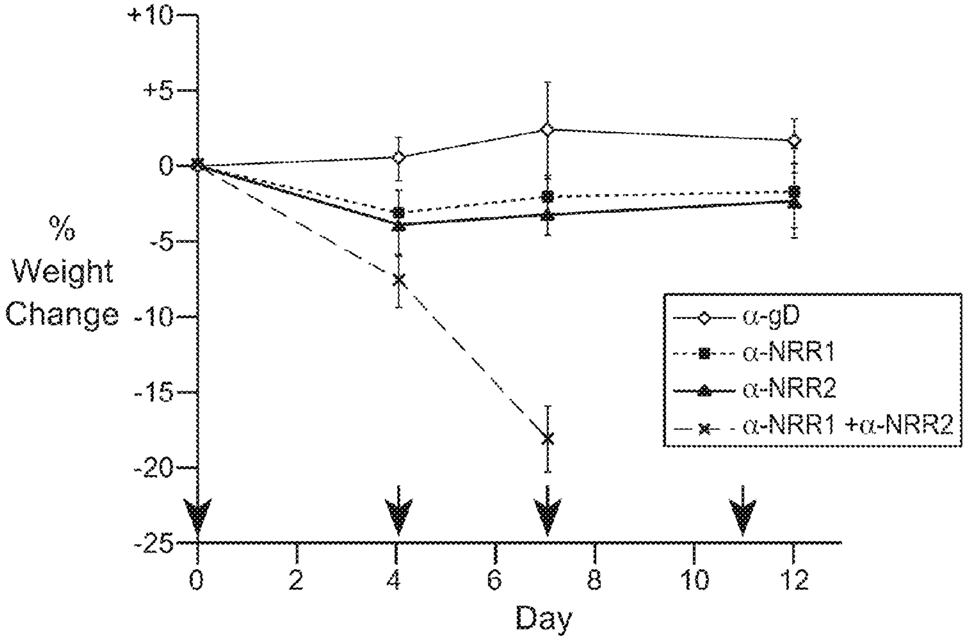

FIGS. 24A and B show that selective blocking of either Notch1 or Notch2 minimizes or avoids goblet cell metaplasia associated with pan-Notch inhibition, whereas blocking both Notch1 and Notch2 causes severe goblet cell metaplasia. (A) As described in Example B8, mice were dosed with 5 mg/kg of anti-NRR1, anti-NRR2, or both, or a negative control antibody anti-gD on the days marked with arrows; total body weight change (mean+/−standard deviation) vs. time is shown. (B) Immunohistochemical analyses of small intestines from mice treated as in (A), using Alcian Blue for mucin to mark secretory goblet cells.

Figure 25A:
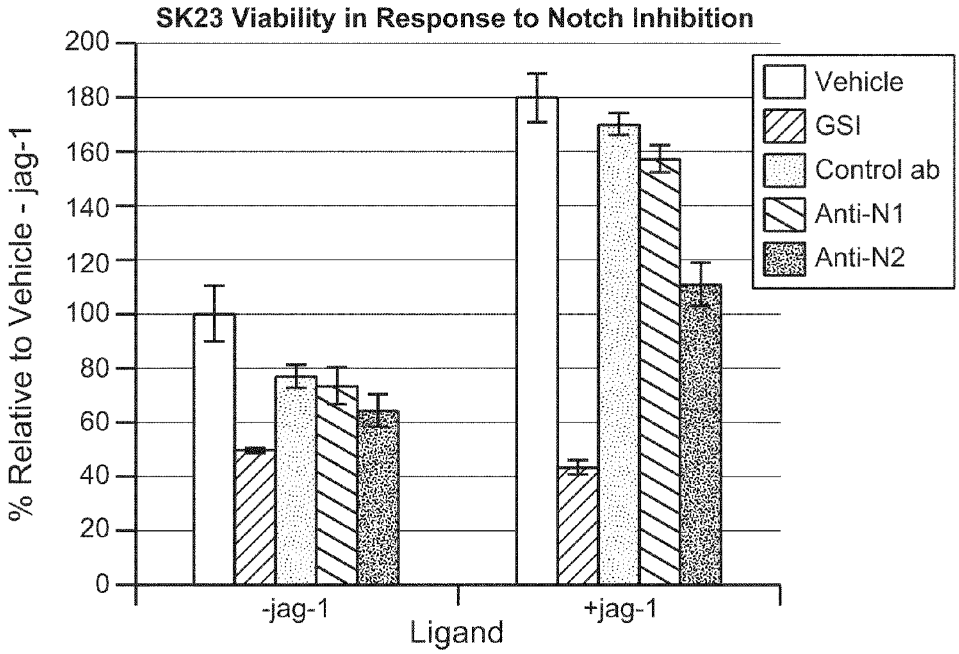
Figure 25B:
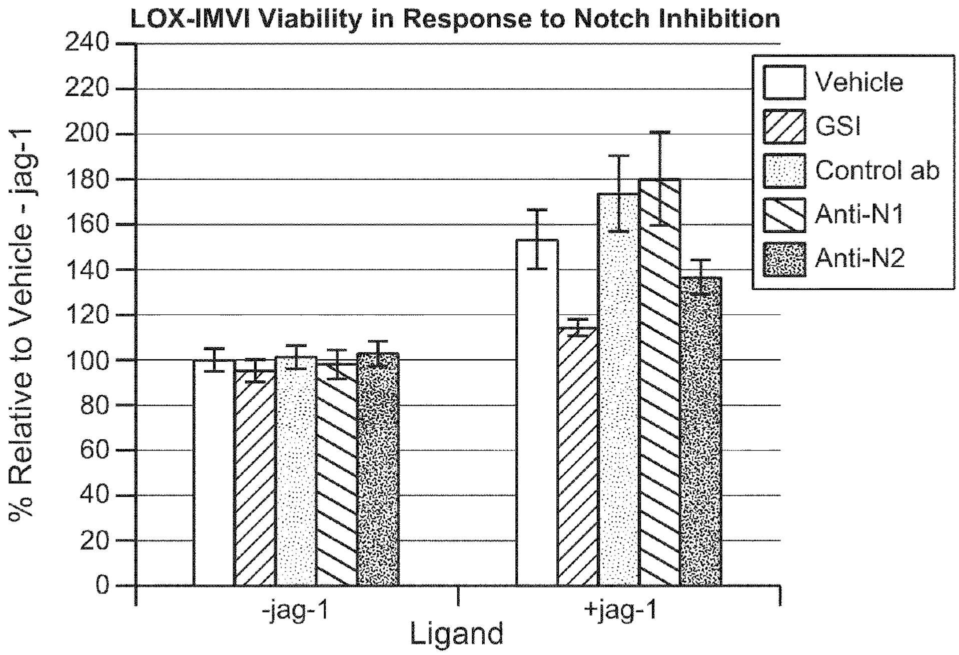

FIGS. 25A and 25B show that anti-NRR2 (referred to as "anti-N2") inhibits the growth of human melanoma cell lines SK23 and LOX-IMVI in vitro, as described in Example B(10).

Figure 26:
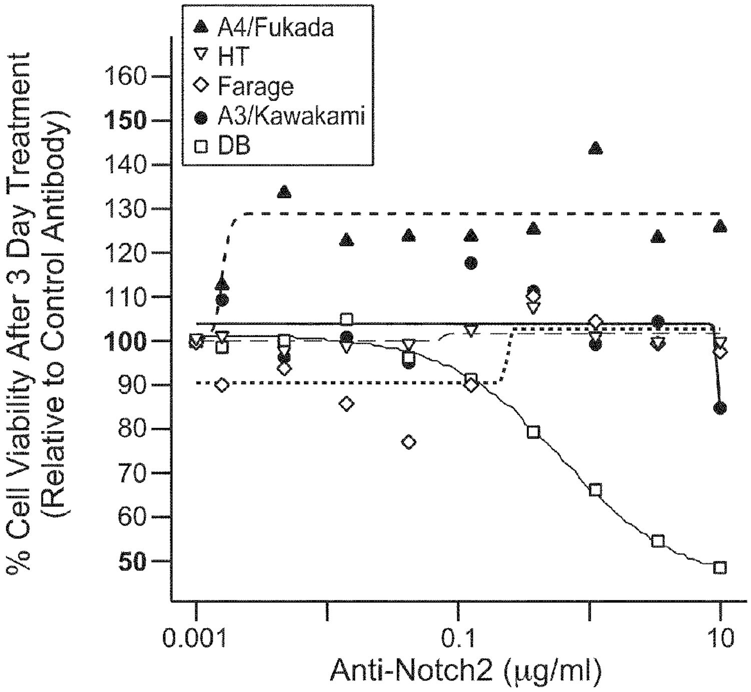

FIG. 26 shows the effect of anti-NRR2 (referred to as "anti-Notch2") on five diffuse large B-cell lymphoma (DLBCL) cell lines (listed on the right). As described in Example B(11), growth of one of the cell lines, "DB," was strongly inhibited by treatment with anti-NRR2.

Figure 27:
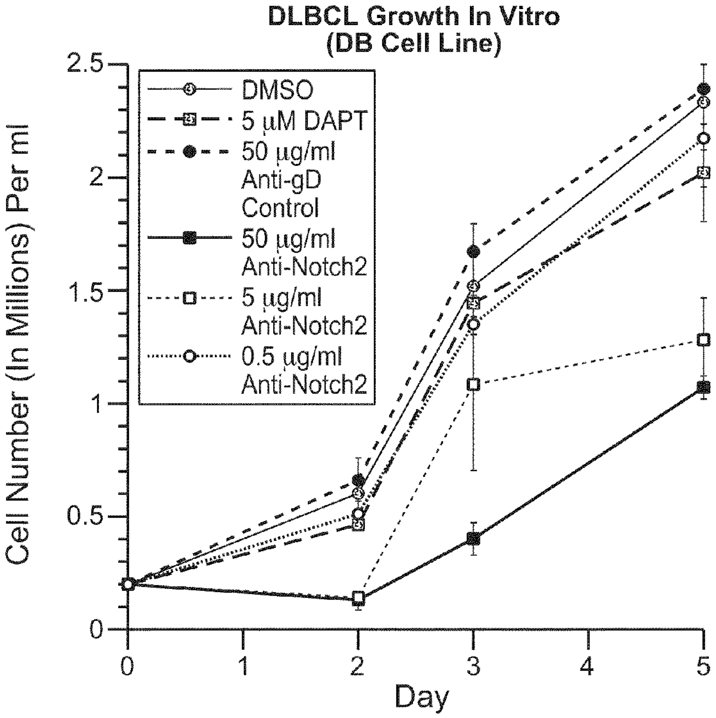

FIG. 27 shows the effect of anti-NRR2 (referred to as "anti-Notch2") on the growth of the DB DLBCL cell line over time, as described in Example B(11).

DETAILED DESCRIPTION OF EMBODIMENTS OF THE INVENTION

The invention provides isolated antibodies that bind to Notch and methods of using the same, e.g., for the diagnosis or treatment of diseases associated with expression or activity of Notch.

I. GENERAL TECHNIQUES

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd. edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. DEFINITIONS

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 dalto composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "anti-Notch1 NRR antibody" or "an antibody that binds to Notch1 NRR" refers to an antibody that is capable of binding Notch1 NRR with sufficient affinity such that the antibody is useful as a diagnostic and/or therapeutic agent in targeting Notch1. Preferably, the extent of binding of an anti-Notch1 NRR antibody antibody to an unrelated, non-Notch protein is less than about 10% of the binding of the antibody to Notch1 NRR as measured, e.g., by a radioimmunoassay (RIA). In certain embodiments, an antibody that binds to Notch1 NRR has a dissociation constant (Kd) of ≦1 μM, ≦100 nM, ≦10 nM, ≦1 nM, or ≦0.1 nM. In certain embodiments, an anti-Notch1 NRR antibody binds to an epitope of Notch that is conserved among Notch from different species, e.g., rodents (mice, rats) and primates.

The term "anti-Notch2 NRR antibody" or "an antibody that binds to Notch2 NRR" refers to an antibody that is capable of binding Notch2 NRR with sufficient affinity such that the antibody is useful as a diagnostic and/or therapeutic agent in targeting Notch2. Preferably, the extent of binding of an anti-Notch2 NRR antibody antibody to an unrelated, non-Notch protein is less than about 10% of the binding of the antibody to Notch2 NRR as measured, e.g., by a radioimmunoassay (RIA). In certain embodiments, an antibody that binds to Notch2 NRR has a dissociation constant (Kd) of ≦1 μM, ≦100 nM, ≦10 nM, ≦1 nM, or ≦0.1 nM. In certain embodiments, an anti-Notch2 NRR antibody binds to an epitope of Notch that is conserved among Notch from different species, e.g., rodents (mice, rats) and primates.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147 (1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Patent Application Publication No. US 2008/0181888 A1, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which partially or fully mimics at least one of the functional activities of a polypeptide of interest.

"Growth inhibitory" antibodies are those that prevent or reduce proliferation of a cell expressing an antigen to which the antibody binds. For example, the antibody may prevent or reduce proliferation of cancer cells in vitro and/or in vivo.

Antibodies that "induce apoptosis" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include Clq binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS* (*USA*) 95:652-656 (1998).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

An "acceptor human framework" or a "human acceptor framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferably those changes occur at only three, two, or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. In one embodiment, for the VL, the subgroup is subgroup kappa I as in Kabat et al., supra. In one embodiment, for the VH, the subgroup is subgroup III as in Kabat et al., supra.

A "VH subgroup III consensus framework" comprises the consensus sequence obtained from the amino acid sequences in variable heavy subgroup III of Kabat et al., supra. In one embodiment, a human acceptor framework is derived from the VH subgroup III consensus framework and comprises an amino acid sequence comprising at least a portion or all of each of the following sequences: (SEQ ID NO:50)-H1-(SEQ ID NO:51)-H2-(SEQ ID NO:57 or 59)-H3-(SEQ ID NO: 35). In some embodiments, the last residue (S11) of SEQ ID NO:35 is substituted with an alanine.

A "VL subgroup I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: (SEQ ID NO:60)-L1-(SEQ ID NO:61)-L2-(SEQ ID NO:62)-L3-(SEQ ID NO:63).

"Purified" means that a molecule is present in a sample at a concentration of at least 95% by weight, or at least 98% by weight of the sample in which it is contained.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, $\alpha$-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)$NR_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "Notch," as used herein, refers to any native Notch (Notch1-4) from any vertebrate source, including mammals such as primates (e.g. humans) and rodents (e.g., mice and rats), unless otherwise indicated. The term encompasses "full-length," unprocessed Notch as well as any form of Notch that results from processing in the cell. The term also encompasses naturally occurring variants of Notch, e.g., splice variants or allelic variants.

The term "Notch1," as used herein, refers to any native Notch1 from any vertebrate source, including mammals such as primates (e.g. humans) and rodents (e.g., mice and rats), unless otherwise indicated. The term encompasses "full-length," unprocessed Notch1 as well as any form of Notch1 that results from processing in the cell. The term also encompasses naturally occurring variants of Notch1, e.g., splice variants or allelic variants.

The term "Notch2," as used herein, refers to any native Notch2 from any vertebrate source, including mammals such as primates (e.g. humans) and rodents (e.g., mice and rats), unless otherwise indicated. The term encompasses "full-length," unprocessed Notch2 as well as any form of Notch2 that results from processing in the cell. The term also encompasses naturally occurring variants of Notch2, e.g., splice variants or allelic variants.

The term "Notch2 activity" refers to Notch2 signaling. An agent (e.g., an antibody) that "inhibits Notch2 activity" significantly decreases Notch2 signaling relative to the level of Notch2 signaling observed in an appropriate control under substantially identical conditions. In certain embodiments, Notch2 activity may be assessed by a suitable reporter assay, as described herein in Example B(2). In certain embodiments, Notch2 activity may be assessed by measuring generation of marginal B zone cells, as described herein in Example B(4). In certain embodiments, the decrease in Notch2 signaling is at least 2-, 3-, 4-, 5-, or 10-fold below the level observed in the control.

The term "Notch2 NRR" refers to a region of Notch2 consisting of the three LNR modules (LNR-A, LNR-B, and LNR-C) and the HD domain (HD-N and HD-C). Exemplary human and mouse Notch2 NRR sequences are shown in FIG. 18 (SEQ ID NOs:28 and 29, respectively). The Notch2 NRR may consist of non-covalently linked fragments, e.g., that result from the processing of Notch2 at S1, as well as a single contiguous polypeptide sequence. By way of example and with reference to FIG. 18, human Notch2 NRR may consist of amino acids 1422-1677 of human Notch2 (SEQ ID NO:75), or alternatively, amino acids 1422-1608 of SEQ ID NO:75 noncovalently linked to amino acids 1609-1677 of SEQ ID NO:75.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "disorder" is any condition or disease that would benefit from treatment with a composition or method of the invention. This includes chronic and acute disorders including those pathological conditions which predispose the mammal to the disorder in question. Non-limiting examples of disorders to be treated herein include conditions such as cancer.

"B-cell malignancies," also called "B-cell neoplasms," include but are not limited to Hodgkin's disease (e.g., lymphocyte predominant Hodgkin's disease (LPHD)); non-Hodgkin's lymphoma (NHL); follicular center cell (FCC) lymphomas; acute lymphocytic leukemia (ALL, also called B-ALL); precursor B-lymphoblastic leukemia; chronic lymphocytic leukemia (CLL, also called B-CLL); Hairy cell leukemia; marginal zone B-cell lymphomas (including nodal, MALT, and splenic types); multiple myeloma (plasmacytoma, plasma cell myeloma); small non-cleaved cell lymphomas (e.g., Burkitt's lymphoma); large cell lymphomas (including diffuse large cell (B-cell), diffuse mixed cell, and immunoblastic lymphoma); mantle cell lymphoma; small lymphocytic lymphoma; AIDS-related lymphoma and Waldenstrom's macroglobulinemia. Indolent lymphoma is a slow-growing, incurable disease in which the average patient survives between six and 10 years following numerous periods of remission and relapse; aggressive lymphomas are fast growing forms of lymphoma encompassing high grade and some categories of intermediate grade NHLs.

The term "melanoma" refers to a malignant tumor of melanocytes, which are found primarily in the skin but which are also found in the eye (uveal melanoma) or in the intestines.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile.

A "sterile" formulation is aseptic or free from all living microorganisms and their spores.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., *Angew. Chem. Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (such as a cell expressing Notch) either in vitro or in vivo. Thus, the growth inhibitory agent may be one which significantly reduces the percentage of cells (such as a cell expressing Notch) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

III. COMPOSITIONS AND METHODS

The invention is based in part on the identification of Notch binding agents, e.g., antibodies and fragments thereof. In specific embodiments, the invention concerns Notch2 negative regulatory region (NRR) binding agents, such as isolated antibodies that bind Notch2 NRR and fragments thereof. Such antibodies are useful, e.g., for the diagnosis or treatment of disorders associated with expression and/or activity of Notch2 (e.g., increased expression or activity). In specific embodiments, anti-Notch2 NRR antibodies are useful for the diagnosis or treatment of cancer, e.g., B-cell malignancies and melanoma. Accordingly, the invention provides methods, compositions, kits, and articles of manufacture related to Notch2 NRR binding.

A. Anti-Notch2 NRR Antibodies

1. Exemplary Phage Library-Derived Antibodies

Exemplary monoclonal antibodies that were derived from a phage library are provided herein, as described in Example B. An antibody designated "Antibody D" that binds to Notch2 NRR was isolated. That antibody was affinity matured to generate antibodies designated Antibody D-1, Antibody D-2, and Antibody D-3. The sequences of the heavy chain and light chain hypervariable regions (HVRs) of Antibody D, Antibody D-1, Antibody D-2, and Antibody D-3 are shown in FIGS. 1 and 2. The sequences of the heavy and light chain variable domains of Antibody D, Antibody D-1, Antibody D-2, and Antibody D-3 are shown in FIGS. 3 and 4. Further embodiments of anti-Notch2 NRR antibodies are provided as follows.

In one aspect, an antibody that specifically binds to Notch2 NRR is provided, wherein the antibody comprises at least one, two, three, four, five, or six HVRs selected from:

(a) an HVR-H1 comprising an amino acid sequence that conforms to the consensus sequence of SEQ ID NO:3;

(b) an HVR-H2 comprising the amino acid sequence of SEQ ID NO:4;

(c) an HVR-H3 comprising the amino acid sequence of SEQ ID NO:5;

(d) an HVR-L1 comprising an amino acid sequence that conforms to the consensus sequence of SEQ ID NO:10;

(e) an HVR-L2 comprising an amino acid sequence that conforms to the consensus sequence of SEQ ID NO:14; and (f) an HVR-L3 comprising an amino acid sequence that conforms to the consensus sequence of SEQ ID NO:19.

In a further aspect, the antibody comprises an HVR-H3 comprising the amino acid sequence of SEQ ID NO:5 and at least one, two, three, four, or five HVRs selected from (a), (b), (d), (e), and (f) above. In a further aspect, the antibody comprises (a), (b), (c), (d), (e), and (f) above. With respect to (a), (d), (e), and (f), any one or more of the following embodiments are contemplated: HVR-H1 comprises an amino acid sequence selected from SEQ ID NOs:1-2; HVR-L1 comprises an amino acid sequence selected from SEQ ID NOs:6-9; HVR-L2 comprises an amino acid sequence selected from SEQ ID NOs:11-13; and HVR-L3 comprises an amino acid sequence selected from SEQ ID NOs:15-18.

In another aspect, an antibody that specifically binds to Notch2 NRR is provided, wherein the antibody comprises an HVR-H1 comprising an amino acid sequence that conforms to the consensus sequence of SEQ ID NO:3, an HVR-H2 comprising the amino acid sequence of SEQ ID NO:4, and an HVR-H3 comprising the amino acid sequence of SEQ ID NO:5. In one embodiment, HVR-H1 comprises an amino acid sequence selected from SEQ ID NOs:1-2.

In another aspect, an antibody that specifically binds to Notch2 NRR is provided, wherein the antibody comprises an HVR-L1 comprising an amino acid sequence that conforms to the consensus sequence of SEQ ID NO:10, an HVR-L2 comprising an amino acid sequence that conforms to the consensus sequence of SEQ ID NO:14, and an HVR-L3 comprising an amino acid sequence that conforms to the consensus sequence of SEQ ID NO:19. The following embodiments are contemplated in any combination: HVR-L1 comprises an amino acid sequence selected from SEQ ID NOs:6-9; HVR-L2 comprises an amino acid sequence selected from SEQ ID NOs:11-13; and HVR-L3 comprises an amino acid sequence selected from SEQ ID NOs:15-18. In one embodiment, an antibody that binds to Notch2 NRR comprises an HVR-L1 comprising the amino acid sequence of SEQ ID NO:6; an HVR-L2 comprising the amino acid sequence of SEQ ID NO:11; and an HVR-L3 comprising the amino acid sequence of SEQ ID NO:15. In another embodiment, an antibody that binds to Notch2 NRR comprises an HVR-L1 comprising the amino acid sequence of SEQ ID NO:7; an HVR-L2 comprising the amino acid sequence of SEQ ID NO:11; and an HVR-L3 comprising the amino acid sequence of SEQ ID NO:16. In another embodiment, an antibody that binds to Notch2 NRR comprises an HVR-L1 comprising the amino acid sequence of SEQ ID NO:8; an HVR-L2 comprising the amino acid sequence of SEQ ID NO:12; and an HVR-L3 comprising the amino acid sequence of SEQ ID NO:17. In another embodiment, an antibody that binds to Notch2 NRR comprises an HVR-L1 comprising the amino acid sequence of SEQ ID NO:9; an HVR-L2 comprising the amino acid sequence of SEQ ID NO:13; and an HVR-L3 comprising the amino acid sequence of SEQ ID NO:18.

In one embodiment, an antibody that specifically binds to Notch2 NRR is provided, wherein the antibody comprises:

(a) an HVR-H1 comprising the amino acid sequence of SEQ ID NO:1;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:6;

(e) an HVR-L2 comprising the amino acid sequence of SEQ ID NO:11; and (f) an HVR-L3 comprising the amino acid sequence of SEQ ID NO:15.

In another embodiment, an antibody that specifically binds to Notch2 NRR is provided, wherein the antibody comprises:

(a) an HVR-H1 comprising the amino acid sequence of SEQ ID NO:2;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:7;

(e) an HVR-L2 comprising the amino acid sequence of SEQ ID NO:11; and (f) an HVR-L3 comprising the amino acid sequence of SEQ ID NO:16.

In another embodiment, an antibody that specifically binds to Notch2 NRR is provided, wherein the antibody comprises:

(a) an HVR-H1 comprising the amino acid sequence of SEQ ID NO:2;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:8;

(e) an HVR-L2 comprising the amino acid sequence of SEQ ID NO:12; and (f) an HVR-L3 comprising the amino acid sequence of SEQ ID NO:17.

In another embodiment, an antibody that specifically binds to Notch2 NRR is provided, wherein the antibody comprises:

(a) an HVR-H1 comprising the amino acid sequence of SEQ ID NO:2;

(b) an HVR-H2 comprising the amino acid sequence of SEQ ID NO:4;

(c) an HVR-H3 comprising the amino acid sequence of SEQ ID NO:5;

(d) an HVR-L1 comprising the amino acid sequence of SEQ ID NO:9;

(e) an HVR-L2 comprising the amino acid sequence of SEQ ID NO:13; and (f) an HVR-L3 comprising the amino acid sequence of SEQ ID NO:18.

In certain embodiments, any of the above antibodies further comprises at least one framework selected from a VH subgroup III consensus framework and a VL subgroup I consensus framework.

In certain embodiments, an anti-Notch2 NRR antibody is affinity matured. For example, any one or more of the following substitutions in the indicated HVR positions (Kabat numbered) may be made in any combination:

in HVR-H1 (SEQ ID NO:1): S28T; T30S;

in HVR-L1 (SEQ ID NO:6): S28N; 129N or V; S30R or K; S31R; Y32F in HVR-L2 (SEQ ID NO:11): G50R; S53I or T; A55E in HVR-L3 (SEQ ID NO:15): S93I or R; L96W or H

The specific antibodies disclosed herein, i.e., Antibody D as well as affinity matured forms of Antibody D (D-1, D-2, and D-3), may undergo further affinity maturation. Accordingly, affinity matured forms of any of the antibodies described herein are provided.

In certain embodiments, an anti-Notch2 NRR antibody having any of the above HVR sequences can further comprise any suitable framework variable domain sequence, provided binding activity to Notch2 NRR is substantially retained. In certain embodiments, an anti-Notch2 NRR antibody comprises a human variable heavy (VH) consensus framework sequence, as in any of the VH consensus framework sequences shown in FIGS. 5A and 5B. In one embodiment, the VH consensus framework sequence comprises a human subgroup III heavy chain framework consensus sequence, e.g., as shown in FIGS. 5A and 5B. In another embodiment, the VH consensus framework sequence comprises an "Acceptor 2" framework sequence, e.g., as shown in FIGS. 5A and 5B. In a particular embodiment, the VH framework consensus sequence comprises FR1-FR4 of Acceptor 2B or Acceptor 2D, wherein the FR4 comprises SEQ ID NO:35 (FIGS. 5A and 5B), with the last residue of SEQ ID NO:35 (S11) optionally being substituted with alanine 1n a further particular embodiment, the VH framework consensus sequence comprises the sequences of SEQ ID NOs:50; 51; 57 or 59; and 35, wherein S11 of SEQ ID NO:35 is optionally substituted with alanine.

In certain embodiments, an anti-Notch2 NRR antibody having any of the above HVR sequences can further comprise a human variable light (VL) consensus framework sequence as shown in FIGS. 6A and 6B. In one embodiment, the VL consensus framework sequence comprises a human VL kappa subgroup I consensus framework (κv1) sequence, e.g., as shown in FIGS. 6A and 6B. In another embodiment, the VL framework consensus sequence comprises FR1-FR4 of huMAb4D5-8 as shown in FIG. 7 or 8. In a particular embodiment, the VL framework consensus sequence comprises the sequences of SEQ ID NOs:60, 61, 62, and 63.

In another aspect, an anti-Notch2 NRR antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs:20-21. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Notch2 NRR antibody comprising that sequence retains the ability to bind to Notch2 NRR. In certain embodiments, a total of 1 to 10 amino acids have been substituted, inserted and/or deleted in an amino acid sequence selected from SEQ ID NOs:20-21. In certain embodiments, substitutions, insertions, or deletions occur in regions outside the HVRs (i.e., in the FRs). In a particular embodiment, the VH comprises one, two or three HVRs selected from: (a) an HVR-H1 comprising an amino acid sequence that conforms to the consensus sequence of SEQ ID NO:3, (b) an HVR-H2 comprising the amino acid sequence of SEQ ID NO:4, and (c) an HVR-H3 comprising the amino acid sequence of SEQ ID NO:5. In one such embodiment, HVR-H1 comprises an amino acid sequence selected from SEQ ID NOs:1-2.

In another aspect, an antibody that specifically binds to Notch2 NRR is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs:22-25. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Notch2 NRR antibody comprising that sequence retains the ability to bind to Notch2 NRR. In certain embodiments, a total of 1 to 10 amino acids have been substituted, inserted and/or deleted in an amino acid sequence selected from SEQ ID NOs:22-25. In certain embodiments, the substitutions, insertions, or deletions occur in regions outside the HVRs (i.e., in the FRs). In a particular embodiment, the VL comprises one, two or three HVRs selected from (a) an HVR-L1 comprising an amino acid sequence that conforms to the consensus sequence of SEQ ID NO:10; (b) an HVR-L2 comprising an amino acid sequence that conforms to the consensus sequence of SEQ ID NO:14; and (c) an HVR-L3 comprising an amino acid sequence that conforms to the consensus sequence of SEQ ID NO:19. In one such embodiment, the VL comprises one, two or three HVRs selected from (a) an HVR-L1 comprising an amino acid sequence selected from SEQ ID NOs:6-9; (b) an HVR-L2 comprising an amino acid sequence selected from SEQ ID NOs:11-13; and (c) an HVR-L3 comprising an amino acid sequence selected from SEQ ID NOs:15-18. In one such embodiment, the VL comprises one, two or three HVRs selected from (a) an HVR-L1 comprising the amino acid sequence of SEQ ID NO:6; (b) an HVR-L2 comprising the amino acid sequence of SEQ ID NO:11; and (c) an HVR-L3 *comprising the amino acid sequence of SEQ ID NO:*15. In another such embodiment, the VL comprises one, two or three HVRs selected from (a) an HVR-L1 comprising the amino acid sequence of SEQ ID NO:7; (b) an HVR-L2 comprising the amino acid sequence of SEQ ID NO:11; and (c) an HVR-L3 comprising the amino acid sequence of SEQ ID NO:16. In another such embodiment, the VL comprises one, two or three HVRs selected from (a) an HVR-L1 comprising the amino acid sequence of SEQ ID NO:8; (b) an HVR-L2 comprising the amino acid sequence of SEQ ID NO:12; and (c) an HVR-L3 comprising the amino acid sequence of SEQ ID NO:17. In another such embodiment, the VL comprises one, two or three HVRs selected from (a) an HVR-L1 comprising the amino acid sequence of SEQ ID NO:9; (b) an HVR-L2 comprising the amino acid sequence of SEQ ID NO:13; and (c) an HVR-L3 comprising the amino acid sequence of SEQ ID NO:18.

In certain embodiments of the variant VH and VL sequences provided above, substitutions, insertions, or deletions may occur within the HVRs. In such embodiments, substitutions, insertions, or deletions may occur within one or more HVRs so long as such alterations do not substantially reduce the ability of the antibody to bind antigen. For example, conservative alterations that do not substantially reduce binding affinity may be made in HVRs. In certain instances, alterations in HVRs may actually improve antibody affinity. Such alterations may be made in HVR "hotspots" (i.e., residues encoded by codons that undergo mutation at high frequency during the somatic maturation process) in order to increase antibody affinity. (See, e.g., Chowdhury, *Methods Mol. Biol.* 207:179-196, 2008.) In certain embodiments of the variant VH and VL sequences provided above, each HVR either is conserved (unaltered), or contains no more than a single amino acid substitution, insertion or deletion.

In another aspect, an antibody that specifically binds Notch2 *NRR is provided, wherein the antibody comprises a VH as in any of the embodiments provided above, and a VL as in any of the embodiments provided above. In one embodiment, the antibody comprises a VH having at least* 90%, 91%, 92%, 93%, 94%, 95%, 96%, 97%, 98%, 99%, or 100% sequence identity to the amino acid sequence of SEQ ID NO:20, and a VL having at least 90%, 91%, 92%, 93%, 94%, 95%, 96%, 97%, 98%, 99%, or 100% sequence identity to the amino acid sequence of SEQ ID NO:22. In one such embodiment, the VH comprises one, two or three HVRs selected from: (a) an HVR-H1 comprising the amino acid sequence of SEQ ID NO:1, (b) an HVR-H2 comprising the amino acid sequence of SEQ ID NO:4, and (c) an HVR-H3 comprising the amino acid sequence of SEQ ID NO:5, and the VL comprises one, two or three HVRs selected from (a) an HVR-L1 comprising the amino acid sequence of SEQ ID NO:6; (b) an HVR-L2 comprising the amino acid sequence of SEQ ID NO:11; and (c) an HVR-L3 comprising the amino acid sequence of SEQ ID NO:15. In a particular embodiment, the antibody comprises a VH comprising the amino acid sequence of SEQ ID NO:20, and a VL comprising the amino acid sequence of SEQ ID NO:22.

In another embodiment, an anti-Notch2 NRR antibody that specifically binds Notch2 NRR comprises a VH having at least 90%, 91%, 92%, 93%, 94%, 95%, 96%, 97%, 98%, 99%, or 100% sequence identity to the amino acid sequence of SEQ ID NO:21, and a VL having at least 90%, 91%, 92%, 93%, 94%, 95%, 96%, 97%, 98%, 99%, or 100% sequence identity to an amino acid sequence selected from SEQ ID NOs:23-25. In one such embodiment, the VH comprises one, two or three HVRs selected from: (a) an HVR-H1 comprising the amino acid sequence of SEQ ID NO:2, (b) an HVR-H2 comprising the amino acid sequence of SEQ ID NO:4, and (c) an HVR-H3 comprising the amino acid sequence of SEQ ID NO:5, and the VL comprises one, two or three HVRs selected from (a) an HVR-L1 comprising an amino acid sequence selected from SEQ ID NOs:7-9; (b) an HVR-L2 comprising an amino acid sequence selected from SEQ ID NOs:11-13; and (c) an HVR-L3 comprising an amino acid sequence selected from SEQ ID NOs:16-18. In particular embodiments, the antibody comprises a VH comprising the amino acid sequence of SEQ ID NO:21 and a VL comprising an amino acid sequence selected from SEQ ID NOs:23-25.

In certain embodiments, an affinity-matured form of any of the above antibodies is provided. In further embodiments, a recombinant protein that specifically binds Notch2 NRR is provided, wherein the recombinant protein comprises an antigen binding site(s) of any of the above antibodies. In one such embodiment, a recombinant protein comprises any one or more of the HVRs provided above.

In certain embodiments, a polynucleotide encoding any of the above antibodies is provided. In one embodiment, a vector comprising the polynucleotide is provided. In one embodiment, a host cell comprising the vector is provided. In one embodiment, the host cell is eukaryotic. In one embodiment, the host cell is a CHO cell. In one embodiment, a method of making an anti-Notch2 NRR antibody is provided, wherein the method comprises culturing the host cell under conditions suitable for expression of the polynucleotide encoding the antibody, and isolating the antibody.

2. Further Exemplary Antibodies

In one embodiment, the invention provides an isolated anti-Notch2 NRR antibody that inhibits Notch2 activity. For example, the antibodies of the invention may modulate one or more aspects of Notch2 signaling, including disruption of any biologically relevant Notch2 signaling pathway.

In a further embodiment, the invention provides an isolated anti-Notch2 NRR antibody that binds Notch2 NRR with a Kd of ≦100 nM. In certain embodiments, the anti-Notch2 NRR antibody binds the Notch2 NRR with a Kd of ≦10 nM, ≦1 nM, or ≦0.1 nM. As described in the Examples herein, the exemplary phage Antibody D-3 binds with a Kd of 5 nM. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore, radioimmunoassay (RIA), and ELISA.

In another embodiment, an isolated antibody that binds to Notch2 NRR is provided, wherein the antibody does not significantly bind to a Notch family member other than Notch2 (i.e., Notch1, 3, and 4 in mammals). Such an antibody may be identified using the assays provided in Example B(1). In one embodiment, the antibody binds to human Notch2 NRR and a Notch2 NRR from at least one other non-human species, e.g., mouse.

In another embodiment, an isolated antibody is provided that binds to the same epitope as an antibody provided herein. In one embodiment, an isolated anti-Notch2 NRR antibody is provided that binds to the same epitope as an antibody selected from Antibody D, Antibody D-1, Antibody D-2, and Antibody D-3. In another embodiment, the invention provides an anti-Notch2 NRR antibody that competes with an antibody selected from Antibody D, Antibody D-1, Antibody D-2, and Antibody D-3. In another embodiment, an isolated antibody is provided that binds to at least one domain selected from the LNR-A domain and the HD-C domain of Notch2. In one such embodiment, the antibody binds to both the LNR-A domain and the HD-C domain. In another such embodiment, the antibody further binds to the LNR-B and/or HD-N domains. Those domains are delineated in FIG. 18.

The above embodiments of anti-Notch2 NRR antibodies may be present singly or in any combination. Furthermore, any anti-Notch2 NRR antibody described herein may possess any one or more of the following features: In certain embodiments, an anti-Notch2 NRR antibody is a monoclonal antibody. In certain embodiments, an anti-Notch2 NRR antibody is an antibody fragment selected from a Fab, Fab'-SH, Fv, scFv, or $(Fab')_2$ fragment. In another embodiment, an anti-Notch2 NRR antibody is a humanized, human or chimeric antibody.

3. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

4. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA,* 89:4285; Presta et al. (1993) *J. Immunol.,* 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

5. Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

6. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for Notch2 and the other is for any other antigen. In certain embodiments, bispecific antibodies may bind to two different epitopes of Notch2. Bispecific antibodies may also be used to localize cytotoxic agents to cells which express Notch2. These antibodies possess a Notch2-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. $F(ab')_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al. *J. Immunol.* 147: 60 (1991).

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 1). In one embodiment, a single-domain antibody consists of all or a portion of the heavy chain variable domain of an antibody.

9. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). Clq binding assays may also be carried out to confirm that the antibody is unable to bind Clq and hence lacks CDC activity. To assess complement activation, a CDC assay may be performed (see, for example, Gazzano-Santoro et al., *J. Immunol. Methods* 202: 163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (O)

(3) acidic: Asp (D), Glu (E)

(4) basic: Lys (K), Arg (R), His(H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) Clq binding and/or Complement Dependent Cytotoxicity (CDC), e.g., as described in WO99/51642. See also Duncan & Winter, *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased Clq binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region.

10. Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Certain Methods of Making Antibodies

1. Certain Hybridoma-Based Methods

Monoclonal antibodies of the invention can be made using the hybridoma method first described by Kohler et al., *Nature,* 256:495 (1975), and further described, e.g., in Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue,* 26(4):265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide comprising Notch2 or a fragment thereof (e.g., Notch2 NRR), and an adjuvant, such as monophosphoryl lipid A (MPL)/trehalose dicrynomycolate (TDM) (Ribi Immunochem. Research, Inc., Hamilton, Mont.). A polypeptide comprising Notch2 or a fragment thereof may be prepared using methods well known in the art, such as recombinant methods, some of which are further described herein. Serum from immunized animals is assayed for anti-Notch2 antibodies, and booster immunizations are optionally administered. Lymphocytes from animals producing anti-Notch2 antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology,* 24(3), 105-108 (2006).

Oligopeptides as tools for improving productivity of hybridoma cell cultures are described in Franek, *Trends in Monoclonal Antibody Research,* 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to Notch2. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No.

6,919,436. The method includes using minimal salts, such as lyotropic salts, in the binding process and preferably also using small amounts of organic solvents in the elution process.

2. Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., J. Mol. Biol. (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.,* 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.,* 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J,* 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.,* 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.,* 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.,* 19: 4133-4137 (1991).

In general, nucleic acids encoding antibody gene fragments are obtained from immune cells harvested from humans or animals. If a library biased in favor of anti-Notch2 clones (e.g., anti-Notch2 NRR clones) is desired, the subject is immunized with Notch2 (or Notch2 NRR) to generate an antibody response, and spleen cells and/or circulating B cells other peripheral blood lymphocytes (PBLs) are recovered for library construction. In a preferred embodiment, a human antibody gene fragment library biased in favor of anti-Notch2 clones is obtained by generating an anti-Notch2 antibody response in transgenic mice carrying a functional human immunoglobulin gene array (and lacking a functional endogenous antibody production system) such that Notch2 immunization gives rise to B cells producing human antibodies against Notch2. The generation of human antibody-producing transgenic mice is described below.

Additional enrichment for anti-Notch2 reactive cell populations can be obtained by using a suitable screening procedure to isolate B cells expressing Notch2-specific membrane bound antibody, e.g., by cell separation using Notch2 affinity chromatography or adsorption of cells to fluorochrome-labeled Notch2 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which Notch2 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci.* (*USA*), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.,* 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.,* 227: 776-798 (1992)), and mapped (reported in Matsuda et al., *Nature Genet.,* 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.,* 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128: 119-126 (1993), or in vivo by combinatorial infection, e.g., the loxP system described in Waterhouse et al., *Nucl. Acids Res.,* 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA,* 88: 7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique,* 1: 11-15 (1989)) in the method of Hawkins et al., *J. Mol. Biol.,* 226: 889-896 (1992) or in the method of Gram et al., *Proc. Natl. Acad. Sci. USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.,* 10: 779-783 (1992). This technique allows the production of antibodies and antibody fragments with affinities of about $10^{-9}$ M or less.

Screening of the libraries can be accomplished by various techniques known in the art. For example, Notch2 (or Notch2 NRR) can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized Notch2 under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA,* 88: 7978-7982 (1991), or by alkali, e.g. as described in Marks et al., *J. Mol. Biol.,* 222: 581-597 (1991), or by Notch2 antigen competition, e.g. in a procedure similar to the antigen competition method of Clackson et al., *Nature,* 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins,* 8: 309-314 (1990) and in WO 92/09690, and a low coating density of antigen as described in Marks et al., *Biotechnol.,* 10: 779-783 (1992).

It is possible to select between phage antibodies of different affinities, even with affinities that differ slightly, for Notch2. However, random mutation of a selected antibody (e.g. as performed in some affinity maturation techniques) is likely to give rise to many mutants, most binding to antigen, and a few with higher affinity. With limiting Notch2, rare high affinity phage could be competed out. To retain all higher affinity mutants, phages can be incubated with excess biotinylated Notch2, but with the biotinylated Notch2 at a concentration of lower molarity than the target molar affinity constant for Notch2. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-Notch2 clones may be selected based on activity. In certain embodiments, the invention provides anti-Notch2 antibodies that bind to living cells that naturally express Notch2. In one embodiment, the invention provides anti-Notch2 antibodies that block the binding between a Notch2 ligand and Notch2, but do not block the binding between a Notch2 ligand and a second protein. Fv clones corresponding to such anti-Notch2 antibodies can be selected by (1) isolating anti-Notch2 clones from a phage library as described above, and optionally amplifying the isolated population of phage clones by growing up the population in a suitable bacterial host; (2) selecting Notch2 and a second protein against which blocking and non-blocking activity, respectively, is desired; (3) adsorbing the anti-Notch2 phage clones to immobilized Notch2; (4) using an excess of the second protein to elute any undesired clones that recognize Notch2-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.,* 5: 256 (1993) and Pluckthun, *Immunol. Revs,* 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-Notch2 antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA,* 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

3. Vectors, Host Cells, and Recombinant Methods

Antibodies may also be produced using recombinant methods. For recombinant production of an anti-Notch2 antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* $\alpha$-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2$\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282:39 (1979)). The trp1 gene provides a selection marker for a mutant strain of yeast lacking the ability to grow in tryptophan, for example, ATCC No. 44076 or PEP4-1. Jones, *Genetics,* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology,* 8:135 (1990). Stable multi-copy expression vectors for secretion of mature recombinant human serum albumin by industrial strains of *Kluyveromyces* have also been disclosed. Fleer et al., *Bio/Technology,* 9:968-975 (1991).

d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology, Vol.* 248 (B.K.C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, duckweed (*Lemnaceae*), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including $DHFR^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical are well-established in the art, consistent with the above-described methodologies and/or as deemed appropriate by one skilled in the art for a particular antibody of interest.

C. Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10):2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

1. Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. Patent Application Publication No. US 2005/016993 A1, the disclosures of which are hereby expressly incorporated by reference. Antibody-maytansinoid conjugates comprising the linker component SMCC may be prepared as disclosed in US 2005/016993 A1. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

2. Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

3. Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma1I$, $\alpha2I$, $\alpha3I$, N-acetyl-$\gamma1I$, PSAG and $\theta I1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

4. Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

5. Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

D. Methods

1. Diagnostic Methods and Methods of Detection

In one aspect, antibodies of the invention are useful for detecting the presence of Notch2 in a biological sample. The term "detecting" as used herein encompasses quantitative or qualitative detection. In certain embodiments, a biological sample comprises a cell or tissue, such as cancerous tissue.

In one aspect, the invention provides a method of detecting the presence of Notch2 in a biological sample. In certain embodiments, the method comprises contacting the biological sample with an anti-Notch2 antibody (e.g., an anti-Notch2 NRR antibody) under conditions permissive for binding of the anti-Notch2 antibody to Notch2, and detecting whether a complex is formed between the anti-Notch2 antibody and Notch2.

In one aspect, the invention provides a method of diagnosing a disorder associated with increased expression of Notch2. In certain embodiments, the method comprises contacting a test cell with an anti-Notch2 antibody; determining the level of expression (either quantitatively or qualitatively) of Notch2 by the test cell by detecting binding of the anti-Notch2 antibody to Notch2; and comparing the level of expression of Notch2 by the test cell with the level of expression of Notch2 by a control cell (e.g., a normal cell of the same tissue origin as the test cell, or a cell that expresses Notch2 at levels comparable to such a normal cell, or an average level of expression among multiple control cells), wherein a higher level of expression of Notch2 by the test cell as compared to the control cell indicates the presence of a disorder associated with increased expression of Notch2. In certain embodiments, the test cell is obtained from an individual suspected of having a disorder associated with increased expression of Notch2. In certain embodiments, the disorder is a cell proliferative disorder, such as a cancer or a tumor.

Exemplary disorders that may be diagnosed using an antibody of the invention include cancer, e.g., B-cell malignancies, melanoma, T-cell malignancies (e.g., T-ALL), breast cancer, brain cancer, cervical cancer, colon cancer, and pancreatic cancer.

Certain other methods can be used to detect binding of antibodies to Notch2. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, antibodies are immobilized on an insoluble matrix. Immobilization may entail separating an anti-Notch2 antibody from any Notch2 that remains free in solution. This conventionally is accomplished by either insolubilizing the anti-Notch2 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-Notch2 antibody after formation of a complex between the anti-Notch2 antibody and Notch2, e.g., by immunoprecipitation.

It is understood that any of the above embodiments of diagnosis or detection may be carried out using an immunoconjugate of the invention in place of or in addition to an anti-Notch2 antibody.

2. Therapeutic Methods

An antibody of the invention may be used in, for example, in vitro, ex vivo, and in vivo therapeutic methods. In one aspect, the invention provides methods for inhibiting Notch2 activity, i.e., Notch2 signaling, either in vivo or in vitro, the method comprising exposing a cell to an anti-Notch2 NRR antibody of the invention under conditions permissive for binding of the antibody to Notch2. In certain embodiments, the cell is a cancer cell, e.g., a cancerous B-cell or a melanoma cell. In one embodiment, an anti-Notch2 NRR antibody of the invention can be used for inhibiting Notch2 activity, the method comprising exposing Notch2 to an anti-Notch2 NRR antibody of the invention such that Notch2 activity is inhibited.

An anti-Notch2 NRR antibody of the invention may be used, e.g., for the treatment of disorders associated with expression and/or activity of Notch2, e.g., disorders associated with increased expression or activity of Notch2, or disorders in which expression or activity of Notch2 contributes to a pathogenic state. A "disorder associated with increased expression or activity of Notch2" refers to a disorder in which Notch2 expression or activity is significantly higher than normal.

In one aspect, an antibody of the invention is used to treat or prevent cancer, e.g., B-cell malignancies, melanoma, T-cell malignancies (e.g., T-ALL), breast cancer, brain cancer, cervical cancer, colon cancer, and pancreatic cancer. In certain embodiments, an anti-Notch2 NRR antibody is used to treat a cancer, such as breast cancer, a B-cell malignancy or melanoma.

In a further aspect, an antibody of the invention is used to treat or prevent a cancer, specifically a solid tumor containing cancer stem cells. Cancer stem cells are capable of proliferating to give rise to additional cancer stem cells, as well as other tumor cell populations. See Al-Hajj et al., *Proc. Nat'l Acad. Sci. USA* 100: 3983-3988 (2003). Cancer stem cells are believed to contribute to the recurrence of cancers and the resistance of cancers to drug therapies. Notch receptors have been identified as cancer stem cell markers and as a target for eliminating cancer stem cells responsible for the formation and recurrence of solid tumors. See WO 2008/091641. Such solid tumors include but are not limited to breast, colon, pancreatic, prostate, lung, head and neck, rectal, and colorectal cancers.

In one aspect, the invention provides methods for treating a cancer comprising administering to an individual in need thereof an effective amount of an antibody of the invention. In certain embodiments, a method for treating a cancer comprises administering to an individual in need thereof an effective amount of a pharmaceutical formulation comprising an antibody of the invention and, optionally, at least one additional therapeutic agent, such as those provided below.

Antibodies of the invention can be used either alone or in combination with other compositions in a therapy. For instance, an antibody of the invention may be co-administered with at least one additional therapeutic agent and/or adjuvant. In certain embodiments, an anti-Notch1 antibody (e.g., an anti-Notch1 NRR antibody) is administered with an additional therapeutic agent that inhibits or reduces altered intestinal cell differentiation that would otherwise be induced by such anti-Notch1 antibody. In certain embodiments, the additional therapeutic agent is dexamethasone or tamoxifen. Such combination therapy would be useful, e.g., in treating angiogenic disorders, including tumor-associated angiogenesis, and cancer. In certain embodiments, an anti-Notch2 antibody (e.g., an anti-Notch2 NRR antibody) is administered with an additional therapeutic agent, e.g., a chemotherapeutic agent. Such combination therapy would be useful, e.g., in treating cancer, such as B-cell malignancies and melanoma.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

In one aspect, at least some of the antibodies of the invention can bind Notch2 from species other than human. Accordingly, antibodies of the invention can be used to bind Notch2, e.g., in a mammalian cell culture expressing endogenous or recombinant Notch2, in humans, or in other mammals having a Notch2 with which an antibody of the invention cross-reacts (e.g. chimpanzee, baboon, marmoset, cynomolgus and rhesus monkeys, pig, rat, or mouse).

In one embodiment, an antibody of the invention is used in a method for binding Notch2 in an individual suffering from a disorder associated with increased Notch2 expression and/or activity, the method comprising administering to the individual the antibody such that Notch2 in the individual is bound. In one embodiment, the Notch2 is human Notch2, and the individual is a human individual. Alternatively, the individual can be a mammal expressing Notch2 to which an antibody of the invention binds. Still further the individual can be a mammal into which Notch2 has been introduced (e.g., by administration of Notch2 or by expression of a transgene encoding Notch2).

An antibody of the invention can be administered to a human for therapeutic purposes. Moreover, an antibody of the invention can be administered to a non-human mammal expressing Notch2 with which the antibody cross-reacts (e.g., a primate, pig, rat, or mouse) for veterinary purposes or as an animal model of human disease. Regarding the latter, such animal models may be useful for evaluating the therapeutic efficacy of antibodies of the invention (e.g., testing of dosages and time courses of administration).

An antibody of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described, e.g., in Marasco, *Gene Therapy* 4: 11-15 (1997); Kontermann, *Methods* 34: 163-170 (2004); U.S. Pat. Nos. 6,004,940 and 6,329,173; U.S. Patent Application Publication No. 2003/0104402, and PCT Publication No. WO2003/077945. See also, for example, WO96/07321 published Mar. 14, 1996, concerning the use of gene therapy to generate intracellular antibodies.

Intracellular expression of an intrabody may be effected by introducing a nucleic acid encoding the desired antibody or antigen-binding portion thereof (lacking the wild-type leader sequence and secretory signals normally associated with the gene encoding that antibody or antigen-binding fragment) into a target cell. One or more nucleic acids encoding all or a portion of an antibody of the invention can be delivered to a target cell, such that one or more intrabodies are expressed which are capable of binding to an intracellular target polypeptide and modulating the activity of the target polypeptide. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In certain embodiments, nucleic acid (optionally contained in a vector) may be introduced into a patient's cells by in vivo and ex vivo methods. In one example of in vivo delivery, nucleic acid is injected directly into the patient, e.g., at the site where therapeutic intervention is required. In a further example of in vivo delivery, nucleic acid is introduced into a cell using transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of certain gene marking and gene therapy protocols, see Anderson et al., *Science* 256:808-813 (1992), and WO 93/25673 and the references cited therein. In an example of ex vivo treatment, a patient's cells are removed, nucleic acid is introduced into those isolated cells, and the modified cells are administered to the patient either directly or, for example, encapsulated within porous membranes which are implanted into the patient (see, e.g., U.S. Pat. Nos. 4,892,538 and 5,283, 187). A commonly used vector for ex vivo delivery of a nucleic acid is a retroviral vector.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993).

Entry of antibodies into target cells can be enhanced by other methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

When the binding target of an antibody is located in the brain, certain embodiments of the invention provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9: 398-406 (2002)), interstitial infusion/convection-enhanced delivery (see, e.g., Bobo et al., *Proc. Natl. Acad. Sci. USA* 91: 2076-2080 (1994)), and implanting a delivery device in the brain (see, e.g., Gill et al., *Nature Med.* 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989)), permeabilization by, e.g., bradykinin or permeabilizer A-7 (see, e.g., U.S. Pat. Nos. 5,112,596, 5,268, 164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No. 20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) *Gene Ther.* 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above therapeutic methods may be carried out using an immunoconjugate of the invention in place of or in addition to an anti-Notch2 antibody.

3. Assays

Anti-Notch2 NRR antibodies of the invention may be characterized for their physical/chemical properties and/or biological activities by various assays known in the art.

a) Activity Assays

In one aspect, assays are provided for identifying anti-Notch2 antibodies (e.g., anti-Notch2 NRR antibodies) having biological activity. Biological activity may include, e.g., inhibition or reduction of Notch2 activity, e.g., Notch2 signaling. Antibodies having such biological activity in vivo and/or in vitro are also provided.

In certain embodiments, an anti-Notch2 NRR antibody of the invention is tested for its ability to inhibit generation of marginal zone B cells. An exemplary assay is provided in the Examples. In certain other embodiments, an antibody of the invention is tested for its ability to inhibit expression of a reporter gene that is responsive to Notch2 signaling. An exemplary assay is provided in the Examples.

b) Binding Assays and Other Assays

In one aspect, an antibody of the invention is tested for its antigen binding activity, e.g., by known methods such as ELISA, Western blot, etc. In another aspect, competition assays may be used to identify an antibody (e.g., a monoclonal antibody) that competes with an antibody of the invention. In one embodiment, an antibody competes with Antibody D, Antibody D-1, Antibody D-2, or Antibody D-3 for binding to Notch2. In one such embodiment, a competing antibody binds to the same epitope (e.g., a linear or a conformational epitope) that is bound by Antibody D, Antibody D-1, Antibody D-2, or Antibody D-3. In another embodiment, a competing antibody binds to the same epitope (e.g., a linear or a conformational epitope) that is bound by anti-NRR1 as described in Example B(5), i.e., an epitope comprising LNR-A, LNR-B and HD-C domains of Notch1 NRR. Exemplary competition assays include, but are not limited to, routine assays such as those provided in Harlow and Lane (1988) *Antibodies: A Laboratory Manual* ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in *Methods in Molecular Biology* vol. 66 (Humana Press, Totowa, N.J.). Two antibodies are said to "bind to the same epitope" if each blocks binding of the other by 50% or more.

In an exemplary competition assay, immobilized Notch2 NRR is incubated in a solution comprising a first labeled antibody that binds to Notch2 NRR (e.g., Antibody D, Antibody D-1, Antibody D-2, or Antibody D-3) and a second unlabeled antibody that is being tested for its ability to compete with the first antibody for binding to Notch2 NRR. The second antibody may be present in a hybridoma supernatant. As a control, immobilized Notch2 NRR is incubated in a solution comprising the first labeled antibody but not the second unlabeled antibody. After incubation under conditions permissive for binding of the first antibody to Notch2 NRR, excess unbound antibody is removed, and the amount of label associated with immobilized Notch2 NRR is measured. If the amount of label associated with immobilized Notch2 NRR is substantially reduced in the test sample relative to the control sample, then that indicates that the second antibody is competing with the first antibody for binding to Notch2 NRR.

In one aspect, antibodies of the invention can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

It is understood that any of the above assays may be carried out using an immunoconjugate of the invention in place of or in addition to an anti-Notch2 NRR antibody.

E. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

IV. EXAMPLES

The following are examples of methods and compositions of the invention. It is understood that various other embodiments may be practiced, given the general description provided above.

A. Materials and Methods

1. Generation of Anti-Notch2 NRR Antibodies

Library Sorting and Screening to Identify Anti-Notch2 NRR Antibodies

Human phage antibody libraries with synthetic diversities in the selected complementarity determining regions (H1, H2, H3, L3), mimicking the natural diversity of human IgG repertoire, were used for panning Fab fragments were displayed bivalently on the surface of M13 bacteriophage particles. (See Lee et al., *J. Mol. Biol.* 340:1073-1093 (2004).) Notch2 NRR fragments were expressed as secreted proteins fused to epitope tags (FLAG or 6×His) using the baculovirus expression vector system or 293T cells, purified to >90% purity using affinity chromatography and tested for lack of aggregation using light scattering. The sequences of the Notch2 NRR antigens were as follows:

```
FLAG-Human-Notch2-NRR-6xHis:
                                              (SEQ ID NO: 73)
KDDDDKGSGDVCPQMPCLNGGTCAVASNMPDGFICRCPPGFSGARCQSSC

GQVKCRKGEQCVHTASGPRCFCPSPRDCESGCASSPCQHGGSCHPQRQPP

YYSCQCAPPFSGSRCELYTAPPSTPPATCLSQYCADKARDGVCDEACNSH

ACQWDGGDCSLTMENPWANCSSPLPCWDYINNQCDELCNTVECLFDNFEC

QGNSKTCKYDKYCADHFKDNHCNQGCNSEECGWDGLDCAADQPENLAEGT

LVIVVLMPPEQLLQDARSFLRALGTLLHTNLRIKRDSQGELMVYPYYGEK

SAAMKKQRMTRRSLPGEQEQEVAGSKVFLEIDNRQCVQDSDHCFKNTDAA

AALLASHAIQGTLSYPLVSVVSESLTPERTEFGLVPRGSGHHHHHH

Mouse Notch2-NRR-FLAG:
                                              (SEQ ID NO: 74)
ADVCPQKPCLNGGTCAVASNMPDGFICRCPPGFSGARCQSSCGQVKCRRG

EQCIHTDSGPRCFCLNPKDCESGCASNPCQHGGTCYPQRQPPHYSCRCPP

SFGGSHCELYTAPTSTPPATCQSQYCADKARDGICDEACNSHACQWDGGD

CSLTMEDPWANCTSTLRCWEYINNQCDEQCNTAECLFDNFECQRNSKTCK

YDKYCADHFKDNHCDQGCNSEECGWDGLDCASDQPENLAEGTLIIVVLLP

PEQLLQDSRSFLRALGTLLHTNLRIKQDSQGALMVYPYFGEKSAAMKKQK

MTRRSLPEEQEQEQEVIGSKIFLEIDNRQCVQDSDQCFKNTDAAAALLAS

HAIQGTLSYPLVSVFSELESPRNARRAGSGDYKDDDDKENLYFQ
```

Nunc 96 well Maxisorp immunoplates were coated overnight at 4° C. with target antigen (10 μg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., *J. Immunol. Meth.* 284:119-132, 2004) and VH/VL (see Liang et al., *J. Mol. Biol.* 366: 815-829, 2007) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phage were amplified in *E. coli* XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to both human and murine Notch2 NRR. The variable regions of these clones were PCR sequenced to identify unique sequence clones.

The affinities of phage antibodies were ranked using spot competition ELISA. The phage antibody IC50 values were further determined using competitive phage-binding ELISA. Unique phage antibodies that bind both human and murine Notch2 NRR were chosen and reformatted to full length IgGs for evaluation in in vitro cell assay.

Clones of interest were reformatted into IgGs by cloning $V_L$ and $V_H$ regions of individual clones into the LPG3 and LPG4 vector respectively, transiently expressing in mammalian CHO cells, and purifying with a protein A column.

Construct Libraries for Affinity Improvement of Antibody D

Phagemid pW0703 (derived from phagemid pV0350-2b (Lee et al., *J. Mol. Biol* 340, 1073-1093 (2004)) displaying monovalent Fab on the surface of M13 bacteriophage) served as the library template for grafting light ($V_L$) and heavy ($V_H$) chain variable domains of Antibody D from the VH/VL library for affinity maturation. Stop codons were then incorporated in CDR-L3 of the library template. Soft randomization strategy was used for affinity maturation, which introduced a mutation rate of approximately 50% at the selected positions by using a poisoned oligonucleotide strategy with 70-10-10-10 mixtures of bases favoring the wild type nucleotides (Gallop et al., Journal of Medicinal Chemistry 37:1233-1251 (1994)). Specifically residues at positions 28-32 of CDR-L1, 50 and 53-55 of CDR-L2, 91-94 and 96 of CDR-L3, 28-35 of CDR-H1, 50-58 of CDR-H2, 95-100 of CDR-H3, were targeted. Three different libraries with combinations of soft-randomized CDR loops, L1/L2/L3, L3/H1/H2 and L3/H3, were also constructed.

Phage Sorting Strategy to Generate Affinity Improvement

For affinity improvement selection, phage libraries were subjected to plate sorting for the first round, followed by five rounds of solution sorting. The libraries were sorted against human and murine Notch2 NRR separately. At the first round of plate sorting, three libraries were sorted against target coated plate (NUNC Maxisorp plate) separately with phage input about 3 O.D./ml in 1% BSA and 0.05% Tween 20 for 2 hours at room temperature. For the following round of solution sorting, 1 O.D./ml phage propagated from the first round of plate sorting were incubated with 50 nM biotinylated target protein (the concentration is based on parental clone phage IC50 value) in 100 μl buffer containing 1% Superblock (Pierce Biotechnology) and 0.05% Tween20 for 30 minutes at room temperature. The mixture was further diluted 10× with 1% Superblock, and 100 μl/well was applied to neutravidin-coated wells (5 μg/ml) for 15 minutes at room temperature with gentle shaking to capture biotinylated target bound phage. The wells were then washed with PBS-0.05% Tween 20 ten times. To determine background binding, control wells containing phage with targets that were not biotinylated were captured on neutravidin-coated plates. Bound phage was eluted with 0.1N HCl for 20 minutes, neutralized by 1/10 volume of 1M Tris pH 11, titered, and propagated for the next round. Next, four more rounds of solution sorting were carried out together with two methods of increasing selection stringency. The first of which is for on-rate selection by decreasing biotinylated target protein concentration from 10 nM to 0.5 nM, and the second of which is for off-rate selection by adding excess amounts of non-biotinylated target protein (100~500 fold more) to compete off weaker binders either at room temperature. Also, the phage input was decreased (0.1~0.5 O.D/ml) to lower background phage binding.

High Throughput Affinity Screening ELISA (Single Spot Competition)

Colonies were picked from the sixth round sorting and grown overnight at 37° C. in 500 μl/well of 2YT media with 50 μg/ml carbenicillin and 1E10/ml KO7 in 96-well plate (Falcon). From the same plate, a colony of XL-1 infected parental phage was picked as control. 96-well Nunc Maxisorp plates were coated with 100 μl/well of human and murine Notch2 NRR protein (1 μg/ml) separately in PBS at 4° C. overnight or room temperature for 2 hours. The plates were blocked with 65 μl of 1% BSA for 30 min and 40 μl of 1% Tween 20 for another 30 minutes.

The phage supernatant was diluted 1:5 in ELISA (enzyme linked immunosorbent assay) buffer (PBS with 0.5% BSA, 0.05% Tween20) with or without 10 nM target protein in 100 μl total volume and incubated at least 1 hour at room temperature in an F plate (NUNC). 75 μl of mixture with or without target protein was transferred side by side to the target protein coated plates. The plate was gently shaken for 15 min to allow the capture of unbound phage to the target protein-coated plate. The plate was washed at least five times with PBS-0.05% Tween 20. The binding was quantified by adding horseradish peroxidase (HRP)-conjugated anti-M13 antibody in ELISA buffer (1:5000) and incubated for 30 minutes at room temperature. The plates were washed with PBS-0.05% Tween 20 at least five times. Next, 100 μl/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 μl 1M Phosphoric Acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation.

$$OD_{450nm}\text{ reduction}(\%)=[OD_{450nm}\text{ of wells with competitor})/(OD_{450nm}\text{ of well with no competitor})]*100$$

In comparison to the $OD_{450nm}$ reduction (%) of the well of parental phage (100%), clones that had the $OD_{450nm}$ reduction (%) lower than 50% for both the human and murine target were picked for sequence analysis. Unique clones were selected for phage preparation to determine binding affinity (phage IC50) against both human and murine Notch2 NRR by comparison with parental clones. The clones with the most affinity improvement were reformatted into human IgG1 and expressed in Mammalian cells.

Characterization of Anti-Notch2 NRR Antibodies (Biacore)

Binding affinities of anti-Notch2 NRR antibodies were measured by Surface Plasmon Resonance (SRP) using a BIAcore™-3000 instrument. Anti-Notch2 NRR human IgGs were captured by mouse anti-human IgG coated on the CM5 sensor chip to achieve approximately 200 response units (RU). For kinetics measurements, two-fold serial dilutions of human and mouse Notch2 NRR (3.9 nM to 500 nM) were injected in PBT buffer (PBS with 0.05% Tween 20) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

2. Generation of Anti-Notch1 NRR Antibodies

The generation and characterization of certain anti-Notch1 NRR antibodies have been previously described. See U.S. Patent Application Publication No. US 2009/0081238 A1.

3. ELISA

Anti-Flag antibody was used to capture Flag-Tagged NRR protein from all four Notch receptors in a black walled, high binding plate (Greiner). NRR antibody and E25 control antibodies were bound to the NRR proteins and washed away with PBS. An Alkaline Phosphate conjugated anti-human (H+L) secondary antibody (Jackson ImmunoResearch) was used to detect bound anti-NRR and E25. Unbound secondary was washed away and AP was detected with PNPP substrate (Pierce).

4. FACS

Expression plasmids were made in which either the Notch1 or Notch2 extracellular domain and trans-membrane domains were N-terminally myc-tagged and expressed under the control of a Tetracycline Response Element (TRE) upstream of a minimal CMV immediate early promoter. These plasmids were stably transfected into CHO-K1 cells (Clonetech), engineered to express a transactivator protein in the presence of Doxycycline that binds to and activates the TRE in the transfected plasmid. Cells were treated with 1 mg/mL doxycycline or vehicle for 48 hrs, and then stained with anti-NRR, anti-myc (9E10, Millipore) or E25 control antibodies and either goat anti-human Alexa 488 or Alexa 647 secondary antibodies (Invitrogen). After staining, cells were run on a FACScalibur machine (BD Biosciences) and 15000 events were collected and range gates were drawn to assess positively and negatively stained populations.

5. Notch Reporter Assay

NIH-3T3 cells either stably transfected with Notch 1 or transiently transfected with plasmids containing other Notch receptors were co-transfected with a Notch-responsive TP-1 (12× CSL) Firefly luciferase reporter and a constitutively active *Renilla* Luciferase reporter (pRL-CMV, Promega) to control for transfection efficiency. Cells are allowed to recover from the transfection from 6 hours to overnight. Treatments of antibodies and NIH-3T3 cells stably transfected with ligand are used to stimulate the receptor cells. After 20 hours, firefly and *Renilla* luciferase are measured with Dual Glo Luciferase Assay system (Promega). Eight replicates were analyzed for each condition by dividing the Firefly signal by the *Renilla* signal to control for transfection efficiency. The mean and standard deviation were calculated and values were normalized to calculated values for co-culture stimulated with NIH-3T3 cells without ligand transfected.

6. Epitope Mapping

Synthetic Notch1 and Notch2 NRR sequences were designed with unique restriction sites at junctions between the five domains of the NRR-LNR-A; LNR-B; LNR-C; HD-N; and HD-C—and produced by Blue Heron Technology (Bothell, Wash.). Swapping various domains between the two synthetic sequences, using the engineered restriction sites, generated chimeric NRR proteins. The chimeric clones were assembled in a modified pUC19 vector and transferred to a SEAP containing vector, pCSC.AP, for expression. AP-tagged NRR proteins were produced by transfection of 293T cells. After 72 hr culture, the conditioned media was collected, cleared by centrifugation, and tested for AP activity using the Phospha-Light System (Applied Biosystems, Bedford, Mass.). The AP activity in each sample was normalized and an ELISA was performed to test the ability of α-NRR1 or α-NRR2 to bind the chimeric NRR proteins. The ELISA was performed as follows: either α-NRR1 or α-NRR2 was captured by a plate bound α-Fc antibody in 96-well format and incubated with the conditioned media overnight. The plate was washed to remove unbound protein, and the captured protein was tested for AP activity using the Phospha-Light System. The resulting AP activity was used to quantify the capacity of each α-NRR antibody to bind specific chimeric proteins and infer important epitopes for binding.

7. HUVEC Fibrin Gel Bead Assay

HUVEC cells were grown on fibrin gel beads as previously described (Nakatsu et al., 2003). Cytodex 3 beads (Amersham Pharmacia Biotech) were coated with 350-400 HUVECs per bead in 2 ml EGM-2 medium (Clonetics). About 200 HUVEC coated beads were imbedded in fibrin clot in one well of 12-well tissue culture plate. $6\times10^4$ Detroit 551 fibroblast cells were plated on top of the clot and medium containing either 5 ug/ml anti-NRR1, 5 ug/ml anti-DLL4, 1 uM DBZ, or vehicle controls. Medium was changed every two days. After seven to nine days, fibrin gels were then fixed with 4% paraformaldehyde and endothelial cells were stained with anti-CD31 (R&D Systems AF806) using a FITC-conjugated secondary antibody for detection.

8. Neonatal Retinal In vivo Assay

CD1 neonates were injected i.p. at P1 and P3 with either 10 mg/kg of ragweed control or 20 mg/kg of Notch-1. Eyes were harvested at P5 and fixed with 4% PFA. The retinas were dissected out, blocked (5% BSA, 0.5% Triton X-100) for one hour followed by treatment for 10 min with 1M Sodium Citrate. Retinas were then incubation overnight at 4 C with biotinylated isolectin B4 (Sigma) and Ki67 antibody (NeoMarkers). Retinas were subsequently washed and stained with streptavidin Alexa 488 and goat anti-rabbit Cy3 in 1% BSA, 0.5% Triton X-100. Retinas were mounted flat and imaged using an epifluoresence microscope.

9. In Vivo Tumor Studies

The human tumor cell line Calu-6 and HM7 were grown in Ham's F12, low glucose DMEM 1:1 supplemented with 10% v/v FBS, 1% v/v penicillin/streptomycin, 2 mM L-Gln and 1 μg/ml Fungizone™ (Invitrogen™, CA). Cells were incubated at 37° C. in an atmosphere of 95% air/5% $CO_2$. For mouse xenograft experiments, tumor cells were suspended at a concentration of $1\times10^8$ or $1\times10^9$ cells/ml and injected (100 μl/mouse) subcutaneously into the dorsal flank of Balb-c nude mice (Harlan Sprague Dawley, IN). When tumors reached a volume of 400 $mm^3$, a cohort was randomly selected (n=10) as day-0 controls. The remaining mice were divided into groups of 10 mice, and phage antibody Anti-Notch1 were administered i.p. at the dose of 10 mg/kg twice weekly. The transplanted tumors were measured twice weekly along the longest axis and the perpendicular axis as described. For each day on which tumors were measured, the tumor volume for each mouse was calculated, and the tumor volume means from each control antibody (anti-Ragweed), anti-VEGF group were compared with the tumor volume mean of Anti-Notch1-treated mice by Dunnett's t test implemented in the JMPTM Statistical Analysis System (version 5.1 for Windows; SAS Institute, Cary, N.C.), at a level of $P<0.05$. Mice were killed when tumor volume reached 2,000 $mm^3$. Tumors were sectioned by cryostat to 7 microns, fixed with acetone and stained with DAPI (Invitrogen), hamster anti-CD31 (Serotech, Inc.) and an anti-hamster Cy3 secondary (Jackson Immunolabs). Slides were mounted with Fluorescent Mounting Medium (Dako). Images were taken with a Zeiss Axioskop2 Microscope and analyzed by ImageJ for area of DAPI stain and Cy3 staining Cy3 stain was divided by the area of DAPI stain to normalize to the number of cells present and the values were normalized to the anti-Ragweed treated tumor. All animal studies were conducted in accordance with Institutional Animal Care and Use Committee approved protocols.

10. Marginal Zone B Cell Analysis

Balb-c mice (Jackson) at 12 weeks old were injected IP twice per week for two weeks with 5 mg/kg of anti-gD, anti-NRR1 or anti-NRR2. Splenocytes were isolated from the mice and were stained for FACS with B220-PerCP, CD23-PE and CD21-FITC (BD Biosciences) as previously described (Saito, et al., Immunity, Vol. 18, 675-685, May 2003).

11. Histology and Immunohistochemistry of Mouse Intestine Tissue

Six groups of six, 10 week old, C57BL/6 mice (Jackson) were administered either MCT every other day, DBZ at 30 umol/kg every other day, Anti-NRR1 at 10, 2, or 0.4 mg/kg or Anti-gD control (HSV-1) at 10 mg/kg at Day 0, 2 and 6, or as otherwise indicated. Formalin-fixed and paraffin-embedded mouse small intestine tissues were sectioned at 3 micron thickness. Histochemical identification of intestinal cell types was performed with Alcian blue as recommended by the manufacturer (PolyScientific). For anti-Ki67 staining, sections were pretreated with Target Retrieval Solution (S1700, DAKO), and incubated with rabbit anti-Ki67 (1:200, clone SP6, Neomarkers). Secondary goat anti-rabbit at 7.5 μg/ml (Vector labs) was detected with the Vectastain ABC Elite Kit (Vector labs). Ki67 stained sections were counterstained with Mayer's haemotoxylin. For anti-lysozyme staining, sections were processed on the Discovery XT platform (Ventana Medical Systems, Inc.) using CC1m epitope recovery conditions, OmniMap-rabbit detection and Ventana haemotoxylin II/with bluing counterstain. For HES-1 staining, anti-rat HES-1 (clone NM1, MBL, International) was followed by TSA-HRP.

B. Results

1. Generation of Synthetic Antibodies that Specifically Target the Notch1 and Notch2 Negative Regulatory Regions To enable independent antagonism of Notch1 and Notch2 signaling in humans and mice, we used phage display to target the NRR and select for synthetic, human antibodies with the following qualities. First, each antibody was selected to potently inhibit its cognate target—Notch1 or Notch2—but not other Notch receptors. Second, the antibodies were selected for binding to human target sequences to enable therapeutic targeting. Third, in order to discover the biological consequences of systemically inhibiting Notch1 or Notch2 in vivo and to study the functions of these receptors in mouse models, the antibodies were co-selected for binding to the orthologous mouse sequences. Fourth, to avoid a human anti-antibody immune response, the complementarity determining regions were cloned into a human immunoglobulin framework.

Following this approach, we successfully isolated anti-Notch1 NRR and anti-Notch2 NRR antibodies with each of these desired properties. These antibodies have several advantages over "pan-Notch" inhibitors that target multiple Notch receptors, such as γ-secretase inhibitors. Because these antibodies distinguish individual Notch receptors, they can dissect the distinct functions of those individual receptors. Furthermore, pan-Notch inhibitors show potentially unwanted side effects in vivo due to the dual inhibition of both Notch1 and Notch2, and thus antibodies that are selective for either Notch1 or Notch2 may be more attractive candidates for therapeutic purposes. The anti-Notch1 NRR and anti-Notch2 NRR antibodies isolated according to the above approach are described and characterized in further detail below:

The isolation and characterization of anti-Notch NRR1 antibodies are discussed in U.S. Patent Application Publication No. US 2009/0081238 A1. One of the antibodies disclosed in that application, "Antibody A-2," was characterized with respect to its structure and certain biological activities. Certain studies discussed in that application are recapitulated herein. For convenience, "Antibody A-2" from U.S. Patent Application Publication No. US 2009/0081238 A1 is referred to herein as "anti-NRR1."

The isolation and characterization of anti-Notch2 NRR antibodies is described herein. An anti-Notch2 NRR antibody, called "Antibody D", was isolated. That antibody was affinity matured as described above, resulting in Antibody D-1, Antibody D-2, and Antibody D-3. FIG. 1 shows the HVR-H1, HVR-H2, and HVR-H3 sequences of Antibody D, Antibody D-1, Antibody D-2, and Antibody D-3. FIG. 2 shows the HVR-L1, HVR-L2, and HVR-L3 sequences of Antibody D, Antibody D-1, Antibody D-2, and Antibody D-3. FIG. 3 shows the heavy chain variable region sequences of Antibody D, Antibody D-1, Antibody D-2, and Antibody D-3. FIG. 4 shows the light chain variable region sequences of Antibody D, Antibody D-1, Antibody D-2, and Antibody D-3. For convenience, Antibody D-3 is referred to herein as "anti-NRR2."

Measurements of binding affinities using surface plasmon resonance (SPR) revealed that anti-NRR1 bound with similar and high affinities ($K_d$=3 nM) to purified NRR1 proteins of either mouse or human sequence. We observed a similar affinity ($K_d$=5 nM) to the NRR2 antigens in tests of anti-NRR2. Binding of both antibodies appeared highly specific for the cognate receptor; no binding to the human or mouse sequences of any of the other three non-targeted receptors was detected for either anti-NRR1 or anti-NRR2 using a variety of techniques, including SPR, enzyme-linked immunosorbent assay (ELISA) and fluorescence-activated cell sorting (FACS) (FIG. 9 and data not shown). For example, ELISA results showed that anti-NRR1 bound equally well to purified human and mouse Notch1-NRR proteins, with half-maximal binding observed at an antibody concentration of approximately 0.1 μg/ml. Anti-NRR1 did not detectably bind to purified human or mouse Notch2 NRR, Notch3-NRR or Notch4-NRR proteins, even at the highest antibody concentration tested (FIG. 9A, left panel), despite the fact that human Notch1-NRR and human Notch2 NRR sequences are 45% identical (FIG. 18). We observed similar results for anti-NRR2, which bound specifically to the Notch2 NRR proteins but not to the NRR proteins from the other Notch receptors (FIG. 9A, right panel).

To determine whether anti-NRR1 and anti-NRR2 also bind specifically to full-length receptors expressed on the surface of cells, we used fluorescence-activated cell sorting (FACS). We assessed binding to either Notch1 or Notch2, each carrying a myc epitope tag at the N-terminus to distinguish the transgenic Notch receptors from endogenously expressed Notch receptors (particularly Notch2, which was expressed by the K1-CHO cells). Receptor expression was induced in K1-CHO cells that were either left untransfected (FIG. 9B, Panels 1, 4, 7 and 10), transfected with myc-Notch1 (FIG. 9B, Panels 2, 5, 8 and 11) or transfected with myc-Notch2 (FIG. 9B, Panels 3, 6, 9 and 12). Binding of anti-NRR1 to myc-positive cells was observed in the myc-N1 cells (FIG. 9B, panel 2), but not in the K1-CHO parent cells (FIG. 9B, panel 1) and only following induction (FIG. 9B, compare panels 2 and 5), indicating that anti-NRR1 bound specifically to Notch1. In contrast, although myc-Notch2 expression was clearly induced in the myc-N2 cells (FIG. 9B, compare panels 3 and 6), anti-NRR1 did not bind to myc-Notch2 (FIG. 9B, compare panels 2 and 3). We performed a similar analysis using anti-NRR2 (FIG. 9B, panels 7-12), although this analysis was complicated by leaky expression of myc-Notch2 in the absence of induction (FIG. 9B, panels 6 and 12) and endogenous expression of hamster Notch2 in the K1-CHO line (FIG. 9B, compare panels 7 and 10 to panels 1 and 4). Nevertheless, anti-NRR2 significantly bound only to cells expressing myc-Notch2 after induction, consistent with specific binding to Notch2 (FIG. 9B, compare panel 9 to panels 8 and 12). Taken together, our binding results using purified NRR proteins as well as cell-surface expression of full-length receptors demonstrate that anti-NRR1 binds specifically to Notch1-NRR1 and not to Notch2 NRR, and likewise, that anti-NRR2 binds specifically to Notch2 NRR and not to Notch1-NRR. This specificity is further supported by the numerous structural and functional studies described below.

2. Anti-NRR1 and Anti-NRR2 Function as Potent and Specific Inhibitors of Notch1 and Notch2 Signaling In Vitro To assess whether the anti-NRR antibodies affected Notch signaling, we first used a co-culture assay that employed NIH-3T3 cell lines engineered to express Jag1, as the Notch ligand, or either Notch1 (FIG. 10A) or Notch2 (FIG. 10B) as the Notch receptor. The assays accurately reflected Notch signaling because a strong Notch reporter signal (Firefly luciferase) depended on the presence of both ligand- and receptor-expressing cells (FIGS. 10A and B, compare −Jag1 to +Jag1), and the reporter level was reduced to background when a GSI (γ-secretase inhibitor) was included (FIGS. 10A and B, compare DMSO to DAPT).

Addition of increasing amounts of anti-NRR1 inhibited signaling in the Notch1 cells, with complete inhibition observed at an antibody concentration between 80 and 400 ng/ml (FIG. 10A). A control human antibody failed to inhibit signaling (FIG. 10A, compare α-gD to α-NRR1 titration), as did numerous other antibodies directed to antigens other than Notch1 (data not shown). To further test whether this inhibitory activity reflected anti-NRR1 binding, we asked whether the addition of purified NRR1 antigen rescued signaling in the presence of an inhibitory concentration (80 ng/ml) of anti-NRR1 antibody, by competing for antibody binding to Notch1 expressed on the signaling cells. Addition of NRR1 but not NRR2 antigen (which appeared active and properly folded in other assays; see FIG. 10B) restored signaling to control levels, (FIG. 10A, compare 80 ng/ml α-NRR1+NRR1 to 80 ng/ml α-NRR1 alone and 80 ng/ml α-NRR1+NRR2). As a control, neither NRR1 nor NRR2 antigens affected signaling in co-cultures that contained a control antibody, confirming that the NRR fragments themselves have no direct effect on Notch signaling (FIG. 10A, α-gD+NRR1 and α-gD+NRR2). Using the Notch2 expressing cells to assay anti-NRR2 activity, we observed similar results for anti-NRR2 inhibition of Notch2 signaling (FIG. 10B). Both antibodies inhibited signaling induced through all of the Notch ligands that we have tested, namely Jag1, Jag2, D111 and D114 (FIG. 16 and data not shown). Taken together, these results demonstrate that anti-NRR1 and anti-NRR2 are potent paralog-specific inhibitors of signaling from Notch1 and Notch2, respectively.

3. Anti-NRR1 Inhibits Signaling Through Both of the Main Classes of Mutant Receptors Found in T-ALLs One mechanism through which Notch signaling has been shown to directly affect oncogenesis is through mutational activation of Notch1 signaling in T-ALL. In particular, Notch1 activating mutations in T-ALL fall into two broad categories: (1) those that truncate the PEST domain, thus stabilizing the ICD and increasing signaling in a ligand-dependent manner, and (2) those that destabilize the NRR, thus enabling ADAM cleavage and stimulating signaling in a ligand-independent manner. To test whether anti-NRR1 can abrogate signaling through such mutant receptors, we modified the co-culture assay to express Notch1-WT (Notch1 wild-type), Notch1-ΔPEST (Notch1 lacking the PEST domain), or Notch1-L1594P (Notch1 carrying the L1594P mutation in the heterodimerization (HD) domain of the NRR). As was observed for wild-type Notch1 signaling (FIG. 10C, top panel), anti-NRR1 completely inhibited ligand-dependent and -independent signaling through Notch1-ΔPEST and Notch1-L1594P (FIG. 10C, middle and bottom panels). Thus, anti-NRR1 antagonizes signaling through both classes of mutant receptors, including the L1594P mutation that falls within and destabilizes the same domain targeted by the antibody.

4. Anti-NRR1 and Anti-NRR2 Function as Potent and Specific Inhibitors of Notch1 and Notch2 Signaling In Vivo To determine whether anti-NRR1 and anti-NRR2 function as receptor-specific inhibitors in vivo, we investigated how the antibodies affected cell fate decisions for which genetic techniques had established a role for Notch1 or Notch2. Specifically, conditional inactivation of Notch1 or Notch2 previously revealed that Notch1 is key to determining a T versus B cell fate during lymphoid development, whereas Notch2 is required to generate splenic marginal zone B (MZB) cells. Consistent with a crucial function for Notch1 in T cell development, we found that treating mice with anti-NRR1, but not anti-NRR2, significantly reduced thymus weights (FIGS. 11A and B). Likewise, anti-NRR1, but not anti-NRR2, dramatically reduced the total number of cells in the thymus (FIG. 11B) and nearly completely inhibited the generation of CD4+/CD8+ double-positive T cells (FIG. 11C).

In contrast, the antibody effects were reversed when MZB cells were examined. Treatment with anti-NRR2 nearly eliminated MZB cells (0.97+/−0.45 compared to the control value of 6.61+/−0.25), reducing the population even more dramatically than did purified, recombinant lymphotoxin-β receptor (LTβR)-Fc fusion protein (3.48+/−0.06), which served as a positive control (FIG. 11D). This inhibitory effect was specific to anti-NRR2 because anti-NRR1 did not significantly reduce the MZB population (6.00+/−0.44) relative to the anti-gD control antibody (6.61+/−0.25; FIG. 11D). Taken together, these in vivo studies indicate that both antibodies are potent inhibitors of their respective targets that can induce biologically significant changes in cell fate decisions; furthermore, because anti-NRR1 affects the generation of T but not MZB cells whereas anti-NRR2 affects the generation of MZB but not T cells, each antibody functions specifically for its intended target in vivo.

5. A Co-Crystal Structure Reveals that Anti-NRR1 Bridges the LNR and HD-C Domains and Likely Stabilizes the NRR “Off” Conformation To elucidate the binding specificity of anti-NRR1 and anti-NRR2 and gain mechanistic insights into the antibody antagonist activity, we tested binding of both antibodies to a battery of chimeric NRR proteins. Specifically, we made chimeric NRRs by swapping each of the NRR subdomains (LNR-A, LNR-B, LNR-C, HD-N and HD-C) between Notch1 and Notch2, expressed these chimeras as secreted proteins fused to alkaline phosphatase for easy detection, and assayed binding of normalized amounts of each chimeric NRR to anti-NRR1 or anti-NRR2. Of the 26 chimeric NRRs that we expressed, 17 were efficiently detected as secreted proteins (FIG. 12A), 7 were weakly detected and 2 were not detected above background (FIG. 17), suggesting that most but not all of the chimeric NRRs were expressed, properly folded and secreted. Swapping the single LNR-A domain from NRR2 into the NRR1 backbone disrupted binding of anti-NRR1 (FIG. 12A, chimera BC.Hd and all others with LNR-A from NRR2), indicating that anti-NRR1 contacts with the LNR-A subdomain of NRR1 are essential for binding. In contrast, swapping the LNR-C and/or HD-N domains from NRR2 into NRR1 did not affect anti-NRR1 binding (FIG. 12A, chimeras AB.Hd, ABC.Hc and AB.Hc), demonstrating that neither of these domains is essential for binding specificity. Lastly, AB.Hc was the chimera with the fewest NRR1 subdomains that still supported full anti-NRR1 binding (although weak binding was observed to the AB chimera), suggesting that most, and perhaps all, of the contacts required for anti-NRR1 binding specificity are contained in the LNR-A, LNR-B and HD-C domains.

Characterization of anti-NRR2 revealed a binding pattern similar to that defined for anti-NRR1, albeit with some distinct differences. Swapping the LNR-A domain of NRR1 into the NRR2 backbone completely disrupted anti-NRR2 binding, whereas swaps of LNR-B or LNR-C had no effect; thus, as was the case for anti-NRR1, anti-NRR2 binding requires the LNR-A subdomain from Notch2. Likewise, the HD-C domain from Notch2 was also essential. Two different chimeras (C.Hn and BC) with only three subdomains from NRR2 supported full binding in this assay; both of these chimeras share the LNR-A and HD-C subdomains from NRR2 and, consistent with this observation, the chimera that contained only the LNR-A and HD-C subdomains from NRR2 supported weak but detectable binding to anti-NRR2. Thus, in defining the subdomains that determine anti-NRR2 binding specificity, the domain swap experiments: (a) reveal that the LNR-A and HD-C are most important (necessary and partially sufficient for binding specificity) and (b) suggest that antibody-NRR2 contacts in LNR-B and HD-N may also play a role.

Figure 12B:
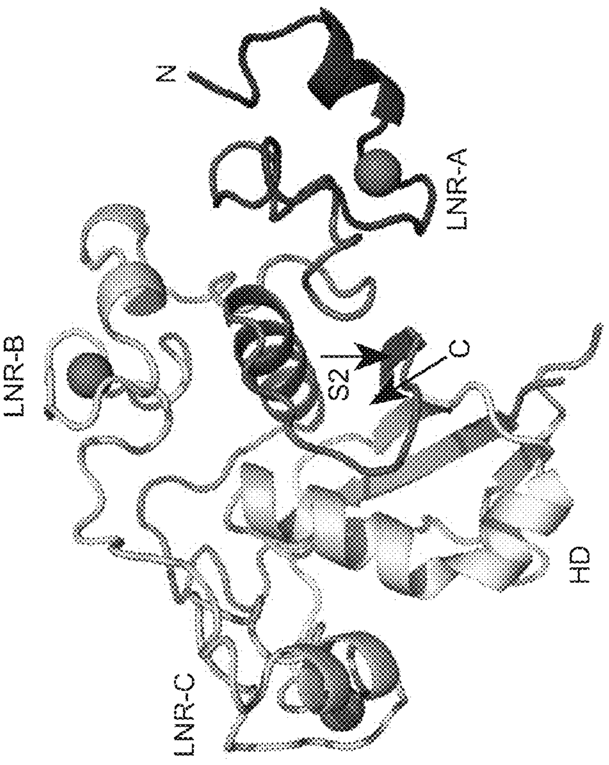
Figure 12C:
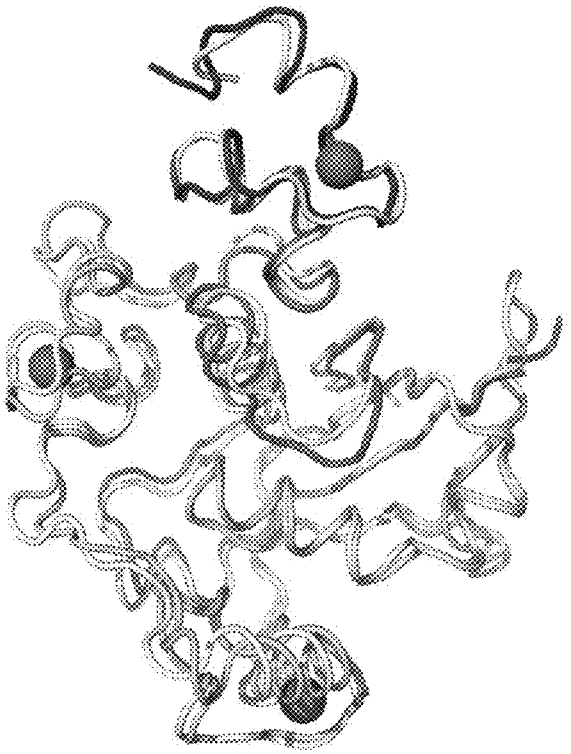

To better understand the molecular basis of the antagonistic activity of anti-NRR1, we determined the 2.2 Å crystal structure of the Fab fragment of the antibody bound to human NRR1. This structure revealed that NRR1 forms a compact structure very similar to that of human NRR2, with three $Ca^{2+}$ binding LNR modules wrapped around the core HD domain (FIGS. 12B and C). The structure reveals that the apparent affect of Fab binding is to stabilize the LNR-HD interactions such that S2 is not accessible for cleavage, thus keeping the Notch1 signaling cascade quiescent. This interpretation is supported by the observation that the Fab does not directly occlude the S2 site but instead binds at the interface between the HD, LNR-A and LNR-B domains (FIG. 12D), consistent with the domain swap experiments (FIG. 12A). This interface buries ~2000 $Å^2$ of solvent-accessible surface area, equally divided between the fab and NRR1. The Fab heavy chain contacts LNR-B, the final helix in the HD-C domain, and the periphery of LNR-A. CDR H3 nestles into the interface between LNR-B and HD. In particular, R99 from H3 forms a hydrogen bond to the backbone carbonyl of Phe1501 from LNR-A while the aliphatic portion of the side chain interacts with L1710 from the HD domain. The light chain accounts for ~40% of the buried surface area contributed by the Fab and contacts the connecting loop prior to the final helix in the HD domain as well as LNR-A.

Figure 12D:
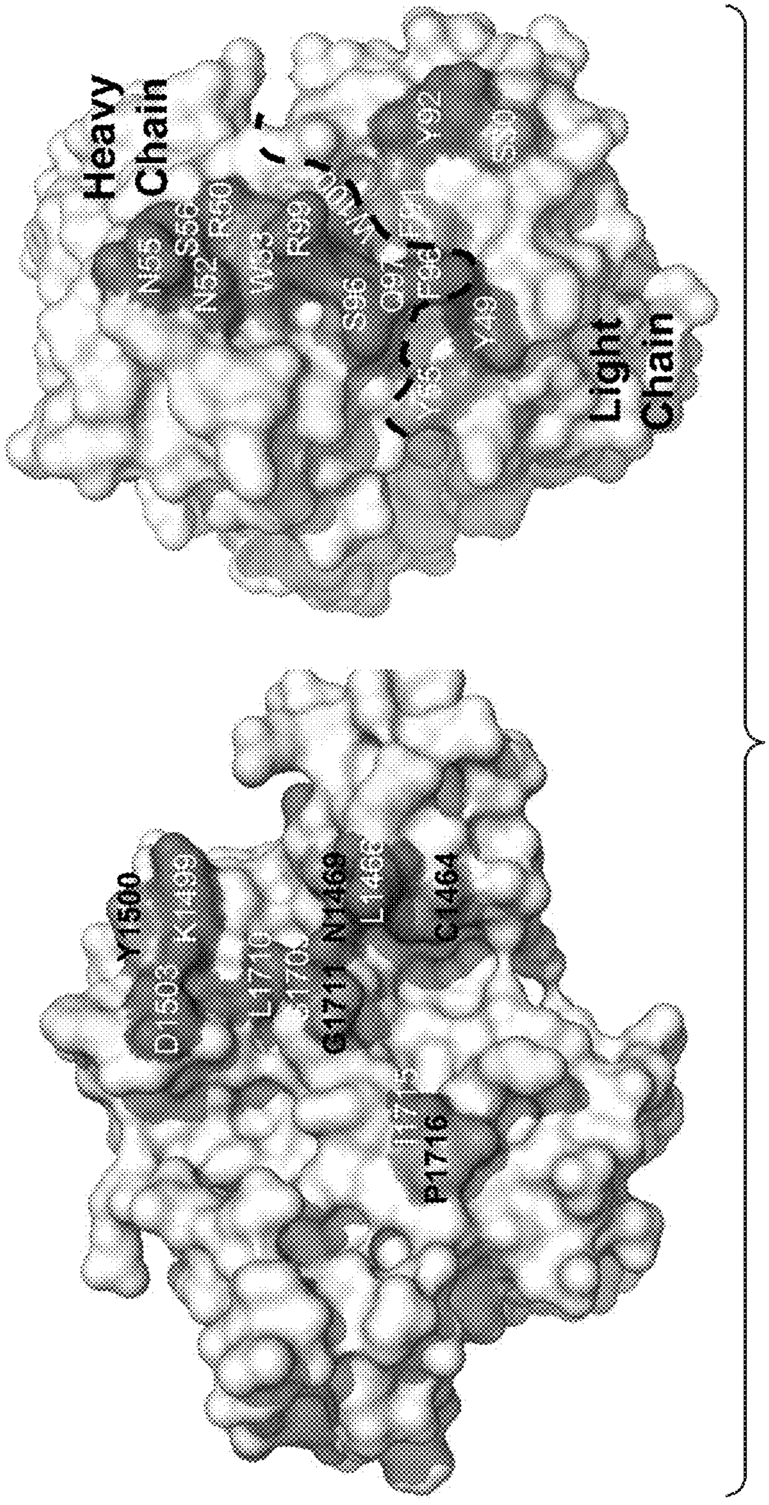

This structure also reveals the basis of Fab specificity for Notch1 over Notch2. Despite the ~45% sequence identity between the NRR domains of Notch1 and Notch2, most of the residues involved in the interface are distinct between the two proteins. For instance, of the 21 NRR residues that bury at least 25% of solvent accessible surface area on binding Fab, only six are identical in Notch1 and Notch2. These six residues contribute less than a quarter of the surface area in the Fab epitope and are distributed throughout the epitope (FIGS. 12D and 18).

6. Selective Inhibition of Notch1 Signaling Deregulates Angiogenesis

To begin to exploit Notch receptor-specific antibodies to define the functional importance of individual receptors in vivo, we first asked whether selectively blocking Notch1 signaling with anti-NRR1 would disrupt mammalian angiogenesis. Numerous reports indicate that the Notch pathway functions downstream of vascular endothelial growth factor (VEGF) and plays a key role in angiogenesis by regulating endothelial cell fate choice between tip and stalk cells. Experiments using a variety of genetic and biochemical tools, including D114-specific blocking antibodies, have established Dll4 as the key Notch ligand involved in Notch angiogenic signaling, although two Notch receptors, Notch1 and Notch4, have been implicated as receptors for Dll4 in angiogenesis.

We first tested whether selective inhibition of Notch1 affected endothelial sprouting in vitro. Human umbilical vein endothelial cells (HUVECs) co-cultured with human skin fibroblasts generate sprouts with lumen-like structures. Consistent with previous work, we found that pan-Notch inhibition using DBZ, an inhibitor of γ-secretase, as well as selective antibody blocking of Dll4 increased both the number and length of endothelial cell sprouts. Importantly, selective blocking of Notch1 signaling using anti-NRR1 generated a similar phenotype (FIGS. 13A and 13B).

To determine whether anti-NRR1 affects angiogenesis in vivo, we used a model based on development of retinal vasculature in mouse neonates. Systemic delivery of anti-NRR1 dramatically disrupted development of the retinal vasculature in treated neonate mice (FIG. 13C). Relative to treatment with a control anti-ragweed antibody, anti-NRR1 treatment generated a dense, compact and seemingly tangled vascular network (FIG. 13C, compare panels I and III with panels II and IV, respectively). This increased accumulation of endothelial cells correlated with increased proliferation, as assessed by labeling with the Ki67 proliferation marker (FIG. 13C, compare panels V and VI). These observations, including increased vascular density, endothelial cell accumulation and increased proliferation, all closely mimic those found following inhibition of Dll4 or γ-secretase using this same neonate model (data not shown) and are consistent with results from other studies, including analysis of tumor vasculature (FIGS. 13D and 13E) and the mouse corneal pocket assay (data not shown). Our results demonstrate not only that anti-NRR1 possesses potent biological activity but also that inhibition of Notch1 alone, as opposed to Notch4 or a combination of Notch1 and Notch4, is sufficient to dramatically disrupt mammalian angiogenesis.

Figure 14A:
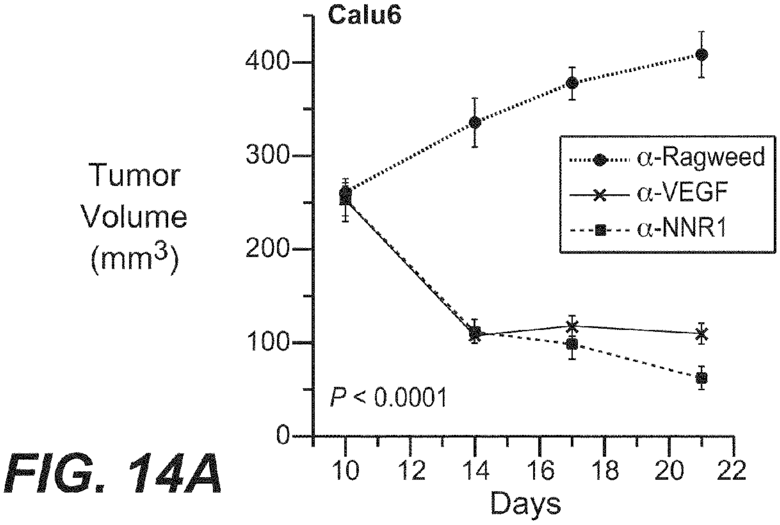
Figure 14B:
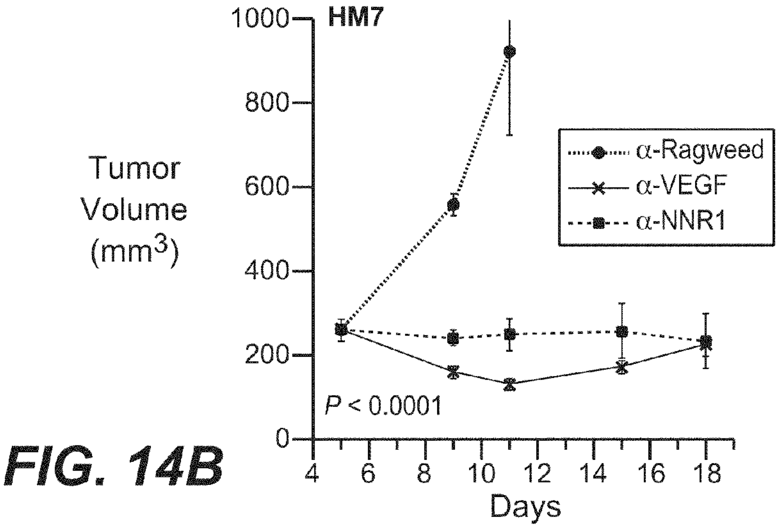
Figure 14C:
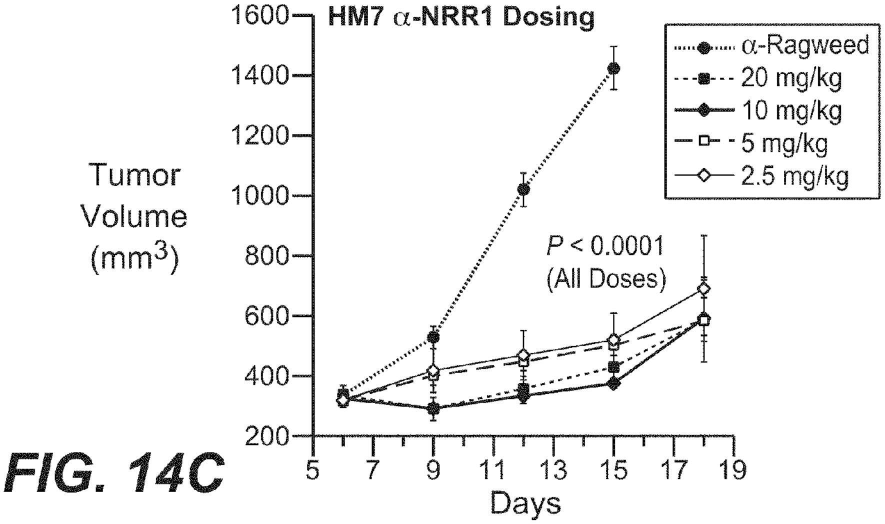

7. Selective Antibody Blocking of Notch1 Inhibits Tumor Growth in Preclinical Models To determine whether selectively blocking Notch1 using anti-NRR1 would be sufficient to inhibit tumor growth, we used preclinical tumor models and compared growth of established tumors following treatment with anti-NRR1, anti-VEGF or anti-ragweed antibodies. In both the Calu6 and HM7 models, the groups treated with anti-NRR1 showed a significant decrease in tumor size relative to the control groups, even at the first time points examined, three to four days after the initial dose (FIGS. 13A-C). In the Calu6 model, the anti-NRR1 group showed a decrease in tumor size, from approximately 250 $mm^3$ to less than 100 $mm^3$, similar to the decrease observed in the anti-VEGF group; in contrast, tumors in the anti-ragweed control group grew to a size greater than 400 $mm^3$ (FIG. 14A). We observed similar results using the aggressively growing HM7 model; anti-NRR1 treatment caused tumor size to remain static (FIG. 14B) or nearly static (FIG. 14C) over 12-13 days, a dramatic difference relative to the six-day growth from 250 $mm^3$ to greater than 900 $mm^3$ that was observed in the control group (FIGS. 14B and 5C). We observed similar inhibition of tumor growth using a range of anti-NRR1 dose concentrations, between 20 mg/kg and 2.5 mg/kg, although the 10 and 20 mg/kg groups showed a trend towards stronger inhibition relative to the 2.5 and 5 mg/kg groups (FIG. 14C).

Figure 14D:
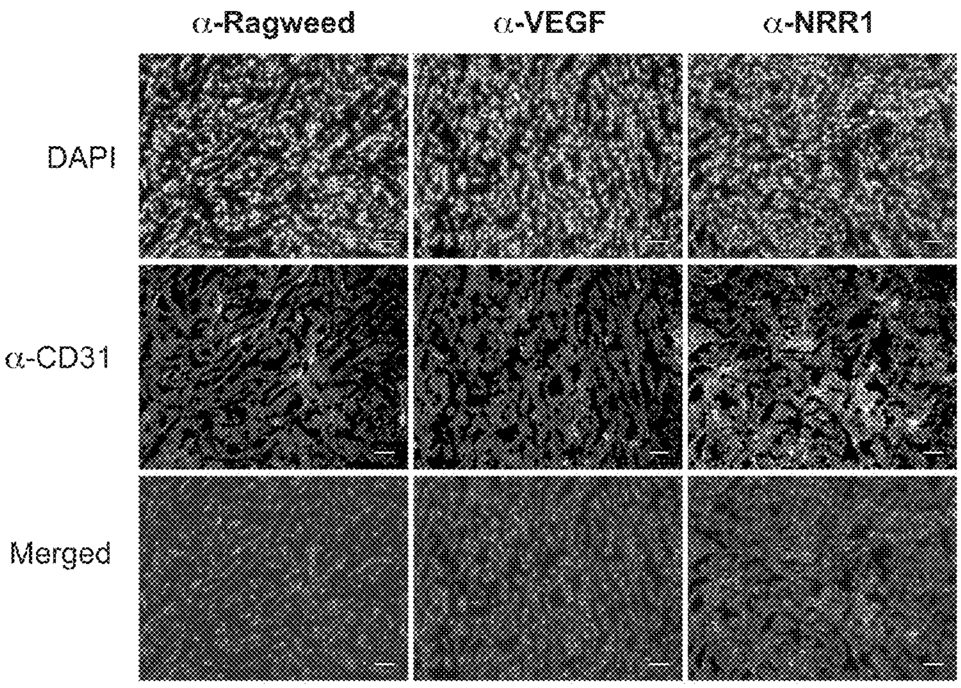
Figure 14E:
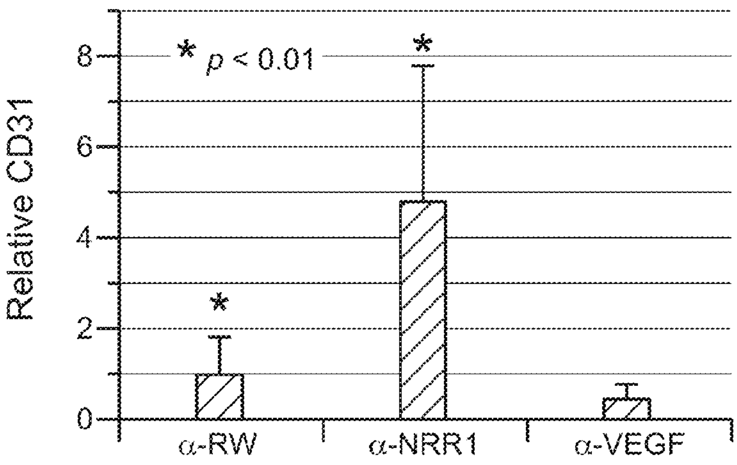

We investigated the Calu6 or HM7 tumor models because their response to anti-angiogenic agents has been well documented. To directly test whether anti-NRR1 disrupted angiogenesis in the Calu6 model, we examined the vasculature in representative tumor sections from mice in the three treatment groups. By normalizing staining of CD31, an endothelial cell marker, to the staining of DNA, using DAPI, we found that anti-NRR1 significantly increased CD31 staining relative to the other groups (FIG. 14D). This increase was statistically significant ($p<0.01$), and was consistently observed over multiple images (FIG. 14E). In contrast and as expected, anti-VEGF caused a reduction in CD31 staining (FIGS. 14D and 14E). The results from selective blocking of Notch1 thus mirror those reported for selective blocking of Dll4, which similarly leads to an increase in tumor CD31 staining as well as the generation of poorly functioning tumor vasculature. Taken together, these results suggest that the anti-tumor effects exerted by anti-NRR1 in the Calu6 and HM7 models primarily reflect a disruption in tumor angiogenesis.

8. Antibody Inhibition of both Notch1 and Notch2 has Marked Effects on Intestinal Cell Fate Gamma-secretase inhibitors (GSIs), which are pan-Notch inhibitors that inhibit multiple Notch receptors, cause weight loss and intestinal goblet cell metaplasia, reflecting the role that Notch plays in determining cell fate by maintaining proliferation of intestinal crypt progenitor cells and prohibiting differentiation to a secretory cell fate. (See van Es et al., *Nature* 435:959-963 (2005).) Moreover, genetic studies using conditional Notch knockout mice suggest that disruption of both Notch1 and Notch2 is required to cause intestinal goblet cell metaplasia. (See Riccio et al., *EMBO Rep.* 9:377-383 (2008).) We used anti-NRR1 and anti-NRR2 to determine the effects of selective inhibition of Notch1 or Notch2, or both, on weight loss and intestinal cell differentiation.

Mice treated with anti-NRR1 displayed a mild decrease in overall body weight during the course of antibody dosing. In a first experiment directly comparing anti-NRR1 and anti-NRR2, we found that anti-NRR1 caused a 5% decrease in total body weight, in contrast to the weight gains observed in the anti-NRR2 as well as the anti-gD and anti-LTβR-Fc control groups (FIG. 15A). In a second experiment, selective inhibition of Notch1 or Notch2 using anti-NRR1 or anti-NRR2, respectively, resulted in little or no effect on weight. The results of that experiment are depicted in FIG. 24A, in which mice were dosed with 5 mg/kg anti-NRR1 (squares), anti-NRR2 (triangles), or a control antibody ("α-gD", diamonds) on the days indicated by arrows. However, mice treated with both anti-NRR1 and anti-NRR2 ("X"s in FIG. 24A) lost nearly 20% of their starting body weight by as early as day 7.

We investigated whether the subtle weight loss resulting from anti-NRR1 treatment alone, or the more dramatic weight loss resulting from treatment with both anti-NRR1 and anti-NRR2, reflected changes in intestinal cell fate determination. After dosing mice with anti-NRR1 or anti-gD or DBZ as controls, sections of the large (FIG. 19) and small intestines were analyzed at day 2 (FIG. 20) and day 7 (FIG. 15B) using a variety of histochemical stains. DBZ had the same effects as previously described for GSIs (FIG. 15B, DBZ column) inhibition of Hes1 expression correlated with a decrease in progenitor cell proliferation (as shown by Ki-67 staining) and a dramatic expansion of the goblet cell population (as shown by Alcian Blue staining of mucin). Lysozyme staining also suggested that DBZ increased the numbers and/or activity of Paneth cells, a second secretory cell population (FIG. 15B), a suggestion that was further supported using Azure A-Eosin B staining for Paneth cell granules (data not shown). Anti-NRR1 at 10 mg/kg induced intestinal changes indistinguishable from those induced by DBZ (FIG. 15A, compare DBZ 30 μmol/kg to α-NRR110 mg/kg). These intestinal changes depended on the concentration of anti- NRR1, such that significant cell fate changes were observed using 10 mg/kg and 2.0 mg/kg but few, if any, notable changes were observed using 0.4 mg/kg. The large intestine responded similarly to DBZ and anti-NRR1 treatment: both treatments significantly reduced Notch signaling (FIG. 19, Hes1 staining), blocked progenitor cell proliferation (FIG. 19, Ki-67) and increased goblet cell numbers (FIG. 19, Alcian Blue and H&E). The intestinal cell fate changes were only weakly detectable at an early time point, day 2 of this study (FIG. 20; note the slight but detectable changes, caused by both DBZ and anti-NRR1, observed in Ki-67 and Alcian Blue staining).

Figure 24B:
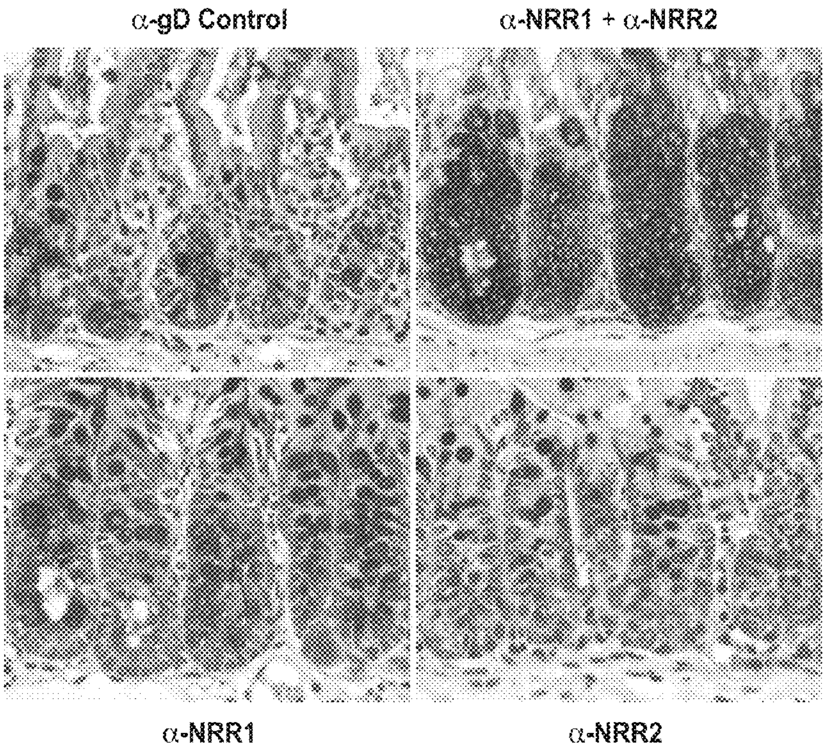

To determine whether inhibition of Notch2 signaling might similarly affect intestinal cell fate determination, we directly compared the effects of anti-NRR1 and anti-NRR2 on the large (data not shown) and small intestines (FIG. 15C, showing Alcian Blue and Ki-67 staining, and FIG. 24B, showing Alcian Blue staining). Whereas anti-NRR1 caused goblet cell metaplasia that coincided with a decrease in Ki-67 expression in the crypt progenitors, anti-NRR2 did not cause any detectable effects (FIGS. 15C and 24B, compare anti-NRR2 to anti-gD control). Because anti-NRR1 and anti-NRR2 function as potent and specific inhibitors of Notch1 and Notch2 signaling, respectively, both in vivo (FIG. 11) and in vitro (FIGS. 9, 10 and 21), these results strongly suggest that selective inhibition of Notch1, but not Notch2, is sufficient to alter intestinal cell fate determination.

The effect of inhibiting both Notch1 and Notch2 on intestinal cell fate determination was also investigated. FIG. 22 shows synergistic effects of anti-NRR1 and anti-NRR2 on altered intestinal cell differentiation. Female Balb/c mice were dosed with 5 mg/kg anti-NRR1, 5 mg/kg anti-NRR2 or 5 mg/kg anti-NRR1 plus 5 mg/kg anti-NRR2 on days 0, 4, 7 and 11. The intestines were harvested and stained with H&E to reveal the crypt morphology. For mice treated with anti-NRR1 or anti-NRR2 alone, the intestines were harvested on day 12; for mice treated with both antibodies together, the intestines were harvested on day 6 because the mice in this group were rapidly losing weight. The analysis of the intestines indicated that the antibody combination resulted in a more severe phenotype than that observed following treatment with anti-NRR1 alone, suggesting that Notch1 and Notch2 function together and partially redundantly in the mammalian intestine. Further experimentation confirmed this observation. As shown in FIG. 24B, intestines from mice treated with anti-NRR1 and anti-NRR2 showed severe goblet cell metaplasia. Although treatment with anti-NRR1 alone was sufficient to induce some goblet cell metaplasia, the effect of anti-NRR1 alone was mild relative to the effect of both anti-NRR1 and anti-NRR2 in combination.

Taken together, the results indicate that Notch1 and Notch2 function redundantly in intestinal cell differentiation, although potent inhibition of Notch1 but not Notch2 is sufficient to reveal a partial phenotype. We hypothesize that our ability to detect this partial phenotype, not previously reported in genetic studies, reflects that anti-NRR1 provides a more uniform and potent inhibition of Notch1 signaling throughout cells of the crypt than can be achieved following conditional gene knockout, which may be incomplete. Importantly, by significantly reducing or avoiding the goblet cell metaplasia that is a hallmark of general Notch inhibition, the Notch1- and Notch2-specific antibody inhibitors reported herein represent a clear breakthrough over existing pan-Notch inhibitors such as GSIs.

9. Rescue of Anti-NRR1 Intestinal Phenotype

FIG. 23 shows that dexamethasone at least partially rescues the intestinal phenotype caused by anti-NRR1. Antibodies were administered intraperitoneally (IP) into female NCR.nude mice (three mice per group) as follows:

Group A) Vehicle combination, MCT, once daily, anti-gD control antibody at 4 mg/kg, every fourth day (not shown in figure);

Group B) Dexamethasone, 90 mg/kg, daily (not shown in figure);

Group C) Anti-NRR1, 4 mg/kg, every fourth day;

Group D) Dexamethasone, 90 mg/kg, daily, and Anti-NRR1, 4 mg/kg, every fourth day.

The vehicle was 0.5% (w/v) hydroxypropylmethylcellulose (Methocel E4M) and 0.1% (w/v) Tween 80 in water (MCT), previously shown not to cause adverse clinical effects.

Intestines were harvested on day 9 and stained with anti-Ki67 (proliferation marker) and alcian blue (for mucin). This experiment revealed that mice treated with the dexamethasone plus anti-NRR1 combination displayed a milder intestinal phenotype relative to mice treated with anti-NRR1 alone, thus suggesting that dexamethasone protects the intestine from anti-NRR1-induced changes in differentiation.

10. Anti-NRR2Suppresses Growth of Melanoma Cell Lines

The effect of anti-NRR1 and anti-NRR2 on the growth of melanoma cell lines was investigated. Human melanoma cell lines SK23 and LOX-IMVI were plated in medium containing 2% FBS at low density (4000 cells/well for SK23, 2500 cells/well for LOX-IMVI) in 96 well plates that were coated without (−jag-1) or with Jagged-1 ligand (+jag-1) (R&D Systems, Minneapolis, Minn.). Anti-NRR1 (20 mg/ml), anti-NRR2 (20 mg/ml), or gamma-secretase inhibitor (GSI) DAPT (5 μM) was added to the cultures and re-added every other day thereafter. An equal volume of DMSO served as the vehicle control, whereas an equal concentration of anti-gD HuB6 phage antibody served as the isotype control antibody. Cell Titer Glo assays (Promega, Madison, Wis.) were performed six days after plating. The results are shown in FIGS. 25A and 25B (anti-NRR1 and anti-NRR2 are referred to as "anti-N1" and "anti-N2"). In FIGS. 25A and 25B, cell viability (y-axis) is expressed relative to the values from the DMSO vehicle, −jag-1 control wells. Both melanoma cell lines showed a decrease in viability in response to GSI treatment (especially in the presence of Jag1 ligand) and anti-NRR2 treatment, but not anti-NRR1 treatment.

11. Anti-NRR2Suppresses Growth of Diffuse Large B-Cell Lymphoma In Vitro

Diffuse large B-cell lymphoma (DLBCL) is the most common type of non-Hodgkin's lymphoma. A recent study of cancer cells from patients with DLBCL indicated that approximately 8% of patients carry a PEST domain mutation in Notch2, a mutation predicted to prolong Notch2 signaling following ligand activation. (See Lee et al., *Cancer Sci.* 100: 920-926, 2009.) However, how DLBCL cells would respond to Notch2 inhibition was not known. Therefore, we investigated the effect of anti-NRR2 on five DLBCL cell lines. The DLBCL lines listed on the right of FIG. 26 were grown in replicates for three days in wells of a 384-well plate. The cell cultures included the indicated concentrations of anti-NRR2 (referred to as "anti-Notch2" in FIGS. 26 and 27), which corresponded to three-fold serial dilutions starting at 10 μg/ml. Growth was assessed using Cell Titer Glo assays (Promega), plotted as the percentage of cell viability relative to treatment with an isotype control antibody. The data points in FIG. 26 represent average values obtained from individual wells for each cell line at the indicated antibody concentrations. As shown in FIG. 26, growth of one of the cell lines, "DB," was strongly inhibited by treatment with anti-NRR2.

FIG. 27 shows growth of the DB cell line over time. The DB line was grown in wells of a 12-well plate, and the cultures were treated with DMSO, the gamma-secretase inhibitor DAPT, anti-gD isotype control antibody or anti-NRR2 at the indicated concentrations. Growth was assessed by counting viable cells (Vi-CELL, Beckman Coulter, Fullerton, Calif.) at days 2, 3 and 5 after inoculating and treating the cultures. Values represent the mean of measurements from three independent cultures, plus/minus the standard deviation. FIG. 27 shows that anti-NRR2 suppresses the growth of the DB DLBCL cell line in vitro.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. A monoclonal antibody that binds to Notch2 negative regulatory region (NRR) and inhibits Notch2 activity, wherein the antibody binds both human and mouse Notch2 NRR with a Kd of ≦10 nM.

2. The antibody of claim 1, wherein the antibody does not significantly bind to a Notch family member other than Notch2.

3. The antibody of claim 2, wherein the antibody does not bind to Notch1.

4. A monoclonal antibody that binds to Notch2 NRR, wherein the antibody comprises:

(a) a heavy chain hypervariable region (HVR-H) 1 comprising the amino acid sequence of SEQ ID NO:3;

(b) an HVR-H2 comprising the amino acid sequence of SEQ ID NO:4;

(c) an HVR-H3 comprising the amino acid sequence of SEQ ID NO:5;

(d) a light chain hypervariable region (HVR-L) 1 comprising the amino acid sequence of SEQ ID NO:10;

(e) an HVR-L2 comprising the amino acid sequence of SEQ ID NO:14; and (f) an HVR-L3 comprising the amino acid sequence of SEQ ID NO:19.

5. The antibody of claim 4, wherein the antibody comprises an HVR-H1 comprising the amino acid sequence of SEQ ID NO:1 or 2; an HVR-L1 comprising the amino acid sequence of SEQ ID NO:6, 7, 8 or 9; an HVR-L2 comprising the amino acid sequence of SEQ ID NO:11, 12 or 13; and an HVR-L3 comprising the amino acid sequence of SEQ ID NO:15, 16, 17 or 18.

6. The antibody of claim 5, wherein the HVR-H1 comprises the amino acid sequence of SEQ ID NO:1, the HVR-L1 comprises the amino acid sequence of SEQ ID NO:6, the HVR-L2 comprises the amino acid sequence of SEQ ID NO:11, and the HVR-L3 comprises the amino acid sequence of SEQ ID NO:15.

7. The antibody of claim 5, wherein the HVR-H1 comprises the amino acid sequence of SEQ ID NO:2, the HVR-L1 comprises the amino acid sequence of SEQ ID NO:7, the HVR-L2 comprises the amino acid sequence of SEQ ID NO:11, and the HVR-L3 comprises the amino acid sequence of SEQ ID NO:16.

8. The antibody of claim 5, wherein the HVR-H1 comprises the amino acid sequence of SEQ ID NO:2, the HVR-L1 comprises the amino acid sequence of SEQ ID NO:8, the HVR-L2 comprises the amino acid sequence of SEQ ID NO:12, and the HVR-L3 comprises the amino acid sequence of SEQ ID NO:17.

9. The antibody of claim 5, wherein the HVR-H1 comprises the amino acid sequence of SEQ ID NO:2, the HVR-L1 comprises the amino acid sequence of SEQ ID NO:9, the HVR-L2 comprises the amino acid sequence of SEQ ID NO:13, and the HVR-L3 comprises the amino acid sequence of SEQ ID NO:18.

10. The antibody of claim 4, further comprising at least one framework selected from a human variable heavy (VH) Acceptor 2 framework and a human variable light (VL) kappa subgroup I consensus framework.

11. The antibody of claim 4, wherein the antibody comprises a heavy chain variable domain having at least 90% sequence identity to an amino acid sequence selected from SEQ ID NO:20-21 and a light chain variable domain having at least 90% sequence identity to an amino acid sequence selected from SEQ ID NO:22-25.

12. The antibody of claim 11, wherein the antibody comprises a heavy chain variable domain having at least 90% sequence identity to the amino acid sequence of SEQ ID NO:20 and a light chain variable domain having at least 90% sequence identity to the amino acid sequence of SEQ ID NO:22.

13. The antibody of claim 12, wherein the heavy chain variable domain comprises the amino acid sequence of SEQ ID NO:20, and the light chain variable domain comprises the amino acid sequence of SEQ ID NO:22.

14. The antibody of claim 11, wherein the antibody comprises a heavy chain variable domain having at least 90% sequence identity to the amino acid sequence of SEQ ID NO:21 and a light chain variable domain having at least 90% sequence identity to an amino acid sequence selected from SEQ ID NOs:23-25.

15. The antibody of claim 14, wherein the heavy chain variable domain comprises the amino acid sequence of SEQ ID NO:21, and the light chain variable domain comprises an amino acid sequence selected from SEQ ID NOs:23-25.

16. The antibody of claim 15, wherein the heavy chain variable domain comprises the amino acid sequence of SEQ ID NO:21, and the light chain variable domain comprises the amino acid sequence of SEQ ID NO:23.

17. The antibody of claim 15, wherein the heavy chain variable domain comprises the amino acid sequence of SEQ ID NO:21, and the light chain variable domain comprises the amino acid sequence of SEQ ID NO:24.

18. The antibody of claim 15, wherein the heavy chain variable domain comprises the amino acid sequence of SEQ ID NO:21, and the light chain variable domain comprises the amino acid sequence of SEQ ID NO:25.

19. The antibody of claim 4, wherein the antibody is an IgG1 antibody.

20. The antibody of claim 1, wherein the antibody binds to the same epitope as an antibody selected from Antibody D, Antibody D-1, Antibody D-2, or Antibody D-3.

21. The antibody of claim 20, wherein the antibody binds to a polypeptide comprising the Lin 12/Notch Repeat (LNR)-A domain and the heterodimerization domain (HD)-C domain of Notch2.

22. The antibody of claim 1, wherein the antibody is an antibody fragment selected from a Fab, Fab'-SH, Fv, scFv, or (Fab')2 fragment.

23. The antibody of claim 1, wherein the antibody is human, humanized, or chimeric.

24. The antibody of claim 1, wherein affinity is determined by a radiolabeled antigen binding assay or an enzyme linked immunosorbent assay.

25. The antibody of claim 1, wherein affinity is determined by surface Plasmon resonance.

26. The antibody of claim 1, wherein the antibody binds both human and mouse Notch2 NRR with a Kd of 5 nM.

27. A method of inhibiting Notch2 activity, the method comprising exposing a cell that expresses Notch2 to the antibody of claim 1.

28. A method of treating a disorder associated with increased expression or activity of Notch2, the method comprising administering to a subject in need thereof an effective amount of the antibody of claim 1.

29. The method of claim 28, wherein the disorder associated with increased expression or activity of Notch2 is a B-cell malignancy.

30. The method of claim 28, wherein the disorder associated with increased expression or activity of Notch2 is melanoma.

31. The method of claim 28, wherein the disorder is a cancer.

32. The method of claim 28, wherein the antibody comprises:

(a) a heavy chain hypervariable region (HVR-H) 1 comprising an amino acid sequence of SEQ ID NO:3;

(b) an HVR-H2 comprising the amino acid sequence of SEQ ID NO:4;

(c) an HVR-H3 comprising the amino acid sequence of SEQ ID NO:5;

(d) a light chain hypervariable region (HVR-L) 1 comprising an amino acid sequence of SEQ ID NO:10;

(e) an HVR-L2 comprising an amino acid sequence of SEQ ID NO:14; and (f) an HVR-L3 comprising an amino acid sequence of SEQ ID NO:19.

33. The method of claim 32, wherein the antibody comprises a heavy chain variable domain having at least 90% sequence identity to the amino acid sequence of SEQ ID NO:21 and a light chain variable domain having at least 90% sequence identity to an amino acid sequence selected from SEQ ID NOs:23-25.

34. The method of claim 33, wherein the heavy chain variable domain comprises the amino acid sequence of SEQ ID NO:21, and the light chain variable domain comprises the amino acid sequence of SEQ ID NO:25.

35. The method of claim 28, wherein the antibody is administered with at least one therapeutic agent.

36. The method of claim 35, wherein the therapeutic agent is a chemotherapeutic agent.

37. The method of claim 35, wherein the antibody and the therapeutic agent are separately administered to the subject.

38. A monoclonal antibody that binds to Notch2 negative regulatory region (NRR), wherein the antibody inhibits Notch2 signaling and has at least one of the following activities: (i) reduces the number of splenic marginal zone B cells in vivo; (ii) decreases melanoma cell viability in vitro; or (iii) suppresses growth of diffuse large B-cell lymphoma cells in vitro.

39. The antibody of claim 38, wherein the antibody reduces the number of splenic marginal zone B cells in vivo.

40. The antibody of claim 39, wherein the antibody reduces the number of splenic marginal zone B cells in vivo by $\geqq$60%.

41. The antibody of claim 38, wherein the antibody decreases melanoma cell viability in vitro.

42. The antibody of claim 38, wherein the antibody suppresses growth of diffuse large B-cell lymphoma cells vitro.

43. A monoclonal antibody that binds to Notch2 negative regulatory region (NRR), wherein the antibody binds to a polypeptide comprising amino acids 1-44 and 188-256 of SEQ ID NO: 28.

44. The antibody of claim 43, wherein the antibody inhibits Notch2 activity.

45. A monoclonal antibody that binds to Notch2 negative regulatory region (NRR), and inhibits Notch2 activity, wherein the antibody competes for binding with the antibody of claim 4.

46. A monoclonal antibody that binds to Notch2 negative regulatory region (NRR) and inhibits Notch2 activity, wherein the antibody comprises a light chain variable domain comprising the amino acid sequence of SEQ ID NOs: 23, 24, or 25.

47. A method of inhibiting Notch2 activity, the method comprising exposing a cell that expresses Notch2 to the antibody of claim 38 or 43.

48. A method of treating a disorder associated with increased expression or activity of Notch2, the method comprising administering to a subject in need thereof an effective amount of the antibody of claim 38 or 43

* * * * *

SEQUENCE LISTING

```
<160> NUMBER OF SEQ ID NOS: 75

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      HVR-H1 of Antibody D peptide

<400> SEQUENCE: 1

Gly Tyr Ser Phe Thr Ser Tyr Gly Met Ser
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      HVR-H1 of Antibodies D-1, D-2, and D-3 peptide

<400> SEQUENCE: 2

Gly Tyr Thr Phe Ser Ser Tyr Gly Met Ser
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      HVR-H1 consensus sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Ser or Thr

<400> SEQUENCE: 3

Gly Tyr Xaa Phe Xaa Ser Tyr Gly Met Ser
1               5                   10


<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      HVR-H2 of Antibodies D, D-1, D-2, and D-3 peptide

<400> SEQUENCE: 4

Ser Tyr Ile Tyr Pro Tyr Ser Gly Ala Thr Tyr Tyr Ala Asp Ser Val
1               5                   10                  15
```

Lys Gly

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
HVR-H3 of Antibodies D, D-1, D-2, and D-3 peptide

<400> SEQUENCE: 5

His Ser Gly Tyr Tyr Arg Ile Ser Ser Ala Met Asp Val
1 5 10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
HVR-L1 of Antibody D peptide

<400> SEQUENCE: 6

Arg Ala Ser Gln Ser Ile Ser Ser Tyr Leu Ala
1 5 10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
HVR-L1 of Antibody D-1 peptide

<400> SEQUENCE: 7

Arg Ala Ser Gln Ser Asn Arg Arg Phe Leu Ala
1 5 10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
HVR-L1 of Antibody D-2 peptide

<400> SEQUENCE: 8

Arg Ala Ser Gln Ser Val Arg Ser Phe Leu Ala
1 5 10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
HVR-L1 of Antibody D-3 peptide

<400> SEQUENCE: 9

Arg Ala Ser Gln Asn Ile Lys Arg Phe Leu Ala
1 5 10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic HVR-L1 consensus sequence
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Ile, Asn or Val
<220> FEATURE:
<221> NAME/KEY: MOD_RES
<222> LOCATION: (7)..(7)
<223> OTHER INFORMATION: Ser, Arg or Lys
<220> FEATURE:
<221> NAME/KEY: MOD_RES
<222> LOCATION: (8)..(8)
<223> OTHER INFORMATION: Ser or Arg
<220> FEATURE:
<221> NAME/KEY: MOD_RES
<222> LOCATION: (9)..(9)
<223> OTHER INFORMATION: Tyr or Phe

<400> SEQUENCE: 10

```
Arg Ala Ser Gln Xaa Xaa Xaa Xaa Xaa Leu Ala
1               5                   10
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
HVR-L2 of Antibodies D and D-1 peptide

<400> SEQUENCE: 11

```
Gly Ala Ser Ser Arg Ala Ser
1               5
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
HVR-L2 of Antibody D-2 peptide

<400> SEQUENCE: 12

```
Arg Ala Ser Ile Arg Ala Ser
1               5
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
HVR-L2 of Antibody D-3 peptide

<400> SEQUENCE: 13

```
Gly Ala Ser Thr Arg Glu Ser
1               5
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
HVR-L2 consensus sequence
<220> FEATURE:
<221> NAME/KEY: MOD_RES
<222> LOCATION: (1)..(1)

<223> OTHER INFORMATION: Gly or Arg
<220> FEATURE:
<221> NAME/KEY: MOD_RES
<222> LOCATION: (4)..(4)
<223> OTHER INFORMATION: Ser, Ile or Thr
<220> FEATURE:
<221> NAME/KEY: MOD_RES
<222> LOCATION: (6)..(6)
<223> OTHER INFORMATION: Ala or Glu

<400> SEQUENCE: 14

Xaa Ala Ser Xaa Arg Xaa Ser
1 5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic HVR-L3 of Antibody D peptide

<400> SEQUENCE: 15

Gln Gln Tyr Tyr Ser Ser Pro Leu Thr
1 5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic HVR-L3 of Antibody D-1 peptide

<400> SEQUENCE: 16

Gln Gln Tyr Tyr Ile Ser Pro Leu Thr
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic HVR-L3 of Antibody D-2 peptide

<400> SEQUENCE: 17

Gln Gln Tyr Tyr Ile Ser Pro Trp Thr
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic HVR-L3 of Antibody D-3 peptide

<400> SEQUENCE: 18

Gln Gln Tyr Tyr Arg Ser Pro His Thr
1 5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic HVR-L3 consensus sequence
<220> FEATURE:

```
<221> NAME/KEY: MOD_RES
<222> LOCATION: (5)..(5)
<223> OTHER INFORMATION: Ser, Ile or Arg
<220> FEATURE:
<221> NAME/KEY: MOD_RES
<222> LOCATION: (8)..(8)
<223> OTHER INFORMATION: Leu, Trp or His

<400> SEQUENCE: 19

Gln Gln Tyr Tyr Xaa Ser Pro Xaa Thr
1               5


<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      Heavy chain variable region of Antibody D polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Ser Tyr
            20                  25                  30

Gly Met Ser Trp Val Arg Gln Ala Pro Gly Lys Gly Leu Glu Trp Val
        35                  40                  45

Ser Tyr Ile Tyr Pro Tyr Ser Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Tyr Arg Ile Ser Ser Ala Met Asp Val Trp
            100                 105                 110

Gly Gln Gly Thr Leu Val Thr Val Ser Ala
        115                 120


<210> SEQ ID NO 21
<211> LENGTH: 122
<212> TYPE: PRT
<213> ORGANISM: Artificial Sequence
<220> FEATURE:
<223> OTHER INFORMATION: Description of Artificial Sequence: Synthetic
      Heavy chain variable region of Antibodies D-1, D-2, and D-3
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Gly Met Ser Trp Val Arg Gln Ala Pro Gly Lys Gly Leu Glu Trp Val
        35                  40                  45

Ser Tyr Ile Tyr Pro Tyr Ser Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Gly Tyr Tyr Arg Ile Ser Ser Ala Met Asp Val Trp
            100                 105                 110
```

Gly Gln Gly Thr Leu Val Thr Val Ser Ala
115 120

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic Light chain variable region of Antibody D polypeptide

<400> SEQUENCE: 22

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Ala Trp Tyr Gln Gln Lys Pro Gly Lys Ala Pro Lys Leu Leu Ile
35 40 45

Tyr Gly Ala Ser Ser Arg Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ser Ser Pro Leu
85 90 95

Thr Phe Gly Gln Gly Thr Lys Val Glu Ile Lys Arg
100 105

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic Light chain variable region of Antibody D-1 polypeptide

<400> SEQUENCE: 23

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Asn Arg Arg Phe
20 25 30

Leu Ala Trp Tyr Gln Gln Lys Pro Gly Lys Ala Pro Lys Leu Leu Ile
35 40 45

Tyr Gly Ala Ser Ser Arg Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Ser Pro Leu
85 90 95

Thr Phe Gly Gln Gly Thr Lys Val Glu Ile Lys Arg
100 105

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic Light chain variable region of Antibody D-2 polypeptide

<400> SEQUENCE: 24

Asp Ile Gln Met Thr Gln Ser Pro Ser Ser Leu Ser Ala Ser Val Gly

```
1               5                   10                  15

Asp Arg Val Thr Ile Thr Cys Arg Ala Ser Gln Ser Val Arg Ser Phe
            20                  25                  30

Leu Ala Trp Tyr Gln Gln Lys Pro Gly Lys Ala Pro Lys Leu Leu Ile
        35                  40                  45

Tyr Arg Ala Ser Ile Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Ser Pro Trp
                85                  90                  95

Thr Phe Gly Gln Gly Thr Lys Val Glu Ile Lys Arg
            100                 105


<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic
      Light chain variable region of Antibody D-3 polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Arg Phe
            20                  25                  30

Leu Ala Trp Tyr Gln Gln Lys Pro Gly Lys Ala Pro Lys Leu Leu Ile
        35                  40                  45

Tyr Gly Ala Ser Thr Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Arg Ser Pro His
                85                  90                  95

Thr Phe Gly Gln Gly Thr Lys Val Glu Ile Lys Arg
            100                 105


<210> SEQ ID NO 26
<211> LENGTH: 288
<212> TYPE: PRT
<213> ORGANISM: Homo sapiens

<400> SEQUENCE: 26

Glu Glu Ala Cys Glu Leu Pro Glu Cys Gln Glu Asp Ala Gly Asn Lys
1               5                   10                  15

Val Cys Ser Leu Gln Cys Asn Asn His Ala Cys Gly Trp Asp Gly Gly
            20                  25                  30

Asp Cys Ser Leu Asn Phe Asn Asp Pro Trp Lys Asn Cys Thr Gln Ser
        35                  40                  45

Leu Gln Cys Trp Lys Tyr Phe Ser Asp Gly His Cys Asp Ser Gln Cys
    50                  55                  60

Asn Ser Ala Gly Cys Leu Phe Asp Gly Phe Asp Cys Gln Arg Ala Glu
65                  70                  75                  80

Gly Gln Cys Asn Pro Leu Tyr Asp Gln Tyr Cys Lys Asp His Phe Ser
                85                  90                  95

Asp Gly His Cys Asp Gln Gly Cys Asn Ser Ala Glu Cys Glu Trp Asp
            100                 105                 110
```

```
Gly Leu Asp Cys Ala Glu His Val Pro Glu Arg Leu Ala Ala Gly Thr
        115                 120                 125

Leu Val Val Val Val Leu Met Pro Pro Glu Gln Leu Arg Asn Ser Ser
    130                 135                 140

Phe His Phe Leu Arg Glu Leu Ser Arg Val Leu His Thr Asn Val Val
145                 150                 155                 160

Phe Lys Arg Asp Ala His Gly Gln Gln Met Ile Phe Pro Tyr Tyr Gly
                165                 170                 175

Arg Glu Glu Glu Leu Arg Lys His Pro Ile Lys Arg Ala Ala Glu Gly
            180                 185                 190

Trp Ala Ala Pro Asp Ala Leu Leu Gly Gln Val Lys Ala Ser Leu Leu
        195                 200                 205

Pro Gly Gly Ser Glu Gly Gly Arg Arg Arg Arg Glu Leu Asp Pro Met
    210                 215                 220

Asp Val Arg Gly Ser Ile Val Tyr Leu Glu Ile Asp Asn Arg Gln Cys
225                 230                 235                 240

Val Gln Ala Ser Ser Gln Cys Phe Gln Ser Ala Thr Asp Val Ala Ala
                245                 250                 255

Phe Leu Gly Ala Leu Ala Ser Leu Gly Ser Leu Asn Ile Pro Tyr Lys
            260                 265                 270

Ile Glu Ala Val Gln Ser Glu Thr Val Glu Pro Pro Pro Pro Ala Gln
        275                 280                 285


<210> SEQ ID NO 27
<211> LENGTH: 278
<212> TYPE: PRT
<213> ORGANISM: Mus sp.

<400> SEQUENCE: 27

Glu Glu Ala Cys Glu Leu Pro Glu Cys Gln Val Asp Ala Gly Asn Lys
1               5                   10                  15

Val Cys Asn Leu Gln Cys Asn Asn His Ala Cys Gly Trp Asp Gly Gly
            20                  25                  30

Asp Cys Ser Leu Asn Phe Asn Asp Pro Trp Lys Asn Cys Thr Gln Ser
        35                  40                  45

Leu Gln Cys Trp Lys Tyr Phe Ser Asp Gly His Cys Asp Ser Gln Cys
    50                  55                  60

Asn Ser Ala Gly Cys Leu Phe Asp Gly Phe Asp Cys Gln Leu Thr Glu
65                  70                  75                  80

Gly Gln Cys Asn Pro Leu Tyr Asp Gln Tyr Cys Lys Asp His Phe Ser
                85                  90                  95

Asp Gly His Cys Asp Gln Gly Cys Asn Ser Ala Glu Cys Glu Trp Asp
            100                 105                 110

Gly Leu Asp Cys Ala Glu His Val Pro Glu Arg Leu Ala Ala Gly Thr
        115                 120                 125

Leu Val Leu Val Val Leu Leu Pro Pro Asp Gln Leu Arg Asn Asn Ser
    130                 135                 140

Phe His Phe Leu Arg Glu Leu Ser His Val Leu His Thr Asn Val Val
145                 150                 155                 160

Phe Lys Arg Asp Ala Gln Gly Gln Gln Met Ile Phe Pro Tyr Tyr Gly
                165                 170                 175

His Glu Glu Glu Leu Arg Lys His Pro Ile Lys Arg Ser Thr Val Gly
            180                 185                 190

Trp Ala Thr Ser Ser Leu Leu Pro Gly Thr Ser Gly Gly Arg Gln Arg
        195                 200                 205
```

```
Arg Glu Leu Asp Pro Met Asp Ile Arg Gly Ser Ile Val Tyr Leu Glu
    210                 215                 220

Ile Asp Asn Arg Gln Cys Val Gln Ser Ser Ser Gln Cys Phe Gln Ser
225                 230                 235                 240

Ala Thr Asp Val Ala Ala Phe Leu Gly Ala Leu Ala Ser Leu Gly Ser
                245                 250                 255

Leu Asn Ile Pro Tyr Lys Ile Glu Ala Val Lys Ser Glu Pro Val Glu
            260                 265                 270

Pro Pro Leu Pro Ser Gln
        275


<210> SEQ ID NO 28
<211> LENGTH: 256
<212> TYPE: PRT
<213> ORGANISM: Homo sapiens

<400> SEQUENCE: 28

Pro Ala Thr Cys Leu Ser Gln Tyr Cys Ala Asp Lys Ala Arg Asp Gly
1               5                   10                  15

Val Cys Asp Glu Ala Cys Asn Ser His Ala Cys Gln Trp Asp Gly Gly
            20                  25                  30

Asp Cys Ser Leu Thr Met Glu Asn Pro Trp Ala Asn Cys Ser Ser Pro
        35                  40                  45

Leu Pro Cys Trp Asp Tyr Ile Asn Asn Gln Cys Asp Glu Leu Cys Asn
    50                  55                  60

Thr Val Glu Cys Leu Phe Asp Asn Phe Glu Cys Gln Gly Asn Ser Lys
65                  70                  75                  80

Thr Cys Lys Tyr Asp Lys Tyr Cys Ala Asp His Phe Lys Asp Asn His
                85                  90                  95

Cys Asp Gln Gly Cys Asn Ser Glu Glu Cys Gly Trp Asp Gly Leu Asp
            100                 105                 110

Cys Ala Ala Asp Gln Pro Glu Asn Leu Ala Glu Gly Thr Leu Val Ile
        115                 120                 125

Val Val Leu Met Pro Pro Glu Gln Leu Leu Gln Asp Ala Arg Ser Phe
    130                 135                 140

Leu Arg Ala Leu Gly Thr Leu Leu His Thr Asn Leu Arg Ile Lys Arg
145                 150                 155                 160

Asp Ser Gln Gly Glu Leu Met Val Tyr Pro Tyr Tyr Gly Glu Lys Ser
                165                 170                 175

Ala Ala Met Lys Lys Gln Arg Met Thr Arg Arg Ser Leu Pro Gly Glu
            180                 185                 190

Gln Glu Gln Glu Val Ala Gly Ser Lys Val Phe Leu Glu Ile Asp Asn
        195                 200                 205

Arg Gln Cys Val Gln Asp Ser Asp His Cys Phe Lys Asn Thr Asp Ala
    210                 215                 220

Ala Ala Ala Leu Leu Ala Ser His Ala Ile Gln Gly Thr Leu Ser Tyr
225                 230                 235                 240

Pro Leu Val Ser Val Val Ser Glu Ser Leu Thr Pro Glu Arg Thr Gln
                245                 250                 255


<210> SEQ ID NO 29
<211> LENGTH: 258
<212> TYPE: PRT
<213> ORGANISM: Mus sp.

<400> SEQUENCE: 29
```

-continued

Pro Ala Thr Cys Gln Ser Gln Tyr Cys Ala Asp Lys Ala Arg Asp Gly
1 5 10 15

Ile Cys Asp Glu Ala Cys Asn Ser His Ala Cys Gln Trp Asp Gly Gly
20 25 30

Asp Cys Ser Leu Thr Met Glu Asp Pro Trp Ala Asn Cys Thr Ser Thr
35 40 45

Leu Arg Cys Trp Glu Tyr Ile Asn Asn Gln Cys Asp Glu Gln Cys Asn
50 55 60

Thr Ala Glu Cys Leu Phe Asp Asn Phe Glu Cys Gln Arg Asn Ser Lys
65 70 75 80

Thr Cys Lys Tyr Asp Lys Tyr Cys Ala Asp His Phe Lys Asp Asn His
85 90 95

Cys Asp Gln Gly Cys Asn Ser Glu Glu Cys Gly Trp Asp Gly Leu Asp
100 105 110

Cys Ala Ser Asp Gln Pro Glu Asn Leu Ala Glu Gly Thr Leu Ile Ile
115 120 125

Val Val Leu Leu Pro Pro Glu Gln Leu Leu Gln Asp Ser Arg Ser Phe
130 135 140

Leu Arg Ala Leu Gly Thr Leu Leu His Thr Asn Leu Arg Ile Lys Gln
145 150 155 160

Asp Ser Gln Gly Ala Leu Met Val Tyr Pro Tyr Phe Gly Glu Lys Ser
165 170 175

Ala Ala Met Lys Lys Gln Lys Met Thr Arg Arg Ser Leu Pro Glu Glu
180 185 190

Gln Glu Gln Glu Gln Glu Val Ile Gly Ser Lys Ile Phe Leu Glu Ile
195 200 205

Asp Asn Arg Gln Cys Val Gln Asp Ser Asp Gln Cys Phe Lys Asn Thr
210 215 220

Asp Ala Ala Ala Ala Leu Leu Ala Ser His Ala Ile Gln Gly Thr Leu
225 230 235 240

Ser Tyr Pro Leu Val Ser Val Phe Ser Glu Leu Glu Ser Pro Arg Asn
245 250 255

Ala Gln

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Gly Val Pro Ser Arg Phe Ser Gly Ser Arg Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic framework region 4 peptide

<400> SEQUENCE: 31

Phe Arg Gln Gly Thr Lys Val Glu Ile Lys
1 5 10

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Trp Val Arg Gln Ala Pro Gly Gln Gly Leu Glu Trp Met Gly
1 5 10

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Trp Gly Gln Gly Thr Leu Val Thr Val Ser Ser
1 5 10

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Trp Val Arg Gln Ala Pro Gly Gln Gly Leu Glu Trp Met
1 5 10

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala
20 25 30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Val Ser
20 25 30

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Trp Ile Arg Gln Pro Pro Gly Lys Gly Leu Glu Trp Ile Gly
1 5 10

-continued

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

```
Gln Val Gln Leu Gln Glu Ser Gly Pro Gly Leu Val Lys Pro Ser Gln
1               5                   10                  15

Thr Leu Ser Leu Thr Cys Thr Val Ser
            20                  25
```

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

```
Trp Ile Arg Gln Pro Pro Gly Lys Gly Leu Glu Trp Ile
1               5                   10
```

<210> SEQ ID NO 45
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30
```

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30
```

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Trp Val Arg Gln Ala Pro Gly Lys Gly Leu Glu Trp Val Ser
1               5                   10
```

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Trp Val Arg Gln Ala Pro Gly Lys Gly Leu Glu Trp Val
1               5                   10
```

-continued

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30
```

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30
```

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30
```

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30
```

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Arg Phe Thr Ile Ser Ala Asp Thr Ser Lys Asn Thr Ala Tyr Leu Gln
```

1 5 10 15

Met Asn Ser Leu Arg Ala Glu Asp Thr Ala Val Tyr Tyr Cys Ser
20 25 30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala Arg
20 25 30

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala
20 25 30

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys
20 25 30

<210> SEQ ID NO 60
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Trp Tyr Gln Gln Lys Pro Gly Lys Ala Pro Lys Leu Leu Ile Tyr
1 5 10 15

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Phe Gly Gln Gly Thr Lys Val Glu Ile Lys
1 5 10

<210> SEQ ID NO 64
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Asp Ile Val Met Thr Gln Ser Pro Leu Ser Leu Pro Val Thr Pro Gly
1 5 10 15

Glu Pro Ala Ser Ile Ser Cys
20

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Trp Tyr Leu Gln Lys Pro Gly Gln Ser Pro Gln Leu Leu Ile Tyr
1 5 10 15

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

-continued

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 67
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Trp Tyr Gln Gln Lys Pro Gly Gln Ala Pro Arg Leu Leu Ile Tyr
1 5 10 15

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Asp Ile Val Met Thr Gln Ser Pro Asp Ser Leu Ala Val Ser Leu Gly
1 5 10 15

Glu Arg Ala Thr Ile Asn Cys
20

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Trp Tyr Gln Gln Lys Pro Gly Gln Pro Pro Lys Leu Leu Ile Tyr
1 5 10 15

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 73
<211> LENGTH: 396
<212> TYPE: PRT
<213> ORGANISM: Artificial Sequence
<220> FEATURE:
<223> OTHER INFORMATION: Description of Artificial Sequence: Synthetic Tagged human Notch2 NRR antigen polypeptide

<400> SEQUENCE: 73

Lys Asp Asp Asp Asp Lys Gly Ser Gly Asp Val Cys Pro Gln Met Pro
1 5 10 15

Cys Leu Asn Gly Gly Thr Cys Ala Val Ala Ser Asn Met Pro Asp Gly
20 25 30

Phe Ile Cys Arg Cys Pro Pro Gly Phe Ser Gly Ala Arg Cys Gln Ser
35 40 45

Ser Cys Gly Gln Val Lys Cys Arg Lys Gly Glu Gln Cys Val His Thr
50 55 60

Ala Ser Gly Pro Arg Cys Phe Cys Pro Ser Pro Arg Asp Cys Glu Ser
65 70 75 80

Gly Cys Ala Ser Ser Pro Cys Gln His Gly Gly Ser Cys His Pro Gln
85 90 95

Arg Gln Pro Pro Tyr Tyr Ser Cys Gln Cys Ala Pro Pro Phe Ser Gly
100 105 110

Ser Arg Cys Glu Leu Tyr Thr Ala Pro Pro Ser Thr Pro Pro Ala Thr
115 120 125

Cys Leu Ser Gln Tyr Cys Ala Asp Lys Ala Arg Asp Gly Val Cys Asp
130 135 140

Glu Ala Cys Asn Ser His Ala Cys Gln Trp Asp Gly Gly Asp Cys Ser
145 150 155 160

Leu Thr Met Glu Asn Pro Trp Ala Asn Cys Ser Ser Pro Leu Pro Cys
165 170 175

Trp Asp Tyr Ile Asn Asn Gln Cys Asp Glu Leu Cys Asn Thr Val Glu
180 185 190

Cys Leu Phe Asp Asn Phe Glu Cys Gln Gly Asn Ser Lys Thr Cys Lys
195 200 205

Tyr Asp Lys Tyr Cys Ala Asp His Phe Lys Asp Asn His Cys Asn Gln
210 215 220

Gly Cys Asn Ser Glu Glu Cys Gly Trp Asp Gly Leu Asp Cys Ala Ala
225 230 235 240

Asp Gln Pro Glu Asn Leu Ala Glu Gly Thr Leu Val Ile Val Val Leu
245 250 255

```
Met Pro Pro Glu Gln Leu Leu Gln Asp Ala Arg Ser Phe Leu Arg Ala
            260                 265                 270

Leu Gly Thr Leu Leu His Thr Asn Leu Arg Ile Lys Arg Asp Ser Gln
        275                 280                 285

Gly Glu Leu Met Val Tyr Pro Tyr Tyr Gly Glu Lys Ser Ala Ala Met
    290                 295                 300

Lys Lys Gln Arg Met Thr Arg Arg Ser Leu Pro Gly Glu Gln Glu Gln
305                 310                 315                 320

Glu Val Ala Gly Ser Lys Val Phe Leu Glu Ile Asp Asn Arg Gln Cys
                325                 330                 335

Val Gln Asp Ser Asp His Cys Phe Lys Asn Thr Asp Ala Ala Ala Ala
            340                 345                 350

Leu Leu Ala Ser His Ala Ile Gln Gly Thr Leu Ser Tyr Pro Leu Val
        355                 360                 365

Ser Val Val Ser Glu Ser Leu Thr Pro Glu Arg Thr Glu Phe Gly Leu
    370                 375                 380

Val Pro Arg Gly Ser Gly His His His His His His
385                 390                 395


<210> SEQ ID NO 74
<211> LENGTH: 394
<212> TYPE: PRT
<213> ORGANISM: Artificial Sequence
<220> FEATURE:
<223> OTHER INFORMATION: Description of Artificial Sequence: Synthetic
      Tagged mouse Notch2 NRR antigen polypeptide

<400> SEQUENCE: 74

Ala Asp Val Cys Pro Gln Lys Pro Cys Leu Asn Gly Gly Thr Cys Ala
1               5                   10                  15

Val Ala Ser Asn Met Pro Asp Gly Phe Ile Cys Arg Cys Pro Pro Gly
            20                  25                  30

Phe Ser Gly Ala Arg Cys Gln Ser Ser Cys Gly Gln Val Lys Cys Arg
        35                  40                  45

Arg Gly Glu Gln Cys Ile His Thr Asp Ser Gly Pro Arg Cys Phe Cys
    50                  55                  60

Leu Asn Pro Lys Asp Cys Glu Ser Gly Cys Ala Ser Asn Pro Cys Gln
65                  70                  75                  80

His Gly Gly Thr Cys Tyr Pro Gln Arg Gln Pro Pro His Tyr Ser Cys
                85                  90                  95

Arg Cys Pro Pro Ser Phe Gly Gly Ser His Cys Glu Leu Tyr Thr Ala
            100                 105                 110

Pro Thr Ser Thr Pro Pro Ala Thr Cys Gln Ser Gln Tyr Cys Ala Asp
        115                 120                 125

Lys Ala Arg Asp Gly Ile Cys Asp Glu Ala Cys Asn Ser His Ala Cys
    130                 135                 140

Gln Trp Asp Gly Gly Asp Cys Ser Leu Thr Met Glu Asp Pro Trp Ala
145                 150                 155                 160

Asn Cys Thr Ser Thr Leu Arg Cys Trp Glu Tyr Ile Asn Asn Gln Cys
                165                 170                 175

Asp Glu Gln Cys Asn Thr Ala Glu Cys Leu Phe Asp Asn Phe Glu Cys
            180                 185                 190

Gln Arg Asn Ser Lys Thr Cys Lys Tyr Asp Lys Tyr Cys Ala Asp His
        195                 200                 205

Phe Lys Asp Asn His Cys Asp Gln Gly Cys Asn Ser Glu Glu Cys Gly
    210                 215                 220
```

```
Trp Asp Gly Leu Asp Cys Ala Ser Asp Gln Pro Glu Asn Leu Ala Glu
225                 230                 235                 240

Gly Thr Leu Ile Ile Val Val Leu Leu Pro Pro Glu Gln Leu Leu Gln
                245                 250                 255

Asp Ser Arg Ser Phe Leu Arg Ala Leu Gly Thr Leu Leu His Thr Asn
            260                 265                 270

Leu Arg Ile Lys Gln Asp Ser Gln Gly Ala Leu Met Val Tyr Pro Tyr
        275                 280                 285

Phe Gly Glu Lys Ser Ala Ala Met Lys Lys Gln Lys Met Thr Arg Arg
    290                 295                 300

Ser Leu Pro Glu Glu Gln Glu Gln Glu Gln Glu Val Ile Gly Ser Lys
305                 310                 315                 320

Ile Phe Leu Glu Ile Asp Asn Arg Gln Cys Val Gln Asp Ser Asp Gln
                325                 330                 335

Cys Phe Lys Asn Thr Asp Ala Ala Ala Ala Leu Leu Ala Ser His Ala
            340                 345                 350

Ile Gln Gly Thr Leu Ser Tyr Pro Leu Val Ser Val Phe Ser Glu Leu
        355                 360                 365

Glu Ser Pro Arg Asn Ala Arg Arg Ala Gly Ser Gly Asp Tyr Lys Asp
    370                 375                 380

Asp Asp Asp Lys Glu Asn Leu Tyr Phe Gln
385                 390


<210> SEQ ID NO 75
<211> LENGTH: 2471
<212> TYPE: PRT
<213> ORGANISM: Homo sapiens

<400> SEQUENCE: 75

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205
```

```
Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
```

-continued 625 630 635 640

Asn Cys Glu Ile Asn Phe Asp Asp Cys Ala Ser Asn Pro Cys Ile His
645 650 655

Gly Ile Cys Met Asp Gly Ile Asn Arg Tyr Ser Cys Val Cys Ser Pro
660 665 670

Gly Phe Thr Gly Gln Arg Cys Asn Ile Asp Ile Asp Glu Cys Ala Ser
675 680 685

Asn Pro Cys Arg Lys Gly Ala Thr Cys Ile Asn Gly Val Asn Gly Phe
690 695 700

Arg Cys Ile Cys Pro Glu Gly Pro His His Pro Ser Cys Tyr Ser Gln
705 710 715 720

Val Asn Glu Cys Leu Ser Asn Pro Cys Ile His Gly Asn Cys Thr Gly
725 730 735

Gly Leu Ser Gly Tyr Lys Cys Leu Cys Asp Ala Gly Trp Val Gly Ile
740 745 750

Asn Cys Glu Val Asp Lys Asn Glu Cys Leu Ser Asn Pro Cys Gln Asn
755 760 765

Gly Gly Thr Cys Asp Asn Leu Val Asn Gly Tyr Arg Cys Thr Cys Lys
770 775 780

Lys Gly Phe Lys Gly Tyr Asn Cys Gln Val Asn Ile Asp Glu Cys Ala
785 790 795 800

Ser Asn Pro Cys Leu Asn Gln Gly Thr Cys Phe Asp Asp Ile Ser Gly
805 810 815

Tyr Thr Cys His Cys Val Leu Pro Tyr Thr Gly Lys Asn Cys Gln Thr
820 825 830

Val Leu Ala Pro Cys Ser Pro Asn Pro Cys Glu Asn Ala Ala Val Cys
835 840 845

Lys Glu Ser Pro Asn Phe Glu Ser Tyr Thr Cys Leu Cys Ala Pro Gly
850 855 860

Trp Gln Gly Gln Arg Cys Thr Ile Asp Ile Asp Glu Cys Ile Ser Lys
865 870 875 880

Pro Cys Met Asn His Gly Leu Cys His Asn Thr Gln Gly Ser Tyr Met
885 890 895

Cys Glu Cys Pro Pro Gly Phe Ser Gly Met Asp Cys Glu Glu Asp Ile
900 905 910

Asp Asp Cys Leu Ala Asn Pro Cys Gln Asn Gly Gly Ser Cys Met Asp
915 920 925

Gly Val Asn Thr Phe Ser Cys Leu Cys Leu Pro Gly Phe Thr Gly Asp
930 935 940

Lys Cys Gln Thr Asp Met Asn Glu Cys Leu Ser Glu Pro Cys Lys Asn
945 950 955 960

Gly Gly Thr Cys Ser Asp Tyr Val Asn Ser Tyr Thr Cys Lys Cys Gln
965 970 975

Ala Gly Phe Asp Gly Val His Cys Glu Asn Asn Ile Asn Glu Cys Thr
980 985 990

Glu Ser Ser Cys Phe Asn Gly Gly Thr Cys Val Asp Gly Ile Asn Ser
995 1000 1005

Phe Ser Cys Leu Cys Pro Val Gly Phe Thr Gly Ser Phe Cys Leu
1010 1015 1020

His Glu Ile Asn Glu Cys Ser Ser His Pro Cys Leu Asn Glu Gly
1025 1030 1035

Thr Cys Val Asp Gly Leu Gly Thr Tyr Arg Cys Ser Cys Pro Leu
1040 1045 1050

-continued

```
Gly Tyr  Thr Gly Lys Asn Cys  Gln Thr Leu Val Asn  Leu Cys Ser
    1055                 1060                 1065

Arg Ser  Pro Cys Lys Asn Lys  Gly Thr Cys Val Gln  Lys Lys Ala
    1070                 1075                 1080

Glu Ser  Gln Cys Leu Cys Pro  Ser Gly Trp Ala Gly  Ala Tyr Cys
    1085                 1090                 1095

Asp Val  Pro Asn Val Ser Cys  Asp Ile Ala Ala Ser  Arg Arg Gly
    1100                 1105                 1110

Val Leu  Val Glu His Leu Cys  Gln His Ser Gly Val  Cys Ile Asn
    1115                 1120                 1125

Ala Gly  Asn Thr His Tyr Cys  Gln Cys Pro Leu Gly  Tyr Thr Gly
    1130                 1135                 1140

Ser Tyr  Cys Glu Glu Gln Leu  Asp Glu Cys Ala Ser  Asn Pro Cys
    1145                 1150                 1155

Gln His  Gly Ala Thr Cys Ser  Asp Phe Ile Gly Gly  Tyr Arg Cys
    1160                 1165                 1170

Glu Cys  Val Pro Gly Tyr Gln  Gly Val Asn Cys Glu  Tyr Glu Val
    1175                 1180                 1185

Asp Glu  Cys Gln Asn Gln Pro  Cys Gln Asn Gly Gly  Thr Cys Ile
    1190                 1195                 1200

Asp Leu  Val Asn His Phe Lys  Cys Ser Cys Pro Pro  Gly Thr Arg
    1205                 1210                 1215

Gly Leu  Leu Cys Glu Glu Asn  Ile Asp Asp Cys Ala  Arg Gly Pro
    1220                 1225                 1230

His Cys  Leu Asn Gly Gly Gln  Cys Met Asp Arg Ile  Gly Gly Tyr
    1235                 1240                 1245

Ser Cys  Arg Cys Leu Pro Gly  Phe Ala Gly Glu Arg  Cys Glu Gly
    1250                 1255                 1260

Asp Ile  Asn Glu Cys Leu Ser  Asn Pro Cys Ser Ser  Glu Gly Ser
    1265                 1270                 1275

Leu Asp  Cys Ile Gln Leu Thr  Asn Asp Tyr Leu Cys  Val Cys Arg
    1280                 1285                 1290

Ser Ala  Phe Thr Gly Arg His  Cys Glu Thr Phe Val  Asp Val Cys
    1295                 1300                 1305

Pro Gln  Met Pro Cys Leu Asn  Gly Gly Thr Cys Ala  Val Ala Ser
    1310                 1315                 1320

Asn Met  Pro Asp Gly Phe Ile  Cys Arg Cys Pro Pro  Gly Phe Ser
    1325                 1330                 1335

Gly Ala  Arg Cys Gln Ser Ser  Cys Gly Gln Val Lys  Cys Arg Lys
    1340                 1345                 1350

Gly Glu  Gln Cys Val His Thr  Ala Ser Gly Pro Arg  Cys Phe Cys
    1355                 1360                 1365

Pro Ser  Pro Arg Asp Cys Glu  Ser Gly Cys Ala Ser  Ser Pro Cys
    1370                 1375                 1380

Gln His  Gly Gly Ser Cys His  Pro Gln Arg Gln Pro  Pro Tyr Tyr
    1385                 1390                 1395

Ser Cys  Gln Cys Ala Pro Pro  Phe Ser Gly Ser Arg  Cys Glu Leu
    1400                 1405                 1410

Tyr Thr  Ala Pro Pro Ser Thr  Pro Pro Ala Thr Cys  Leu Ser Gln
    1415                 1420                 1425

Tyr Cys  Ala Asp Lys Ala Arg  Asp Gly Val Cys Asp  Glu Ala Cys
    1430                 1435                 1440

Asn Ser  His Ala Cys Gln Trp  Asp Gly Gly Asp Cys  Ser Leu Thr
    1445                 1450                 1455
```

```
Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
    1730                1735                1740

Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
    1760                1765                1770

Glu Ala Leu Leu Ser Glu Glu Asp Asp Pro Ile Asp Arg Arg Pro
    1775                1780                1785

Trp Thr Gln Gln His Leu Glu Ala Ala Asp Ile Arg Arg Thr Pro
    1790                1795                1800

Ser Leu Ala Leu Thr Pro Pro Gln Ala Glu Gln Glu Val Asp Val
    1805                1810                1815

Leu Asp Val Asn Val Arg Gly Pro Asp Gly Cys Thr Pro Leu Met
    1820                1825                1830

Leu Ala Ser Leu Arg Gly Gly Ser Ser Asp Leu Ser Asp Glu Asp
    1835                1840                1845

Glu Asp Ala Glu Asp Ser Ser Ala Asn Ile Ile Thr Asp Leu Val
```

-continued

```
    1850                1855                1860

Tyr Gln  Gly Ala Ser Leu Gln  Ala Gln Thr Asp Arg  Thr Gly Glu
    1865                1870                1875

Met Ala  Leu His Leu Ala Ala  Arg Tyr Ser Arg Ala  Asp Ala Ala
    1880                1885                1890

Lys Arg  Leu Leu Asp Ala Gly  Ala Asp Ala Asn Ala  Gln Asp Asn
    1895                1900                1905

Met Gly  Arg Cys Pro Leu His  Ala Ala Val Ala Ala  Asp Ala Gln
    1910                1915                1920

Gly Val  Phe Gln Ile Leu Ile  Arg Asn Arg Val Thr  Asp Leu Asp
    1925                1930                1935

Ala Arg  Met Asn Asp Gly Thr  Thr Pro Leu Ile Leu  Ala Ala Arg
    1940                1945                1950

Leu Ala  Val Glu Gly Met Val  Ala Glu Leu Ile Asn  Cys Gln Ala
    1955                1960                1965

Asp Val  Asn Ala Val Asp Asp  His Gly Lys Ser Ala  Leu His Trp
    1970                1975                1980

Ala Ala  Ala Val Asn Asn Val  Glu Ala Thr Leu Leu  Leu Leu Lys
    1985                1990                1995

Asn Gly  Ala Asn Arg Asp Met  Gln Asp Asn Lys Glu  Glu Thr Pro
    2000                2005                2010

Leu Phe  Leu Ala Ala Arg Glu  Gly Ser Tyr Glu Ala  Ala Lys Ile
    2015                2020                2025

Leu Leu  Asp His Phe Ala Asn  Arg Asp Ile Thr Asp  His Met Asp
    2030                2035                2040

Arg Leu  Pro Arg Asp Val Ala  Arg Asp Arg Met His  His Asp Ile
    2045                2050                2055

Val Arg  Leu Leu Asp Glu Tyr  Asn Val Thr Pro Ser  Pro Pro Gly
    2060                2065                2070

Thr Val  Leu Thr Ser Ala Leu  Ser Pro Val Ile Cys  Gly Pro Asn
    2075                2080                2085

Arg Ser  Phe Leu Ser Leu Lys  His Thr Pro Met Gly  Lys Lys Ser
    2090                2095                2100

Arg Arg  Pro Ser Ala Lys Ser  Thr Met Pro Thr Ser  Leu Pro Asn
    2105                2110                2115

Leu Ala  Lys Glu Ala Lys Asp  Ala Lys Gly Ser Arg  Arg Lys Lys
    2120                2125                2130

Ser Leu  Ser Glu Lys Val Gln  Leu Ser Glu Ser Ser  Val Thr Leu
    2135                2140                2145

Ser Pro  Val Asp Ser Leu Glu  Ser Pro His Thr Tyr  Val Ser Asp
    2150                2155                2160

Thr Thr  Ser Ser Pro Met Ile  Thr Ser Pro Gly Ile  Leu Gln Ala
    2165                2170                2175

Ser Pro  Asn Pro Met Leu Ala  Thr Ala Ala Pro Pro  Ala Pro Val
    2180                2185                2190

His Ala  Gln His Ala Leu Ser  Phe Ser Asn Leu His  Glu Met Gln
    2195                2200                2205

Pro Leu  Ala His Gly Ala Ser  Thr Val Leu Pro Ser  Val Ser Gln
    2210                2215                2220

Leu Leu  Ser His His His Ile  Val Ser Pro Gly Ser  Gly Ser Ala
    2225                2230                2235

Gly Ser  Leu Ser Arg Leu His  Pro Val Pro Val Pro  Ala Asp Trp
    2240                2245                2250
```

-continued

```
Met Asn  Arg Met Glu Val Asn  Glu Thr Gln Tyr Asn  Glu Met Phe
    2255                 2260                 2265

Gly Met  Val Leu Ala Pro Ala  Glu Gly Thr His Pro  Gly Ile Ala
    2270                 2275                 2280

Pro Gln  Ser Arg Pro Pro Glu  Gly Lys His Ile Thr  Thr Pro Arg
    2285                 2290                 2295

Glu Pro  Leu Pro Pro Ile Val  Thr Phe Gln Leu Ile  Pro Lys Gly
    2300                 2305                 2310

Ser Ile  Ala Gln Pro Ala Gly  Ala Pro Gln Pro Gln  Ser Thr Cys
    2315                 2320                 2325

Pro Pro  Ala Val Ala Gly Pro  Leu Pro Thr Met Tyr  Gln Ile Pro
    2330                 2335                 2340

Glu Met  Ala Arg Leu Pro Ser  Val Ala Phe Pro Thr  Ala Met Met
    2345                 2350                 2355

Pro Gln  Gln Asp Gly Gln Val  Ala Gln Thr Ile Leu  Pro Ala Tyr
    2360                 2365                 2370

His Pro  Phe Pro Ala Ser Val  Gly Lys Tyr Pro Thr  Pro Pro Ser
    2375                 2380                 2385

Gln His  Ser Tyr Ala Ser Ser  Asn Ala Ala Glu Arg  Thr Pro Ser
    2390                 2395                 2400

His Ser  Gly His Leu Gln Gly  Glu His Pro Tyr Leu  Thr Pro Ser
    2405                 2410                 2415

Pro Glu  Ser Pro Asp Gln Trp  Ser Ser Ser Ser Pro  His Ser Ala
    2420                 2425                 2430

Ser Asp  Trp Ser Asp Val Thr  Thr Ser Pro Thr Pro  Gly Gly Ala
    2435                 2440                 2445

Gly Gly  Gly Gln Arg Gly Pro  Gly Thr His Met Ser  Glu Pro Pro
    2450                 2455                 2460

His Asn  Asn Met Gln Val Tyr  Ala
    2465                 2470
```